United States Patent
Foldes et al.

(10) Patent No.: US 6,500,634 B1
(45) Date of Patent: Dec. 31, 2002

(54) HUMAN CNS RECEPTORS OF THE NMDA-R1 FAMILY

(75) Inventors: Robert Foldes, Willowdale (CA); Rajender Kamboj, Mississauga (CA)

(73) Assignee: NPS Allelix Corp., Mississauga (CA)

( * ) Notice: Subject to any disclaimer, the term of this patent is extended or adjusted under 35 U.S.C. 154(b) by 0 days.

(21) Appl. No.: 08/164,487

(22) Filed: Dec. 10, 1993

Related U.S. Application Data

(63) Continuation-in-part of application No. 07/987,953, filed on Dec. 11, 1992, now abandoned.

(51) Int. Cl.[7] ............... C07K 14/705; C12N 15/12
(52) U.S. Cl. ............ 435/69.1; 435/7.21; 435/252.3; 435/320.1; 530/350; 536/23.5
(58) Field of Search ............ 435/6, 7.21, 69.1, 435/252.3, 320.1; 530/350; 536/23.5, 24.31

(56) References Cited

FOREIGN PATENT DOCUMENTS

WO    WO 94/11501    5/1994

OTHER PUBLICATIONS

P.N.A.S. 88:7557–7561, Sep. 1991, Puckett et al Molecular Cloning and Chromosomal Localization of One of the Human Glutamate Receptor Genes.*
P.N.A.S. 86:9762–9766, Dec., 1989, Grandy et al Cloning of the cDNA and Gene for a Human $D_2$ Dopamine Receptor.*
Nature 347:76–79, Sep. 06, 1990, Zhou et al Cloning and Expression of Human and Rat $D_1$ Dopamine Repecetors.*
Barnett et al., "Rapid Generation of DNA Fragments by PCR Amplicaton of Crude, Synthetic, Oligonucleotides," *Nucleic Acids Research*, vol. 18, No. 10, p. 3094 (1990).
Moriyoshi et al., "Molecular Cloning and Characterization of the Rat/NMDA Receptor," *Nature*, vol. 354, pp. 31–36 (Nov. 1991).
Sakimura et al., "Primary Structure and Expression of the $_y2$ Subunit of the Glutamate Receptor Channel Selective for Kainate," *Neuron*, vol. 8, pp. 267–274 (Feb. 1992).
Yamazaki et al., "Cloning, Expression and Modulation of a Mouse NMDA Receptor Subunit," *FEBS Letters*, vol. 300, No. 1, pp. 39–45 (Mar. 1992).

Meguro et al., "Functional Characterization of a Heteromeric NMDA Receptor Channels Expressed from Cloned cDNAs," *Nature*, vol. 357, pp. 70–74 (May 1992).
Monyer et al., "Heteromeric NMDA Receptors: Molecular and Functional Distinction of Subtypes," *Science*, vol. 256, pp. 1217 (May 1992).
Anantharam et al., "Combinatorial RNA Splicing Alters the Surface Change on the NMDA Receptor," *FEBS Letters*, vol. 305, No. 1, pp. 27–30 (Jun. 1992).
Sugihara et al., "Structures and Properties of Seven Isoforms of the NMDA Receptor Generated by Alternative Splicing," *Biochemical and Biophysical Research Communications*, vol. 185, No. 3, pp. 826–832 (Jun. 1992).
Kutsuwada et al., "Molecular Diversity of the NMDA Receptor Channel," *Nature*, vol. 358, pp. 36–41 (Jul. 1992).
Oksenberg et al., "A Single Amino–Acid Difference Confers Major Pharmacological Variation between Human and Rodent $5-HT_{1B}$ Receptors," *Nature*, vol. 360, pp. 161–163 (Nov. 1992).
Durand et al., "Cloning of an Apparent Splice Variant of the Rat N–methyl–D–aspartate Receptor NMDAR1 with Altered Sensitivity to Polyamines and Activators of Protein Kinase C," *Proc. Natl. Acad. Sci. USA*, vol. 89, pp. 9359–9363 (Oct. 1992).
William Sun, et al., "Molecular cloning, chromosomal mapping, and functional expression of human brain glutamate receptors"; Proc. Natl. Acad. Sci. USA, vol. 89, pp. 1443–1447, Feb. 1992.
Carmie Puckett, et al., "Molecular cloning and chromosomal localization of one of the human glutamate receptor genes"; Proc. Natl. Acad. Sci. USA, vol. 88, pp. 7557–7561, Sep. 1991.

* cited by examiner

*Primary Examiner*—John Ulm
(74) *Attorney, Agent, or Firm*—Foley & Lardner

(57) ABSTRACT

Neurotransmission by excitatory amino acids (EAAS) such as glutamate is mediated via membrane-bound surface receptors. DNA coding for EAA receptors of one family of human NMDA-binding type receptors has now been isolated and receptor proteins characterized. Herein described are recombinant cell lines which produce the EAA receptor as a heterologous membrane-bound product. Also described are related aspects of the invention, which are of commercial significance. Included is use of the cell lines as a tool for discovery of compounds which modulate EAA receptor stimulation.

12 Claims, 13 Drawing Sheets

```
Eco RI
GAATTCCGGTAAGGCTCTGGAAAAGGGGGCGCTGGGAGCGCATTGCGAGGGGGCTGGAGA
----------+---------+---------+---------+---------+---------+  60
CTTAAGGCCATTCCGAGACCTTTTCCCCCGCGACCCTCGCGTAACGCTCCCCCGACCTCT

GGGAGAGAGGAGCGGAAGCTGAGGGTGTGAAACGGCTGGCCCCGAACACACCTCGCGGCG
----------+---------+---------+---------+---------+---------+ 120
CCCTCTCTCCTCGCCTTCGACTCCCACACTTTGCCGACCGGGGCTTGTGTGGAGCGCCGC

CTCCAGTGATTCCTGGTGTCCGACCTCAGCCCCAGTCAGTGCGGGTCCAGTTTCCAGGCT
----------+---------+---------+---------+---------+---------+ 180
GAGGTCACTAAGGACCACAGGCTGGAGTCGGGGTCAGTCACGCCCAGGTCAAAGGTCCGA

CTCGCGGAAGGCCTGGCTGAGCACATGCGGCAGCCACGGTCGCCCTCCCTATTCCTCTTA
----------+---------+---------+---------+---------+---------+ 240
GAGCGCCTTCCGGACCGACTCGTGTACGCCGTCGGTGCCAGCGGGAGGGATAAGGAGAAT

GCCCGAGGAGGGGGGTCCCAAGTTACATGGCCACGCAGATGGGGCCTCTCCCTCATTTCT
----------+---------+---------+---------+---------+---------+ 300
CGGGCTCCTCCCCCCAGGGTTCAATGTACCGGTGCGTCTACCCCGGAGAGGGAGTAAAGA

GAACCTTGTGGGGAGGGGAACCTTGAAGGGAGCGCCCCCAGAGCCATGGCTTAGGGCCT
----------+---------+---------+---------+---------+---------+ 360
CTTGGAACACCCCTCCCCTTGGAACTTCCCTCGCGGGGGGTCTCGGTACCGAATCCCGGA

CCCCCACCCCTCTGGAGCTCCAGTCTGCAAGAGTCAGGAGCCGAAATATCGCTGACTGTG
----------+---------+---------+---------+---------+---------+ 420
GGGGGTGGGGAGACCTCGAGGTCAGACGTTCTCAGTCCTCGGCTTTATAGCGACTGACAC

GGTGACGACTCTTGCGCGCACACACACATACAAGCGGGCACGACGCGTTCGGTCCTATTA
----------+---------+---------+---------+---------+---------+ 480
CCACTGCTGAGAACGCGCGTGTGTGTATGTTCGCCCGTGCTGCGCAAGCCAGGATAAT

AAAGGCACGCAAGGGTGCGGCTGCACGCGGTGACACGGACCCCTCTAACGTTTCCAAACT
----------+---------+---------+---------+---------+---------+ 540
TTTCCGTGCGTTCCCACGCCGACGTGCGCCACTGTGCCTGGGGAGATTGCAAAGGTTTGA

GAGCTCCCTGCAGGTCCCCGACAGCACAGGCCCCTGTCCCAGGACCCCTCCAGGCACGCG
----------+---------+---------+---------+---------+---------+ 600
CTCGAGGGACGTCCAGGGGCTGTCGTGTCCGGGGACAGGGTCCTGGGGAGGTCCGTGCGC

CTCACACGCACACGCGCGCTCCCCGGCTCACGCGCGCTCCGACACACACGCTCACGCGAA
----------+---------+---------+---------+---------+---------+ 660
GAGTGTGCGTGTGCGCGCGAGGGGCCGAGTGCGCGCGAGGCTGTGTGTGCGAGTGCGCTT

CGCAGGCGCACGCTCTGGCGCGGGAGGCGCCCCTTCGCCTCCGTGTTGGGAAGCGGGGGC
----------+---------+---------+---------+---------+---------+ 720
GCGTCCGCGTGCGAGACCGCGCCCTCCGCGGGGAAGCGGAGGCACAACCCTTCGCCCCCG

GGCGGGAGGGGCAGGAGACGTTGGCCCCGCTCGCGTTTCTGCAGCTGCTGCAGTCGCCGC
----------+---------+---------+---------+---------+---------+ 780
CCGCCCTCCCCGTCCTCTGCAACCGGGGCGAGCGCAAAGACGTCGACGACGTCAGCGGCG

AGCGTCCGGACCGGAACCAGCGCCGTCCGCGGAGCCGCCGCCGCCGCCGGGCCCTTT
----------+---------+---------+---------+---------+---------+ 840
TCGCAGGCCTGGCCTTGGTCGCGGCAGGCGCCTCGGCGGCGGCGGCGGCCCGGGAAA

CCAAGCCGGGCGCTCGGAGCTGTGCCCGGCCCCGCTTCAGCACCGCGGACAGCTCCGGCC
----------+---------+---------+---------+---------+---------+ 900
GGTTCGGCCCGCGAGCCTCGACACGGGCCGGGGCGAAGTCGTGGCGCCTGTCGAGGCCGG
```

FIG. 1A

```
GCGTGGGGCTGAGCCGAGCCCCCGCGCACGCTTCAGCCCCCTTCCCTCGGCCGACGTCCC
----------+---------+---------+---------+---------+---------+    960
CGCACCCCGACTCGGCTCGGGGGCGCGTGCGAAGTCGGGGGAAGGGAGCCGGCTGCAGGG

GGGACCGCCGCTCCGGGGGAGACGTGGCGTCCGCAGCCCGCGGGGCCGGGCGAGCGCAGG
----------+---------+---------+---------+---------+---------+   1020
CCCTGGCGGCGAGGCCCCCTCTGCACCGCAGGCGTCGGGCGCCCCGGCCCGCTCGCGTCC

ACGGCCCGGAAGCCCCGCGGGGGATGCGCCGAGGGCCCGCGTTCGCGCCGCGCAGAGCCA
----------+---------+---------+---------+---------+---------+   1080
TGCCGGGCCTTCGGGGCGCCCCCTACGCGGCTCCCGGGCGCAAGCGCGGCGCGTCTCGGT

|---------------signal-peptide---------------
                          M  S  T  M  R  L  L  T  L  A  L  L  F  S     -4
GGCCCGCGGCCCGAGCCCATGAGCACCATGCGCCTGCTGACGCTCGCCCTGCTGTTCTCC
----------+---------+---------+---------+---------+---------+   1140
CCGGGCGCCGGGCTCGGGTACTCGTGGTACGCGGACGACTGCGAGCGGGACGACAAGAGG
-----------|
 C  S  V  A  R  A  A  C  D  P  K  I  V  N  I  G  A  V  L  S      16
TGCTCCGTCGCCCGTGCCGCGTGCGACCCCAAGATCGTCAACATTGGCGCGGTGCTGAGC
----------+---------+---------+---------+---------+---------+   1200
ACGAGGCAGCGGGCACGGCGCACGCTGGGGTTCTAGCAGTTGTAACCGCGCCACGACTCG T  R  K  H  E  Q  M  F  R  E  A  V  N  Q  A  N  K  R  H  G      36
ACGCGGAAGCACGAGCAGATGTTCCGCGAGGCCGTGAACCAGGCCAACAAGCGGCACGGC
----------+---------+---------+---------+---------+---------+   1260
TGCGCCTTCGTGCTCGTCTACAAGGCGCTCCGGCACTTGGTCCGGTTGTTCGCCGTGCCG S  W  K  I  Q  L  N  A  T  S  V  T  H  K  P  N  A  I  Q  M      56
TCCTGGAAGATTCAGCTCAATGCCACCTCCGTCACGCACAAGCCCAACGCCATCCAGATG
----------+---------+---------+---------+---------+---------+   1320
AGGACCTTCTAAGTCGAGTTACGGTGGAGGCAGTGCGTGTTCGGGTTGCGGTAGGTCTAC A  L  S  V  C  E  D  L  I  S  S  Q  V  Y  A  I  L  V  S  H      76
GCTCTGTCGGTGTGCGAGGACCTCATCTCCAGCCAGGTCTACGCCATCCTAGTTAGCCAT
----------+---------+---------+---------+---------+---------+   1380
CGAGACAGCCACACGCTCCTGGAGTAGAGGTCGGTCCAGATGCGGTAGGATCAATCGGTA P  P  T  P  N  D  H  F  T  P  T  P  V  S  Y  T  A  G  F  Y      96
CCACCTACCCCCAACGACCACTTCACTCCCACCCCTGTCTCCTACACAGCCGGCTTCTAC
----------+---------+---------+---------+---------+---------+   1440
GGTGGATGGGGGTTGCTGGTGAAGTGAGGGTGGGGACAGAGGATGTGTCGGCCGAAGATG R  I  P  V  L  G  L  T  T  R  M  S  I  Y  S  D  K  S  I  H     116
CGCATACCCGTGCTGGGCTGACCACCCGCATGTCCATCTACTCGGACAAGAGCATCCAC
----------+---------+---------+---------+---------+---------+   1500
GCGTATGGGCACGACCCGACTGGTGGGCGTACAGGTAGATGAGCCTGTTCTCGTAGGTG L  S  F  L  R  T  V  P  P  Y  S  H  Q  S  S  V  W  F  E  M     136
CTGAGCTTCCTGCGCACCGTGCCGCCCTACTCCCACCAGTCCAGCGTGTGGTTTGAGATG
----------+---------+---------+---------+---------+---------+   1560
GACTCGAAGGACGCGTGGCACGGCGGGATGAGGGTGGTCAGGTCGCACACCAAACTCTAC M  R  V  Y  S  W  N  H  I  I  L  L  V  S  D  D  H  E  G  R     156
ATGCGTGTCTACAGCTGGAACCACATCATCCTGCTGGTCAGCGACGACCACGAGGGCCGG
----------+---------+---------+---------+---------+---------+   1620
TACGCACAGATGTCGACCTTGGTGTAGTAGGACGACCAGTCGCTGCTGGTGCTCCCGGCC
```

FIG. 1B

```
              A  A  Q  K  R  L  E  T  L  L  E  E  R  E  S  K  A  E  K  V     176
           GCGGCTCAGAAACGCCTGGAGACGCTGCTGGAGGAGCGTGAGTCCAAGGCAGAGAAGGTG
           ----------+---------+---------+---------+---------+---------+    1680
           CGCCGAGTCTTTGCGGACCTCTGCGACGACCTCCTCGCACTCAGGTTCCGTCTCTTCCAC

L  Q  F  D  P  G  T  K  N  V  T  A  L  L  M  E  A  K  E  L     196
           CTGCAGTTTGACCCAGGGACCAAGAACGTGACGGCCCTGCTGATGGAGGCGAAAGAGCTG
           ----------+---------+---------+---------+---------+---------+    1740
           GACGTCAAACTGGGTCCCTGGTTCTTGCACTGCCGGGACGACTACCTCCGCTTTCTCGAC

E  A  R  V  I  I  L  S  A  S  E  D  D  A  A  T  V  Y  R  A     216
           GAGGCCCGGGTCATCATCCTTTCTGCCAGCGAGGACGATGCTGCCACTGTATACCGCGCA
           ----------+---------+---------+---------+---------+---------+    1800
           CTCCGGGCCCAGTAGTAGGAAAGACGGTCGCTCCTGCTACGACGGTGACATATGGCGCGT
                                                                Bgl II
              A  A  M  L  N  M  T  G  S  G  Y  V  W  L  V  G  E  R  E  I     236
           GCCGCGATGCTGAACATGACGGGCTCCGGGTACGTGTGGCTGGTCGGCGAGCGCGAGATC
           ----------+---------+---------+---------+---------+---------+    1860
           CGGCGCTACGACTTGTACTGCCCGAGGCCCATGCACACCGACCAGCCGCTCGCGCTCTAG

S  G  N  A  L  R  Y  A  P  D  G  I  L  G  L  Q  L  I  N  G     256
           TCGGGGAACGCCCTGCGCTACGCCCCAGACGGCATCCTCGGGCTGCAGCTCATCAACGGC
           ----------+---------+---------+---------+---------+---------+    1920
           AGCCCCTTGCGGGACGCGATGCGGGGTCTGCCGTAGGAGCCCGACGTCGAGTAGTTGCCG

K  N  E  S  A  H  I  S  D  A  V  G  V  V  A  Q  A  V  H  E     276
           AAGAACGAGTCGGCCCACATCAGCGACGCCGTGGGCGTGGTGGCCCAGGCCGTGCACGAG
           ----------+---------+---------+---------+---------+---------+    1980
           TTCTTGCTCAGCCGGGTGTAGTCGCTGCGGCACCCGCACCACCGGGTCCGGCACGTGCTC

L  L  E  K  N  I  T  D  P  P  R  G  C  V  G  N  T  N  I       296
           CTCCTCGAGAAGGAGAACATCACCGACCCGCCGCGGGGCTGCGTGGGCAACACCAACATC
           ----------+---------+---------+---------+---------+---------+    2040
           GAGGAGCTCTTCCTCTTGTAGTGGCTGGGCGGCGCCCCGACGCACCCGTTGTGGTTGTAG

W  K  T  G  P  L  F  K  R  V  L  M  S  S  K  Y  A  D  G  V     316
           TGGAAGACCGGGCCGCTCTTCAAGAGAGTGCTGATGTCTTCCAAGTATGCGGATGGGGTG
           ----------+---------+---------+---------+---------+---------+    2100
           ACCTTCTGGCCCGGCGAGAAGTTCTCTCACGACTACAGAAGGTTCATACGCCTACCCCAC

T  G  R  V  E  F  N  E  D  G  D  R  K  F  A  N  Y  S  I  M     336
           ACTGGTCGCGTGGAGTTCAATGAGGATGGGGACCGGAAGTTCGCCAACTACAGCATCATG
           ----------+---------+---------+---------+---------+---------+    2160
           TGACCAGCGCACCTCAAGTTACTCCTACCCCTGGCCTTCAAGCGGTTGATGTCGTAGTAC

N  L  Q  N  R  K  L  V  Q  V  G  I  Y  N  G  T  H  V  I  P     356
           AACCTGCAGAACCGCAAGCTGGTGCAAGTGGGCATCTACAATGGCACCCACGTCATCCCT
           ----------+---------+---------+---------+---------+---------+    2220
           TTGGACGTCTTGGCGTTCGACCACGTTCACCCGTAGATGTTACCGTGGGTGCAGTAGGGA

N  D  R  K  I  I  W  P  G  G  E  T  E  K  P  R  G  Y  Q  M     376
           AATGACAGGAAGATCATCTGGCCAGGCGGAGAGACAGAGAAGCCTCGAGGGTACCAGATG
           ----------+---------+---------+---------+---------+---------+    2280
           TTACTGTCCTTCTAGTAGACCGGTCCGCCTCTCTGTCTCTTCGGAGCTCCCATGGTCTAC

S  T  R  L  K  I  V  T  I  H  Q  E  P  F  V  Y  V  K  P  T     396
           TCCACCAGACTGAAGATTGTGACGATCCACCAGGAGCCCTTCGTGTACGTCAAGCCCACG
           ----------+---------+---------+---------+---------+---------+    2340
           AGGTGGTCTGACTTCTAACACTGCTAGGTGGTCCTCGGGAAGCACATGCAGTTCGGGTGC
```

FIG. 1C

```
           L   S   D   G   T   C   K   E   E   F   T   V   N   G   D   P   V   K   K   V      416
        CTGAGTGATGGGACATGCAAGGAGGAGTTCACAGTCAACGGCGACCCAGTCAAGAAGGTG
        ---------+---------+---------+---------+---------+---------+   2400
        GACTCACTACCCTGTACGTTCCTCCTCAAGTGTCAGTTGCCGCTGGGTCAGTTCTTCCAC

I   C   T   G   P   N   D   T   S   P   G   S   P   R   H   T   V   P   Q   C      436
        ATCTGCACCGGGCCCAACGACACGTCGCCGGGCAGCCCCCGCCACACGGTGCCTCAGTGT
        ---------+---------+---------+---------+---------+---------+   2460
        TAGACGTGGCCCGGGTTGCTGTGCAGCGGCCCGTCGGGGGCGGTGTGCCACGGAGTCACA

C   Y   G   F   C   I   D   L   L   I   K   L   A   R   T   M   N   F   T   Y      456
        TGCTACGGCTTTTGCATCGACCTGCTCATCAAGCTGGCACGGACCATGAACTTCACCTAC
        ---------+---------+---------+---------+---------+---------+   2520
        ACGATGCCGAAAACGTAGCTGGACGAGTAGTTCGACCGTGCCTGGTACTTGAAGTGGATG

E   V   H   L   V   A   D   G   K   F   G   T   Q   E   R   V   N   N   S   N      476
        GAGGTGCACCTGGTGGCAGATGGCAAGTTCGGCACACAGGAGCGGGTGAACAACAGCAAC
        ---------+---------+---------+---------+---------+---------+   2580
        CTCCACGTGGACCACCGTCTACCGTTCAAGCCGTGTGTCCTCGCCCACTTGTTGTCGTTG

K   K   E   W   N   G   M   M   G   E   L   L   S   G   Q   A   D   M   I   V      496
        AAGAAGGAGTGGAATGGGATGATGGGCGAGCTGCTCAGCGGGCAGGCAGACATGATCGTG
        ---------+---------+---------+---------+---------+---------+   2640
        TTCTTCCTCACCTTACCCTACTACCCGCTCGACGAGTCGCCCGTCCGTCTGTACTAGCAC

A   P   L   T   I   N   N   E   R   A   Q   Y   I   E   F   S   K   P   F   K      516
        GCGCCGCTAACCATAAACAACGAGCGCGCGCAGTACATCGAGTTTTCCAAGCCCTTCAAG
        ---------+---------+---------+---------+---------+---------+   2700
        CGCGGCGATTGGTATTTGTTGCTCGCGCGCGTCATGTAGCTCAAAAGGTTCGGGAAGTTC

Y   Q   G   L   T   I   L   V   K   K   E   I   P   R   S   T   L   D   S   F      536
        TACCAGGGCCTGACTATTCTGGTCAAGAAGGAGATTCCCCGGAGCACGCTGGACTCGTTC
        ---------+---------+---------+---------+---------+---------+   2760
        ATGGTCCCGGACTGATAAGACCAGTTCTTCCTCTAAGGGGCCTCGTGCGACCTGAGCAAG

|------------------TM-1----------------
           M   Q   P   F   Q   S   T   L   W   L   L   V   G   L   S   V   H   V   V   A      556
        ATGCAGCCGTTCCAGAGCACACTGTGGCTGCTGGTGGGGCTGTCGGTGCACGTGGTGGCC
        ---------+---------+---------+---------+---------+---------+   2820
        TACGTCGGCAAGGTCTCGTGTGACACCGACGACCACCCCGACAGCCACGTGCACCACCGG

----------------|
           V   M   L   Y   L   L   D   R   F   S   P   F   G   R   F   K   V   N   S   E      576
        GTGATGCTGTACCTGCTGGACCGCTTCAGCCCCTTCGGCCGGTTCAAGGTGAACAGCGAG
        ---------+---------+---------+---------+---------+---------+   2880
        CACTACGACATGGACGACCTGGCGAAGTCGGGGAAGCCGGCCAAGTTCCACTTGTCGCTC

|-------------------TM-2-----------------
           E   E   E   E   D   A   L   T   L   S   S   A   M   W   F   S   W   G   V   L      596
        GAGGAGGAGGAGGACGCACTGACCCTGTCCTCGGCCATGTGGTTCTCCTGGGGCGTCCTG
        ---------+---------+---------+---------+---------+---------+   2940
        CTCCTCCTCCTCCTGCGTGACTGGGACAGGAGCCGGTACACCAAGAGGACCCCGCAGGAC

----------------|                                        |------------
           L   N   S   G   I   G   E   G   A   P   R   S   F   S   A   R   I   L   G   M      616
        CTCAACTCCGGCATCGGGGAAGGCGCCCCCAGAAGCTTCTCAGCGCGCATCCTGGGCATG
        ---------+---------+---------+---------+---------+---------+   3000
        GAGTTGAGGCCGTAGCCCCTTCCGCGGGGGTCTTCGAAGAGTCGCGCGTAGGACCCGTAC
```

FIG. 1D

```
--------TM-3----------------------------------|
  V   W   A   G   F   A   M   I   I   V   A   S   Y   T   A   N   L   A   A   F       636
GTGTGGGCCGGCTTTGCCATGATCATCGTGGCCTCCTACACCGCCAACCTGGCGGCCTTC
---------+---------+---------+---------+---------+---------+                         3060
CACACCCGGCCGAAACGGTACTAGTAGCACCGGAGGATGTGGCGGTTGGACCGCCGGAAG

L   V   L   D   R   P   E   E   R   I   T   G   I   N   D   P   R   L   R   N       656
CTGGTGCTGGACCGGCCGGAGGAGCGCATCACGGGCATCAACGACCCTCGGCTGAGGAAC
---------+---------+---------+---------+---------+---------+                         3120
GACCACGACCTGGCCGGCCTCCTCGCGTAGTGCCCGTAGTTGCTGGGAGCCGACTCCTTG

P   S   D   K   F   I   Y   A   T   V   K   Q   S   S   V   D   I   Y   F   R       676
CCCTCGGACAAGTTTATCTACGCCACGGTGAAGCAGAGCTCCGTGGATATCTACTTCCGG
---------+---------+---------+---------+---------+---------+                         3180
GGGAGCCTGTTCAAATAGATGCGGTGCCACTTCGTCTCGAGGCACCTATAGATGAAGGCC

R   Q   V   E   L   S   T   M   Y   R   H   M   E   K   H   N   Y   E   S   A       696
CGCCAGGTGGAGCTGAGCACCATGTACCGGCATATGGAGAAGCACAACTACGAGAGTGCG
---------+---------+---------+---------+---------+---------+                         3240
GCGGTCCACCTCGACTCGTGGTACATGGCCGTATACCTCTTCGTGTTGATGCTCTCACGC

A   E   A   I   Q   A   V   R   D   N   K   L   H   A   F   I   W   D   S   A       716
GCGGAGGCCATCCAGGCCGTGAGAGACAACAAGCTGCATGCCTTCATCTGGGACTCGGCG
---------+---------+---------+---------+---------+---------+                         3300
CGCCTCCGGTAGGTCCGGCACTCTCTGTTGTTCGACGTACGGAAGTAGACCCTGAGCCGC

V   L   E   F   E   A   S   Q   K   C   D   L   V   T   T   G   E   L   F   F       736
GTGCTGGAGTTCGAGGCCTCGCAGAAGTGCGACCTGGTGACGACTGGAGAGCTGTTTTTC
---------+---------+---------+---------+---------+---------+                         3360
CACGACCTCAAGCTCCGGAGCGTCTTCACGCTGGACCACTGCTGACCTCTCGACAAAAAG

R   S   G   F   G   I   G   M   R   K   D   S   P   W   K   Q   N   V   S   L       756
CGCTCGGGCTTCGGCATAGGCATGCGCAAAGACAGCCCCTGGAAGCAGAACGTCTCCCTG
---------+---------+---------+---------+---------+---------+                         3420
GCGAGCCCGAAGCCGTATCCGTACGCGTTTCTGTCGGGGACCTTCGTCTTGCAGAGGGAC

S   I   L   K   S   H   E   N   G   F   M   E   D   L   D   K   T   W   V   R       776
TCCATCCTCAAGTCCCACGAGAATGGCTTCATGGAAGACCTGGACAAGACGTGGGTTCGG
---------+---------+---------+---------+---------+---------+                         3480
AGGTAGGAGTTCAGGGTGCTCTTACCGAAGTACCTTCTGGACCTGTTCTGCACCCAAGCC

|------
  Y   Q   E   C   D   S   R   S   N   A   P   A   T   L   T   F   E   N   M   A       796
TATCAGGAATGTGACTCGCGCAGCAACGCCCCTGCGACCCTTACTTTTGAGAACATGGCC
---------+---------+---------+---------+---------+---------+                         3540
ATAGTCCTTACACTGAGCGCGTCGTTGCGGGGACGCTGGGAATGAAAACTCTTGTACCGG

--------------------TM-4----------------------------------|
  G   V   F   M   L   V   A   G   G   I   V   A   G   I   F   L   I   F   I   E       816
GGGGTCTTCATGCTGGTAGCTGGGGGCATCGTGGCCGGGATCTTCCTGATTTTCATCGAG
---------+---------+---------+---------+---------+---------+                         3600
CCCCAGAAGTACGACCATCGACCCCCGTAGCACCGGCCCTAGAAGGACTAAAAGTAGCTC

I   A   Y   K   R   H   K   D   A   R   R   K   Q   M   Q   L   A   F   A   A       836
ATTGCCTACAAGCGGCACAAGGATGCTCGCCGGAAGCAGATGCAGCTGGCCTTTGCCGCC
---------+---------+---------+---------+---------+---------+                         3660
TAACGGATGTTCGCCGTGTTCCTACGAGCGGCCTTCGTCTACGTCGACCGGAAACGGCGG

V   N   V   W   R   K   N   L   Q   Q   Y   H   P   T   D   I   T   G   P   L       856
GTTAACGTGTGGCGGAAGAACCTGCAGCAGTACCATCCCACTGATATCACGGGCCCGCTC
---------+---------+---------+---------+---------+---------+                         3720
CAATTGCACACCGCCTTCTTGGACGTCGTCATGGTAGGGTGACTATAGTGCCCGGGCGAG
```

FIG. 1E

```
          N  L  S  D  P  S  V  S  T  V  V
AACCTCTCAGATCCCTCGGTCAGCACCGTGGTGTGAGGCCCCCGGAGGCGCCCACCTGCC                867
----------+----------+----------+----------+----------+----------+          3780
TTGGAGAGTCTAGGGAGCCAGTCGTGGCACCACACTCCGGGGGCCTCCGCGGGTGGACGG

CAGTTAGCCCGGCCAAGGACACTGATGGGTCCTGCTGCTCGGGAAGGCCTGAGGGAAGCC
----------+----------+----------+----------+----------+----------+          3840
GTCAATCGGGCCGGTTCCTGTGACTACCCAGGACGACGAGCCCTTCCGGACTCCCTTCGG

CACCCGCCCCAGAGACTGCCCACCCTGGGCCTCCCGTCCGTCCGCCCGCCCACCCCGCTG
----------+----------+----------+----------+----------+----------+          3900
GTGGGCGGGGTCTCTGACGGGTGGGACCCGGAGGGCAGGCAGGCGGGCGGGTGGGGCGAC

CCTGGCGGGCAGCCCCTGCTGGACCAAGGTGCGGACCGGAGCGGCTGAGGACGGGGCAGA
----------+----------+----------+----------+----------+----------+          3960
GGACCGCCCGTCGGGGACGACCTGGTTCCACGCCTGGCCTCGCCGACTCCTGCCCCGTCT

GCTCAGTCGGCTGGGCAGGGCGCAGGGCGCTCCGGCAGAGGCAGGGCCCTGGGGTCTCTG
----------+----------+----------+----------+----------+----------+          4020
CGACTCAGCCGACCCGTCCCGCGTCCCGCGAGGCCGTCTCCGTCCCGGGACCCCAGAGAC

AGCAGTGGGGAGCGGGGGCTAACTGGCCCCAGGCGAAGGGGCTTGGAGCAGAGACGGCAG
----------+----------+----------+----------+----------+----------+          4080
TCGTCACCCCTCGCCCCCGATTGACCGGGGTCCGCTTCCCCGAACCTCGTCTCTGCCGTC

CCCCATCCTTCCCGCAGCACCAGCCTGAGCCACAGTGGGGCCCATGGCCCCAGCTGGCTG
----------+----------+----------+----------+----------+----------+          4140
GGGGTAGGAAGGGCGTCGTGGTCGGACTCGGTGTCACCCCGGGTACCGGGGTCGACCGAC

GGTCGCCCCTCCTCGGGCGCCTGCGCTCCTCTGCAGCCTGAGCTCCACCCTCCCCTCTTC
----------+----------+----------+----------+----------+----------+          4200
CCAGCGGGGAGGAGCCCGCGGACGCGAGGAGACGTCGGACTCGAGGTGGGAGGGGAGAAG

TTGCGGCACCGCCCACCCACACCCCGTCTGCCCCTTGACCCCACACGCCGGGGCTGGCCC
----------+----------+----------+----------+----------+----------+          4260
AACGCCGTGGCGGGTGGGTGTGGGCAGACGGGGAACTGGGGTGTGCGGCCCCGACCGGG

TGCCCTCCCCCACGGCCGTCCCTGACTTCCCAGCTGGCAGCGCCTCCCGCCGCCTCGGGC
----------+----------+----------+----------+----------+----------+          4320
ACGGGAGGGGGTGCCGGCAGGGACTGAAGGGTCGACCGTCGCGGAGGGCGGCGGAGCCCG

CGCCTCCTCCAGACTCGAGAGGGCTGAGCCCCTCCTCTCCTCGTCCGGCCTGCAGCCCAG
----------+----------+----------+----------+----------+----------+          4380
GCGGAGGAGGTCTGAGCTCTCCCGACTCGGGGAGGAGAGGAGCAGGCCGGACGTCGGGTC

AACGGGCCTCCCCGGGGGTCCCCGGACGCTGGCTCGGGACTGTCTTCAACCCTGCCCTGC
----------+----------+----------+----------+----------+----------+          4440
TTGCCCGGAGGGGCCCCCAGGGGCCTGCGACCGAGCCCTGACAGAAGTTGGGACGGGACG

ACCTTGGGCACGGGAGAGCGCCACCCGCCCGCCCCCGCCCTCGCTCCGGGTGCGTGACCG
----------+----------+----------+----------+----------+----------+          4500
TGGAACCCGTGCCCTCTCGCGGTGGGCGGGCGGGGCGGGAGCGAGGCCCACGCACTGGC

GCCCGCCACCTTGTACAGAACCAGCACTCCCAGGGCCCGAGCGCGTGCCTTCCCCGTGCG
----------+----------+----------+----------+----------+----------+          4560
CGGGCGGTGGAACATGTCTTGGTCGTGAGGGTCCCGGGCTCGCGCACGGAAGGGGCACGC

GCCCGTGCGCAGCCGCGCTCTGCCCCTCCGTCCCCAGGGTGCAGGCGCGCACCGCCCAAC
----------+----------+----------+----------+----------+----------+          4620
CGGGCACGCGTCGGCGCGAGACGGGGAGGCAGGGGTCCCACGTCCGCGCGTGGCGGGTTG
                                          Eco RI
CCCCACCTCCCGGTGTATGCAGTGGTGATGCCGGAATTC
----------+----------+----------+--------                                    4659
GGGGTGGAGGGCCACATACGTCACCACTACGGCCTTAAG
```

FIG. 1F

```
3675 GAAGAACCTGCAG............................................ 3687  1
3675 GAAGAACCTGCAG............................................ 3687  2
3675 GAAGAACCTGCAGGATAGAAAGAGTGGTAGAGCAGAGCCTGACCCTAAAAAGAAAGCCAC +47  3A
3675 GAAGAACCTGCAGGATAGAAAGAGTGGTAGAGCAGAGCCTGACCCTAAAAAGAAAGCCAC +47  3C

...........................................................        1
                                                                         2
     ATTTAGGGCTATCACCTCCACCCTGGCTTCCAGCTTCAAGAGGCGTAGGTCCTCCAAAGA +107 3A
     ATTTAGGGCTATCACCTCCACCCTGGCTTCCAGCTTCAAGAGGCGTAGGTCCTCCAAAGA +107 3C

....AGCACCGGGGGTGGACGCGGCGCTTTGCAAAACCAAAAAGACACAGTGCTGCCGCG +56   1
                                                                         2
     CACGAGCACCGGGGGTGGACGCGGCGCTTTGCAAAACCAAAAAGACACAGTGCTGCCGCG +167 3A
     CACGAGCACCGGGGGTGGACGCGGCGCTTTGCAAAACCAAAAAGACACAGTGCTGCCGCG +167 3C

ACGCGCTATTGAGAGGGAGGAGGGCCAGCTGCAGCTGTGTTCCCGTCATAGGGAGAGCTG +116  1
                                                                         2
     ACGCGCTATTGAGAGGGAGGAGGGCCAGCTGCAGCTGTGTTCCCGTCATAGGGAGAGCTG +227 3A
     ACGCGCTATTGAGAGGGAGGAGGGCCAGCTGCAGCTGTGTTCCCGTCATACGGAGAGCTG +227 3C
                                                        *    END

AGACTCCCCGCCCGCCCTCCTCTGCCCCCTCCCCCGCAGACAGACAGACAGACGGATGGG +176  1
                                                                         2
     AGACTCCCCGCCCGCCCTCCTCTGCCCCCTCCCCCGCAGACAGACAGACAGACGGATGGG +287 3A
     AGACTCCCCGCCCGCCCTCCTCTGCCCCCTCCCCCGCAGACAGACAGACAGACGGATGGG +287 3C

ACAGCGGCCCGGCCCACGCAGAGCCCCGGAGCACCACGGGGTCGGGGGAGGAGCACCCCC +236  1
                                                                         2
     ACAGCGGCCCGGCCCACGCAGAGCCCCGGAGCACCACGGGGTCGGGGGAGGAGCACCCCC +347 3A
     ACAGCGGCCCGGCCCACGCAGAGCCCCGGAGCACCACGGGGTCGGGGGAGGAGCACCCCC +347 3C

AGCCTCCCCCAGGCTGCGCCTGCCCGCCCGCCGGTTGGCCGGCTGGCCGGTCCACCCCGT +296  1
                                                                         2
     AGCCTCCCCCAGGCTGCGCCTGCCCGCCCGCCGGTTGGCCGGCTGGCCGGTCCACCCCGT +407 3A
     AGCCTCCCCCAGGCTGCGCCTGCCCGCCCGCCGGTTGGCCGGCTGGCCGGTCCACCCCGT +407 3C

CCCGGCCCCGCGCGTGCCCCCAGCGTGGGGCTAACGGGCGCCTTGTCTGTGTATTTCTAT +356  1
                                                                         2
     CCCGGCCCCGCGCGTGCCCCCAGCGTGGGGCTAACGGGCGCCTTGTCTGTGTATTTCTAT +467 3A
     CCCGGCCCCGCGCGTGCCCCCAGCGTGGGGCTAACGGGCGCCTTGTCTGTGTATTTCTAT +467 3C

3688 .......CAGTACCATCCCACT 3702 humNMDAR1-1
+357 TTTGCAGCAGTACCATCCCACT 4065 humNMDAR1-2
+468 TTTGCAGCAGTACCATCCCACT 4176 humNMDAR1-3A
+468 TTTGCAGCAGTACCATCCCACT 4176 humNMDAR1-3C
```

FIG. 3A

```
      TM4
803 AGGIVAGIFLIFIEIAYKRHKDARRKQMQLAFAAVNVWRKNLQQYHPTDITGPLNLSDPS 862  1
    |||||||||||||||||||||||||||||||||||||||||||||||
803 AGGIVAGIFLIFIEIAYKRHKDARRKQMQLAFAAVNVWRKNLQ................. 845  2
    ||||||||||||||||||||||||||||||||||||||||||
803 AGGIVAGIFLIFIEIAYKRHKDARRKQMQLAFAAVNVWRKNLQDRKSGRAEPDPKKKATF 862  3A
    |||||||||||||||||||||||||||||||||||||||||||||||||||||||||||
803 AGGIVAGIFLIFIEIAYKRHKDARRKQMQLAFAAVNVWRKNLQDRKSGRAEPDPKKKATF 862  3C

VSTVV                      .      .      .      .      .      867  1
.................STGGGRGALQNQKDTVLPRRAIEREEGQLQLCSRHRES 883  2
RAITSTLASSFKRRRSSKDTSTGGGRGALQNQKDTVLPRRAIEREEGQLQLCSRHRES 920  3A
RAITSTLASSFKRRRSSKDTSTGGGRGALQNQKDTVLPRRAIEREEGQLQLCSRHTES 920  3C
                                                        *
```

FIG. 3B

```
                    humNMDAR1-1/humNMDAR1-3C
 462    A   D   G   K   F   G   T   Q   E   R   V   N   N   S   N   K   K   E   W    481
2534  TGGCAGATGGCAAGTTCGGCACACAGGAGCGGGTGAACAACAGCAACAAGAAGGAGTGGA  2593
      ||||||||||||||||||||||||||||| ||||||||||||||||||||||||||||||
2534  TGGCAGATGGCAAGTTCGGCACACAGAAGCGGGTGAACAACAGCAACAAGAAGGAGTGGA  2593
 462    A   D   G   K   F   G   T   Q   K   R   V   N   N   S   N   K   K   E   W    481
                            humNMDAR1-3B
```

FIG. 4

```
3675  GAAGAACCTGCAG...................................... 3687   1
      |||||||||||||
3675  GAAGAACCTGCAGGATAGAAAGAGTGGTAGAGCAGAGCCTGACCCTAAAAAGAAAGCCAC  +47   4

1
 +48  ATTTAGGGCTATCACCTCCACCCTGGCTTCCAGCTTCAAGAGGCGTAGGTCCTCCAAAGA +107  4

3688  ....CAGTACCATCCCACT   3702  humNMDAR1-1
          |||||||||||||||
+108  CACGCAGTACCATCCCACT   3813  humNMDAR1-4
```

FIG. 5A

```
       TM4
803  AGGIVAGIFLIFIEIAYKRHKDARRKQMQLAFAAVNVWRKNLQ.............. 845  1
     ||||||||||||||||||||||||||||||||||||||||||
803  AGGIVAGIFLIFIEIAYKRHKDARRKQMQLAFAAVNVWRKNLQDRKSGRAEPDPKKKATF 862  4

846  ..................QYHPTDITGPLNLSDPSVSTVV  867  humNMDAR1-1
                       ||||||||||||||||||||||
863  RAITSTLASSFKRRRSSKDTQYHPTDITGPLNLSDPSVSTVV  904  humNMDAR1-4
```

FIG. 5B

```
1649 TGGAGGAGCGTGAGTCCAAGAGTAAAAAAAGGAACTATGAAAACCTCGAC   +35   5,6,7,8
1649 TGGAGGAGCGTGAGT...................................  1663  1,2,3,4

+36 CAACTGTCCTATGACAACAAGCGCGGACCCAAGGCAGAGAAGGTGCTGCA  1748  humNMDAR1-5 to 1-8
1664 .........................CCAAGGCAGAGAAGGTGCTGCA    1685  humNMDAR1-1 to 1-4
```

FIG. 6A

```
160 KRLETLLEERESKSKKRNYENLDQLSYDNKRGPKAEKVLQFDPGTKN    206   humNMDAR1-5 to 1-8
160 KRLETLLEERESK....................AEKVLQFDPGTKN    185   humNMDAR1-1 to 1-4
```

FIG. 6B

HUMAN CNS RECEPTORS OF THE NMDA-R1 FAMILY

This application is a continuation-in-part of U.S. Ser. No. 07/987,953 filed Dec. 11, 1992, now abandoned which is herein incorporated by reference in its entirety.

FIELD OF THE INVENTION

This invention is concerned with applications of recombinant DNA technology in the field of neurobiology. More particularly, the invention relates to the cloning and expression of DNA coding for excitatory amino acid (EAA) receptors, especially human EAA receptors.

BACKGROUND TO THE INVENTION

In the mammalian central nervous system (CNS), the transmission of nerve impulses is controlled by the interaction between a neurotransmitter substance released by the "sending" neuron which then binds to a surface receptor on the "receiving" neuron, to cause excitation thereof. L-glutamate is the most abundant neurotransmitter in the CNS, and mediates the major excitatory pathway in vertebrates. Glutamate is therefore referred to as an excitatory amino acid (EAA) and the receptors which respond to it are variously referred to as glutamate receptors, or more commonly as EAA receptors.

Using tissues isolated from mammalian brain, and various synthetic EAA receptor agonists, knowledge of EAA receptor pharmacology has been refined somewhat. Members of the EAA receptor family can be grouped into three main types based on differential binding to such agonists. One type of EAA receptor, which in addition to glutamate also binds the agonist NMDA (N-methyl-D-aspartate), is referred to as the NMDA type of EAA receptor. Two other glutamate-binding types of EAA receptor, which do not bind NMDA, are named according to their preference for binding with two other EAA receptor agonists, namely AMPA (alpha-amino-3-hydroxy-5-methyl-isoxazole-4-propionate), and kainate (2-carboxy-4-(1-methylethenyl)-3-pyrrolidineacetate). Accordingly, receptors which bind glutamate but not NMDA, and which bind with greater affinity to kainate than to AMPA, are referred to as kainate type EAA receptors. Similarly, those EAA receptors which bind glutamate but not NMDA, and which bind AMPA with greater affinity than kainate are referred to as AMPA type EAA receptors.

The glutamate-binding EAA receptor family is of great physiological and medical importance. Glutamate is involved in many aspects of long-term potentiation (learning and memory), in the development of synaptic plasticity, in epileptic seizures, in neuronal damage caused by ischemia following stroke or other hypoxic events, as well as in other forms of neurodegenerative processes. The development of therapeutics which modulate these processes has been very difficult, due to the lack of any homogeneous source of receptor material with which to discover selectively binding drug molecules, which interact specifically at the interface of the EAA receptor. The brain derived tissues currently used to screen candidate drugs are heterogeneous receptor sources, possessing on their surface many receptor types which interfere with studies of the EAA receptor/ligand interface of interest. The search for human therapeutics is further complicated by the limited availability of brain tissue of human origin. It would therefore be desirable to obtain cells that are genetically engineered to produce only the receptor of interest. With cell lines expressing cloned receptor cDNA, a substrate which is homogeneous for the desired receptor is provided, for drug screening programs.

Non-human cDNAs which appear to encode the NMDA-type of EAA receptor have recently been identified and isolated. A cDNA encoding a subunit polypeptide of an NMDA receptor in rat, designated NR1, has been isolated as described by Moriyoshi et al. in Nature 354: 31, 1991. This work has been extended to demonstrate six isoforms of NR1, presumably generated by combinations of alternative RNA splicing in the amino- and carboxy-terminal regions of NR1 (Anantharam et al. FEBS Lett. 305: 27, 1992; Durand et al. Proc. Natl. Acad. Sci. USA 89: 9359, 1992; Nakanishi et al. Proc. Natl. Acad. Sci. USA 89: 8552, 1992; Sugihara et al. Biochem. Biophys. Res. Commun. 185: 826, 1992). DNA encoding NR1 and one of its isoforms have also been cloned from mouse brain by Yamazaki et al. as described in FEBS Lett. 300: 39, 1992. Other rat NMDA receptor subunits, designated NR2A, NR2B and NR2C, have also been identified (Monyer et al. Science 256: 1217, 1992), as well as mouse NMDA receptor subunits which have been designated $\epsilon1$, $\epsilon2$ and $\epsilon3$ (Meguro et al. Nature 357: 70, 1992 and Kutsuwada et al. Nature 358: 36, 1992).

There has emerged from these molecular cloning advances, a better understanding of the structural features of NMDA receptors and their subunits, as they exist in the non-human brain. According to the current model, each NMDA receptor is heteromeric, consisting of individual membrane-anchored subunits, each with four transmembrane regions, and extracellular domains that dictate ligand-binding properties and contribute to the ion-gating function served by the receptor complex.

In the search for therapeutics useful to treat CNS disorders in humans, it is highly desirable to obtain knowledge of human NMDA-type EAA receptors. A specific understanding of these human receptors would provide a means to screen for compounds that react therewith, i.e. to stimulate or inhibit receptor activity, and thus providing a means to identify compounds having potential therapeutic utility in humans. Non-human mammalian models are not suitable for this purpose despite significant receptor sequence homology, as minute sequence discrepancies can cause dramatic pharmacological variation between species homologues of the same receptor (Oksenberg et al., Nature, 360:161, 1992). It is therefore particularly desirable to provide cloned cDNA encoding human EAA receptors, and cell lines expressing these receptors in a homogeneous fashion, in order to generate a screening method for compounds therapeutically useful in humans. These, accordingly, are objects of the present invention.

Another object of the present invention is to provide in isolated form a DNA molecule which codes for a human EAA receptor.

It is another object of the present invention to provide a cell that has been genetically engineered to produce an N-methyl-D-aspartate-type human EAA receptor.

SUMMARY OF THE INVENTION

Human cDNAs encoding a family of EAA receptors, which bind glutamate with an affinity typical of EAA receptors and exhibit ligand binding properties characteristic of NMDA-type EAA receptors, have been identified and characterized. A representative member of this human EAA receptor family is herein designated human NMDAR1-1. Sequence-related cDNAs encoding naturally occurring variants of the human NMDAR1-1 have also been identified, and constitute additional members of this receptor family as do fragments of NMDAR1 receptors, herein referred to as the human NMDAR1 receptor family.

The present invention thus provides, in one of its aspects, an isolated polynucleotide, consisting either of DNA or of RNA, which codes for a human NMDAR1 or for fragments thereof characterized by at least one of MK-801-binding or glutamate-binding.

In another aspect of the present invention, there is provided a cell that has been genetically engineered to produce a human EAA receptor belonging to the herein-defined NMDAR1 family. In related aspects of the present invention, there are provided recombinant DNA constructs and relevant methods useful to create such cells.

In another aspect of the present invention, there is provided a method for evaluating interaction between a test ligand and a human EAA receptor, which comprises the steps of incubating the test ligand with a genetically engineered cell of the present invention, or with a membrane preparation derived therefrom, and then assessing said interaction by determining receptor/ligand binding.

Other aspects of the present invention, which encompass various applications of the discoveries herein described, will become apparent from the following detailed description, and from the accompanying drawings in which:

BRIEF REFERENCE TO THE DRAWINGS

FIG. 1 provides the nucleotide sequence (SEQ ID NO:1) of DNA coding for an excitatory amino acid receptor of the present invention, and the deduced amino acid sequence thereof (SEQ ID NO:2);

FIGS. 3–6 show, with reference to FIG. 1, the DNA and amino acid sequences (SEQ ID NOS 3–14 and 17–24) of naturally occurring variants of the EAA receptor illustrated in FIG. 1.

DETAILED DESCRIPTION OF THE INVENTION AND ITS PREFERRED EMBODIMENTS

Figure 2:
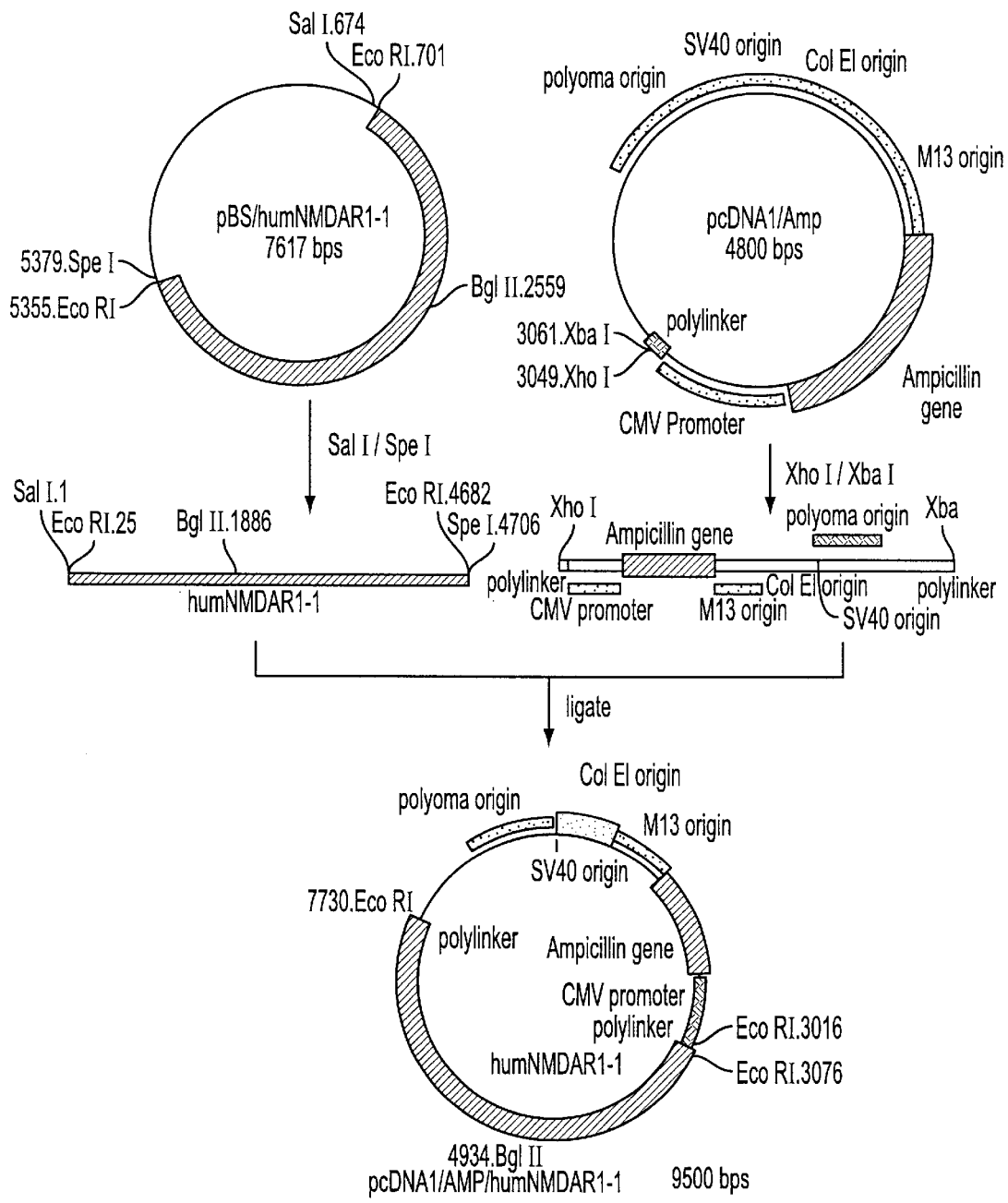
FIG. 2 illustrates with plasmid maps the strategy used to construct expression vectors harbouring the DNA sequence illustrated in FIG. 1.

The present invention relates to excitatory amino acid (EAA) receptors of human origin, and is directed more particularly to a novel family of NMDA-type human EAA receptors, herein designated the human NMDAR1 receptor family. NMDA-type human EAA receptors, generally designated herein as NMDA receptors, and including receptors of the NMDAR1 family, refer to those EAA receptors having specific binding affinity for glutamate and MK-801. NMDA is a competitive inhibitor of glutamate-binding while MK-801, the chemical formula for which is [(+)-5-methyl-10,11-dihydro-5H-dibenzo[a,d]cyclohepten-5,10-imine maleate], is a non-competitive antagonist of glutamate and has been shown to exhibit specific high-affinity binding to NMDA receptors. Consequently, NMDA receptors are characterized herein by both glutamate-binding and MK-801-binding as determined in assays of conventional design, such as the assays herein described.

As used herein, the term "human NMDAR1 receptor" "or NMDAR1" is intended to embrace the mature human NMDAR1-1 receptor which demonstrates the typical ligand binding profile of an NMDA-type receptor, i.e. specific binding affinity for NMDA, glutamate and MK-801.

Variants of the NMDAR1 receptor are included within the meaning of "human NMDAR1 receptor" as defined above and include functional variants of the mature human NMDAR1 receptor which demonstrate the same ligand binding profile as the human NMDAR1 receptor, and which are structurally related thereto, i.e. share at least 99.6% amino acid identity with the 1-845 amino acid region of the NMDAR1-1 receptor, and preferably share 100% amino acid identity in this region. There are both naturally occurring and synthetically derived variants of the human NMDAR1 receptor. Naturally occurring variants include, but are not restricted to, the receptor variants of the human NMDAR1-1 receptor herein designated human NMDAR1-2, NMDAR1-3A, NMDAR1-3B, NMDAR1-3C, NMDAR1-4, NMDAR1-5, NMDAR1-6, NMDAR1-7 and NMDAR1-8. Synthetically derived variants of the human NMDAR1 receptor include variants of the parent NMDAR1 receptors, i.e. NMDAR1-1 and the naturally occurring variants thereof, which incorporate one or more e.g. 1 to 6 amino acid substitutions, deletions or additions, relative to the parent receptor.

The term "fragment" is used herein to denote segments of an NMDAR1 receptor which exhibit at least one of glutamate-binding or MK-801-binding. Since NMDAR1 receptors display specific binding for both glutamate and MK-801, the sites for glutamate and MK-801-binding are believed to be separate and distinct sites. Thus, fragments according to the present invention may display glutamate-binding, MK-801-binding, or both glutamate- and MK-801-binding.

The term "glutamate-binding", as it is used herein with respect to NMDAR1 receptors, and variants and fragments thereof, is meant to encompass those receptors, variants and fragments that display a greater binding affinity for glutamate than for NMDA, AMPA or kainate.

Further, the term "MK-801-binding", as it is used herein with respect to NMDAR1 receptors, and variants and fragments thereof, is meant to encompass those receptors, variants and fragments that display measurable binding for MK-801, for example, binding that is at least comparable to the binding of MK-801 to the NMDAR1-1 receptor. MK-801-binding is generally in the femptomolar range; however, preferably, MK-801-binding is greater than 10 femptomoles per milligram of protein as displayed herein by the NMDAR1-1 receptor.

Each of the naturally occurring members of the human NMDAR1 receptor family possesses structural features characteristic of EAA receptors in general, including extracellular amino- and carboxy-terminal regions, as well as four internal hydrophobic domains which serve to anchor the receptor within the cell surface membrane. The particular human EAA receptor designated NMDAR1-1 is a protein characterized structurally as a single polypeptide chain that is produced initially in precursor form bearing an 18 residue amino-terminal (N-terminal) signal peptide, and is transported to the cell surface in mature form, lacking the signal peptide and consisting of 867 amino acids arranged in the sequence illustrated, by single letter code, in FIG. 1 (SEQ ID NO:2). Unless otherwise stated, the term "NMDAR1 receptor" refers to the mature form of the receptor protein, and amino acid residues of NMDAR1 receptors are accordingly numbered with reference to the mature protein sequence. With respect to structural domains of the receptor, hydropathy analysis reveals four putative transmembrane domains in NMDAR1-1, one spanning amino acid residues 544–562 inclusive (TM-1), another spanning residues 582–602 (TM-2), a third spanning residues 613–631 (TM-3) and a fourth spanning residues 795–815 (TM-4). Based on this assignment, it is likely that the human NMDAR1-1 receptor structure, in its natural membrane-bound form, consists of a 543 amino acid N-terminal extracellular domain, followed by a hydrophobic region containing four transmembrane domains and an extracellular, 52 amino acid carboxy-terminal (C-terminal) domain.

As shown in FIGS. 3 to 6, nine structurally-related variants of the NMDAR1-1 receptor (partially illustrated in SEQ ID NOS 8,9,10,12,20, and 23) have also been identified and are designated as set out above. As deduced from the cDNAs encoding these receptors, the nucleotide sequence of NMDAR1-2 (partially illustrated in SEQ ID NO:4) comprises the NMDAR1-1 nucleotide sequence and further includes a 363 bp insert between nucleotides 3687 and 3688 (FIG. 3A), SEQ ID NOS 3–6. The nucleotide sequences of NMDAR1-3A (partially illustrated in SEQ ID NO:54), NMDAR1-3B (partially illustrated SEQ ID NO:14) and NMDAR1-3C (partially illustrated in SEQ ID NO:6) comprise the NMDAR1-1 nucleotide sequence and further include a 474 bp insert between nucleotides 3687 and 3688. These insertions introduce a new open reading frame and TGA stop codon, and as a result, the C-terminal amino acid sequence subsequent to amino acid residue 845 in the variant receptors is very different from the C-terminus of NMDAR1-1 (FIG. 3B SEQ ID NOS 7–10). The mature human NMDAR1-2 and NMDAR1-3A, 3B and 3C receptors consist of 883 and 920 amino acids, (partially illustrated in SEQ ID NOS 8,4,12, and 10, respectively). The amino acid sequences of NMDAR1-3A (partially illustrated in SEQ ID NO:9) and NMDAR1-3C (partially illustrated in SEQ ID NO:10), differ by a single amino acid residue due to a base pair change in the nucleotide sequence of the 3A variant. The codon at position 217 of the inserted region in the 3A variant is changed from AGG to ACG in the 3C variant. This codon change alters the amino acid encoded from arginine in NMDAR1-3A to threonine in NMDAR1-3C. The amino acid sequence of NMDAR1-3B (partially illustrated in SEQ ID NO:12) differs from the amino acid sequences of NMDAR1-1 and NMDAR1-3C (partially illustrated in SEQ ID NO:11) by a single amino acid at position 470 in which the lysine of NMDAR1-3B is glutamic acid in NMDAR1-1 and NMDAR1-3C. This results from a single base pair change in the codon at position 2560 of NMDAR1-1 and NMDAR1-3C (partially illustrated in SEQ ID NO:13) from GAG to AAG in the 3B (partially illustrated in SEQ NO:14) variant (FIG. 4)(SEQ ID NO. 11–14). The NMDAR1-4 receptor (partially illustrated in SEQ ID NO:20) is encoded by a nucleotide sequence (partially illustrated in SEQ ID NO:18) corresponding to that of NMDAR1-1 which further includes a 111 bp insert between nucleotides 3687 and 3688 (FIG. 5A SEQ ID NOS 17 and 18) which encodes a peptide insert between amino acids 845 and 846 of NMDAR1-1 (FIG. 5B, SEQ ID NOS 19 and 20). The mature NMDAR1-4 protein comprises 904 amino acids. The NMDAR1-5, NMDAR1-6, NMDAR1-7 and NMDAR1-8 variants (partially illustrated in SEQ ID NOS:21) correspond respectively to the NMDAR1-1, NMDAR1-2, NMDAR1-3 and NMDAR1 -4 receptors partially illustrated in SEQ ID NO: 20 additionally including a 63 bp insertion at their N-terminal end between nucleotides 1663 and 1664 (FIG. 6A, SEQ ID NOS:21 and 22). The amino acid sequence of this insertion is illustrated in FIG. 6B (SEQ ID NOS 23 and 24).

In human hippocampus cDNA libraries, the source from which DNA coding for the NMDAR1-1 receptor was isolated, the NMDAR1-1 receptor is encoded by the nucleotide sequence provided in FIG. 1 (SEQ ID NO:1); however, due to the degeneracy associated with nucleotide triplet codons, it will be appreciated that the NMDAR1 receptor may be encoded by polynucleotides incorporating codons synonymous with those illustrated in FIG. 1. For example, as would be known by one of skill in the art, arginine may be encoded by any one of six codons selected from CGA, CGC, CGG, CGU, AGA and AGG, threonine may be encoded by any one of four codons selected from ACA, ACC, ACG and ACU, while lysine is encoded by two codons, AAA and AAG.

Like other members of the human NMDAR1 receptor family, receptor subtype NMDAR1-1 is characterized by a pharmacological profile i.e. a ligand binding "signature", that points strongly to an NMDA-type EAA receptor as distinct from other excitatory amino acid receptor types, such as AMPA and kainate receptors. In addition, and despite the understanding that NMDA-type receptors require a multi- and perhaps heteromeric subunit structure to function in the pharmacological sense, it has been found that cells producing the unitary NMDAR1-1 receptor do, independently of association with other receptor subunits, provide a reliable indication of excitatory amino acid binding. Thus, in a key aspect of the present invention, the human NMDAR1-1 receptor and the variants thereof, are exploited for the purpose of screening candidate compounds for the ability to interact with the present receptors and/or the ability to compete with endogenous EAA receptor ligands and known synthetic analogues thereof.

For use in assessing interaction between the receptor and a test ligand, it is desirable to construct by application of genetic engineering techniques a cell that produces a human NMDAR1 receptor in functional form as a heterologous product. The construction of such cell lines is achieved by introducing into a selected host cell a recombinant DNA construct in which DNA coding for a secretable form of the human NMDAR1 receptor, i.e. a form bearing either its native signal peptide or a functional, heterologous equivalent thereof, is associated with expression controlling elements that are functional in the selected host to drive expression of the receptor-encoding DNA, and thus elaborate the desired NMDAR1 receptor protein. Such cells are herein characterized as having the receptor-encoding DNA incorporated "expressibly" therein. The receptor-encoding DNA is referred to as "heterologous" with respect to the particular cellular host if such DNA is not naturally found in the particular host.

It is most desirable to use a mammalian cell host to produce NMDAR1 receptors due to the mammalian origin of the present human NMDAR1 receptors; however, other suitably engineered eukaryotic and prokaryotic hosts may also be employed to produce NMDAR1 receptors. Accordingly, bacterial hosts such as *E. coli* and *B. subtilis,* fungal hosts such as Aspergillus and yeast and insect cell hosts such as *Spodoptera frugiperda,* are examples of non-mammalian hosts that may also be used to produce NMDAR1 receptors of the present invention.

The particular cell type selected to serve as host for production of the human NMDAR1 receptor can be any of several cell types currently available in the art, but should not of course be a cell type that in its natural state elaborates a surface receptor that can bind excitatory amino acids, and so confuse the assay results sought from the engineered cell line. Generally, such problems are avoided by selecting as host a non-neuronal cell type, and can further be avoided using non-human cell lines, as is conventional. It will be appreciated that neuronal- and human-type cells may nevertheless serve as expression hosts, provided that "background" binding to the test ligand is accounted for in the assay results.

According to one embodiment of the present invention, the cell line selected to serve as host for NMDAR1 receptor production is a mammalian cell. Several types of such cell lines are currently available for genetic engineering work, and these include the chinese hamster ovary (CHO) cells for example of K1 lineage (ATCC CCL 61) including the Pro5 variant (ATCC CRL 1281); fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651); murine L-cells, murine 3T3 cells (ATCC CRL 1658), murine C127 cells, human embryonic kidney cells of the 293 lineage (ATCC CRL 1573), human carcinoma cells including those of the HeLa lineage (ATCC CCL 2), and neuroblastoma cells of the lines IMR-32 (ATCC CCL 127), SK-N-MC (ATCC HTB 10) and SK-N-SH (ATCC HTB 11).

A variety of gene expression systems have been adapted for use with these hosts and are now commercially available. Any one of these systems can be exploited to drive expression of the NMDAR1 receptor-encoding DNA. These systems, available typically in the form of plasmidic vectors, incorporate expression cassettes, the functional components of which include DNA constituting host-recognizable expression controlling sequences which enable expression of the receptor-encoding DNA when linked 5' thereof. The systems further incorporate DNA sequences which terminate expression when linked 3' of the receptor-encoding region. Thus, for expression in a selected mammalian cell host, there is generated a recombinant DNA expression construct in which DNA encoding an NMDAR1 receptor is linked with expression controlling DNA sequences recognized by the host, including a region 5' of the receptor-encoding DNA to drive expression, and a 3' region to terminate expression. The plasmidic vector harbouring the expression construct typically incorporates such other functional components as an origin of replication, usually virally-derived, to permit replication of the plasmid in the expression host, including bacterial hosts such as *E. coli*. To provide a marker enabling selection of stably transformed recombinant cells, the vector will also incorporate a gene conferring some survival advantage on the transformants, such as a gene coding for neomycin resistance in which case the transformants are plated in medium supplemented with neomycin.

Included among the various recombinant DNA expression systems that can be used to achieve mammalian cell expression of the receptor-encoding DNA are those that exploit promoters of viruses that infect mammalian cells, such as the promoter from the cytomegalovirus (CMV), the Rous sarcoma virus (RSV), simian virus (SV40), murine mammary tumor virus (MMTV) and others. Also useful to drive expression are promoters such as the long terminal repeat (LTR) of retroviruses, insect cell promoters such as those regulated by temperature, and isolated from Drosophila, as well as mammalian gene promoters such as steroid-inducible promoters and those regulated by heavy metals i.e. the metalothionein gene promoter. In order to achieve expression in bacterial hosts, such as *E. coli,* expression systems that exploit the expression controlling regions of various *E. coli* and viral genes can be used to drive NMDAR1 receptor production including the lac gene, the trp gene, and regions of the lambda genome (PL and PR). Expression in yeast can be achieved using the expression-controlling regions of genes such as alcohol dehydrogenase and melibiase, and in Aspergillus, the expression-controlling regions of genes such as alcohol dehydrogenase and glucoamylase may be used. The expression controlling-regions of baculovirus may be used in the case of insect host cells.

For incorporation into the recombinant DNA expression vector, DNA coding for the desired NMDAR1 receptor, e.g. the NMDAR1-1 receptor, an MK-801-binding variant thereof, or a variant of the NMDAR1-1 receptor, can be obtained by applying selected techniques of gene isolation or gene synthesis. As described in more detail in the examples herein, the NMDAR1-1 receptor, and variants thereof, are encoded within the genome of human brain tissue, and can therefore be obtained by careful application of conventional gene isolation and cloning techniques. This typically will entail extraction of total messenger RNA from a fresh source of human brain tissue, such as cerebellum or fetal brain tissue and preferably hippocampus tissue, followed by conversion of message to cDNA and formation of a library in, for example, a bacterial plasmid, or more typically a bacteriophage. Bacteriophage harbouring fragments of the human DNA are typically grown by plating on a lawn of susceptible *E. coli* bacteria, such that individual phage plaques or colonies can be isolated. The DNA carried by the phage colony is then typically immobilized on a nitrocellulose or nylon-based hybridization membrane, and then hybridized, under carefully controlled conditions, to a radioactively (or otherwise) labelled nucleotide probe of appropriate sequence to identify the particular phage colony carrying receptor-encoding DNA or fragments thereof. Typically, the gene or a portion thereof so identified is subcloned into a plasmidic vector for nucleic acid sequence analysis.

Having herein provided the nucleotide sequence of various human NMDAR1 receptors, it will be appreciated that automated techniques of gene synthesis and/or amplification can be performed to generate DNA coding therefor. Because of the length of NMDAR1 receptor-encoding DNA, application of automated synthesis may require staged gene construction, in which regions of the gene up to about 300 nucleotides in length are synthesized individually and then ligated in correct succession for final assembly. Individually synthesized gene regions can be amplified prior to assembly using polymerase chain reaction (PCR) technology as generally described by Barnett et al. in Nucl. Acids Res. 18:3094, 1990.

The application of automated gene synthesis techniques provides an opportunity to generate sequence variants of naturally occurring members of the NMDAR1 gene family. It will be appreciated, for example and as mentioned above, that polynucleotides coding for the NMDAR1 receptors herein described can be generated by substituting synonymous codons for those represented in the naturally occurring polynucleotide sequences herein identified. In addition, polynucleotides coding for synthetic variants of the NMDAR1 receptors herein described can be generated which, for example, incorporate one or more single amino acid substitutions, deletions or additions. Since it will for the most part be desirable to retain the natural ligand binding profile of the receptor for screening purposes, it is desirable to limit amino acid substitutions to the so-called conservative replacements in which amino acids of like charge are substituted, and to limit substitutions to those regions which are less critical for receptor activity as may be elucidated upon receptor domain mapping.

With appropriate template DNA in hand, the technique of PCR amplification may also be used to directly generate all or part of the final gene. In this case, primers are synthesized which will prime the PCR amplification of the final product, either in one piece, or in several pieces that may be ligated together. This may be via step-wise ligation of blunt-ended, amplified DNA fragments, or preferentially via step-wise ligation of fragments containing naturally occurring restriction endonuclease sites. In this application, it is possible to use either cDNA or genomic DNA as the template for the PCR amplification. In the former case, the cDNA template can be obtained from commercially available or self-constructed cDNA libraries of various human brain tissues, including hippocampus and cerebellum.

Once obtained, the receptor-encoding DNA is incorporated for expression into any suitable expression vector using conventional procedures, and host cells are transfected therewith also using conventional procedures which include, for example, DNA-mediated transformation, electroporation, microinjection, or particle gun transformation. Expression vectors may be selected to provide transformed mammalian cell lines that express the receptor-encoding DNA either transiently or in a stable manner. For transient expression, host cells are typically transformed with an expression vector harbouring an origin of replication functional in a mammalian cell. For stable expression, such replication origins are unnecessary, but the vectors will typically harbour a gene coding for a product that confers on the transformants a survival advantage, to enable their selection. Genes coding for such selectable markers include, but are not limited to, the *E. coli* gpt gene which confers resistance to mycophenolic acid, the neo gene from transposon Tn5 which confers resistance to the antibiotic G418 and to neomycin, the dhfr sequence from murine cells or *E. coli* which changes the phenotype of DHFR− cells into DHFR+ cells, and the tk gene of herpes simplex virus, which makes TK− cells phenotypically TK+ cells. Both transient expression and stable expression can provide transformed cell lines, and membrane preparations derived therefrom, for use in ligand screening assays.

For use in screening assays, cells transiently expressing the receptor-encoding DNA can be stored frozen for later use, but because the rapid rate of plasmid replication will lead ultimately to cell death, usually in a few days, the transformed cells should be used as soon as possible. Such assays may be performed either with intact cells, or with membrane preparations derived from such cells. The membrane preparations typically provide a more convenient substrate for the ligand binding experiments, and are therefore preferred as binding substrates. To prepare membrane preparations for screening purposes, i.e. ligand binding experiments, frozen intact cells are homogenized while in cold water suspension and a membrane pellet is collected after centrifugation. The pellet is re-suspended and re-centrifuged to remove endogenous EAA ligands such as glutamate, that would otherwise compete for binding in the assays. The membranes may then be used as such, or after storage in lyophilized form, in the ligand binding assays. Alternatively, intact, fresh cells harvested about two days after transient transfection or after about the same period following fresh plating of stably transfected cells, can be used for ligand binding assays by the same methods as used for membrane preparations. When cells are used, the cells must be harvested by more gentle centrifugation so as not to damage them, and all washing must be done in a buffered medium, for example in phosphate-buffered saline, to avoid osmotic shock and rupture of the cells.

The binding of a candidate ligand to a selected human NMDAR1 receptor of the invention is evaluated typically using a predetermined amount of cell-derived membrane (measured for example by protein determination), generally from about 25 ug to 100 ug. Generally, competitive binding assays will be useful to evaluate the affinity of a test compound relative to glutamate, for the receptor. This competitive binding assay can be performed by incubating the membrane preparation with radiolabelled glutamate, for example [$^3$H]-glutamate, in the presence of unlabelled test compound added at varying concentrations. Following incubation, either displaced or bound radiolabelled glutamate can be recovered and measured to determine the relative binding affinities of the test compound and glutamate for the particular receptor used as substrate. In this way, the affinities of various compounds for the NMDA-type human EAA receptors can be measured.

The NMDAR1 receptors of the present invention are per se functional in an electrophysiological context, and are therefore useful, in the established manner, in screening test ligands for their ability to modulate ion channel activity. The present invention thus further provides, as a ligand screening technique, a method of detecting interaction between a test ligand and a human CNS receptor, which comprises the steps of incubating the test ligand with a human NMDAR1 receptor-producing cell or with a membrane preparation derived therefrom, and then measuring ligand-induced electrical current across said cell or membrane.

As an alternative to using cells that express receptor-encoding DNA, ligand characterization, either through binding or through ion channel formation, may also be performed using cells (for example Xenopus oocytes), that yield functional membrane-bound receptor following introduction of messenger RNA coding for the NMDAR1 receptor. In this case, NMDAR1 receptor DNA is typically subcloned into a plasmidic vector such that the introduced DNA may be easily transcribed into RNA via an adjacent RNA transcription promoter supplied by the plasmidic vector, for example the T3 or T7 bacteriophage promoters. RNA is then transcribed from the inserted gene in vitro, and isolated and purified therefrom for injection into Xenopus oocytes. Following the injection of nanoliter volumes of an RNA solution, the oocytes are left to incubate for up to several days, and are then tested for the ability to respond to a particular ligand molecule supplied in a bathing solution. Since functional EAA receptors act in part by operating a membrane channel through which ions may selectively pass, the functioning of the receptor in response to a particular ligand molecule in the bathing solution may typically be measured as an electrical current utilizing microelectrodes inserted into the cell or placed on either side of a cell-derived membrane preparation using the "patch-clamp" technique.

In addition to using the receptor-encoding DNA to construct cell lines useful for ligand screening, expression of the DNA can, according to another aspect of the invention, be performed to produce fragments of the receptor in soluble form, for structure investigation, to raise antibodies and for other experimental uses. It is expected that the portion of the NMDAR1 receptor responsible for binding a ligand molecule resides on the outside of the cell, i.e. is extracellular. It is therefore desirable in the first instance to facilitate the characterization of the receptor-ligand interaction by providing this extracellular ligand-binding domain in quantity and in isolated form, i.e. free from the remainder of the receptor. To accomplish this, the full-length NMDAR1 receptor-encoding DNA may be modified by site-directed mutagenesis, to introduce a translational stop codon into the extracellular N-terminal region, immediately 5' of the first transmembrane domain (TM1), i.e., before the amino acid residue 544 codon as shown in FIG. 1 (SEQ ID NOS: 1 and 2). Since there will no longer be produced any transmembrane domain(s) to "anchor" the receptor into the membrane, expression of the modified cDNA will result in the secretion, in soluble form, of only the extracellular N-terminal ligand-binding domain. Standard ligand-binding assays may then be performed to ascertain the degree of binding of a candidate compound to the extracellular domain so produced. It may of course be necessary, using site-directed mutagenesis, to produce different versions of the extracellular regions, in order to map the ligand binding domain with precision. It will also be appreciated that the length of the fragment may be varied, i.e. to lengths less than the entire 544 amino acid extracellular N-terminal domain.

Alternatively, it may be desirable to produce an extracellular domain of the receptor which is not derived from the N-terminus of the mature protein, but rather from the carboxy-terminus, for example domains immediately following the fourth transmembrane domain (TM4), e.g. residing between amino acid residues 816 and 867 inclusive in NMDAR1-1 as shown in FIG. 1(SEQ ID NOS 1 and 2), between amino acid residues 816 and 883 in NMDAR1-2 or between amino acid residues 816 and 920 in NMDAR1-3A, -3B and -3C. In this case, site-directed mutagenesis and/or PCR-based amplification techniques may readily be used to provide a defined fragment of the cDNA encoding the receptor domain of interest. Direct peptide synthesis may also be used to make the desired C-terminal fragment, or as noted above, desired N-terminal fragments. Such a DNA sequence may be used to direct the expression of the desired receptor fragment, either intracellularly, or in secreted fashion, provided that the DNA encoding the gene fragment is inserted adjacent to a translation start codon provided by the expression vector, and that the required translation reading frame is carefully conserved.

It will be appreciated that the production of such extracellular ligand binding domains may be accomplished in a variety of host cells. Mammalian cells such as CHO cells may be used for this purpose, the expression typically being driven by an expression promoter capable of high-level expression, for example, the CMV promoter. Alternately, non-mammalian cells, such as insect Sf9 (*Spodoptera frugiperda*) cells may be used, with the expression typically being driven by expression promoters of the baculovirus, for example the strong, late polyhedrin protein promoter. Filamentous fungal expression systems may also be used to secrete large quantities of such extracellular domains of the NMDAR1 receptor. *Aspergillus nidulans* for example, with the expression being driven by the alcA promoter, would constitute such an acceptable fungal expression system. In addition to such expression hosts, it will be further appreciated that any prokaryotic or other eukaryotic expression system capable of expressing heterologous genes or gene fragments, whether intracellularly or extracellularly would be similarly acceptable.

For use particularly in detecting the presence and/or location of a NMDAR1 receptor, for example in brain tissue, the present invention also provides, in another of its aspects, labelled antibody to a human NMDAR1 receptor. To raise such antibodies, there may be used as immunogen either the intact, soluble receptor or an immunogenic fragment thereof, produced in a microbial or mammalian cell host as described above or by standard peptide synthesis techniques. Regions of the NMDAR1-1 receptor particularly suitable for use as immunogenic fragments include those corresponding in sequence to an extracellular region of the receptor, or a portion of the extracellular region, such as peptides consisting of residues 1–543, including particularly residues 497–539, and peptides corresponding to the extracellular region between transmembrane domains TM-2 and TM-3, such as a peptide consisting of residues 603–612. Peptides consisting of the carboxy-terminal domain (residues 816–867), or fragments thereof may also be used for the raising of antibodies. Substantially the same regions of the variants of human NMDAR1-1, namely, the NMDAR1-2 to NMDAR1-8 receptors, may also be used for production of antibodies, taking into account the elongated carboxy terminal domains of a number of these variants.

The raising of antibodies to the desired NMDAR1 receptor or immunogenic fragment can be achieved, for polyclonal antibody production, using immunization protocols of conventional design, and any of a variety of mammalian hosts, such as sheep, goats and rabbits. Alternatively, for monoclonal antibody production, immunocytes such as splenocytes can be recovered from the immunized animal and fused, using hybridoma technology, to myeloma cells. The fusion cell products, i.e. hybridoma cells, are then screened by culturing in a selection medium, and cells producing the desired antibody are recovered for continuous growth, and antibody recovery. Recovered antibody can then be coupled covalently to a reporter molecule, i.e. a detectable label, such as a radiolabel, enzyme label, luminescent label or the like, using linker technology established for this purpose, to form a specific probe for NMDAR1 receptors.

In detectably labelled form, e.g. radiolabelled form, DNA or RNA coding for the human NMDAR1 receptor, and selected regions thereof, may also be used, in accordance with another aspect of the present invention, as hybridization probes for example to identify sequence-related genes resident in the human or other mammalian genomes (or cDNA libraries) or to locate the NMDAR1-encoding DNA in a specimen, such as brain tissue. This can be done using either the intact coding region, or a fragment thereof, having radiolabelled nucleotides, for example, $^{32}P$ nucleotides, incorporated therein. To identify the NMDAR1-encoding DNA in a specimen, it is desirable to use either the full length cDNA coding therefor, or a fragment which is unique thereto. With reference to FIG. 1 (SEQ ID NO:1 and the nucleotide numbering appearing thereon, such nucleotide fragments include those comprising at least about 17 nucleic acids, and otherwise corresponding in sequence to a region coding for the N-terminus or C-terminus of the receptor, or representing a 5'-untranslated or 3'-untranslated region thereof. One example of a suitable nucleotide fragment is the region spanning nucleotides 2605 to 3213 of NMDAR1-1, as described herein in the Examples. These sequences, and the intact gene itself, may also be used of course to clone NMDAR1-related human genes, particularly cDNA equivalents thereof, by standard hybridization techniques.

Embodiments of the present invention are described in detail in the following non-limiting Examples.

EXAMPLE 1

Isolation of DNA Coding for the Human NMDAR1-1 Receptor

A human NMDAR1 probe corresponding to a portion of nucleotide sequence of NMDAR1-1, namely the nucleotide region 2605–3213 as shown in FIG. 1, was generated by PCR-based amplification of recombinant bacteriophage lambda DNA isolated from an Eco RI-based bacteriophage λ library of human hippocampus cDNA (obtained from Stratagene Cloning Systems, La Jolla, Calif.). The following degenerate oligonucleotide primers (SEQ ID NOS 15 and 16) were used in the PCR amplification:

1) 5' GGGGTTTEGGATCCAA-A/G-GA-A/G-TGGAA-C/T-GGNATGATG 3'; and 2) 5' GGGGTTTAAGCTT-C/T-TC-G/A-TA-G/A-TT-G/A-TG-C/T-TT-C/T-TCCAT 3'

The primers were used at a final concentration of 5 pmol/ul each, in a 50 ul reaction volume (10 mM Tris-HCl, pH 9.0; 50 mM KCl; 1.5 mM $MgCl_2$) containing 100 ng of recombinant human hippocampus cDNA/bacteriophage λ DNA, 5 units of *Thermus aquaticus* DNA polymerase (Promega, Madison, Wis.) and 0.2 mM of each deoxyribonucleotide. Thirty-five cycles of amplification proceeded, with denaturation at 94° C. for 1 min., annealing at 51° C. for 1 min., and primer extension at 72° C. for 1 min., followed by a final cycle at 72° C. for 5 min. The 674 bp PCR product was purified from an agarose gel and subcloned into the plasmid vector pTZBlue-T (Novagen, Madison, Wis.) for DNA sequencing. The nucleotide sequence of this fragment was 88% identical to that of the rat NMDAR1 cDNA.

The 674 bp human NMDAR1 probe was radiolabelled with [α-$^{32}$P]dCTP using the Amersham Megaprime DNA labelling system (Arlington Heights, Ill.) to a specific activity of $1.0$–$2.4 \times 10^9$ cpm/ug. The labelled probe was used to screen approximately 400,000 plaques of an Eco RI-based human hippocampus cDNA/bacteriophage λ Zap II library. Thirty-five positive plaques were identified on replica filters under the following hybridization conditions: 6×SSC, 50% formamide, 0.5% SDS, 100 ug/ml denatured salmon sperm DNA at 42° C. with $1.85 \times 10^6$ cpm probe per ml hybridization fluid. The filters were washed with 2×SSC, 0.5% SDS at 25° C. for 5 min., followed by 15 min. washes at 37° C. and at 42° C. The filters were exposed to X-ray film (Kodak, Rochester, N.Y.) overnight. Twenty-eight plaques were purified and excised as phagemids according to the supplier's specifications, to generate an insert-carrying Bluescript-SK variant of the phagemid vector.

DNA sequence analysis of the largest clone (NMDAR1-1) revealed a putative ATG initiation codon together with about 1098 bases of 5' non-coding information and 2655 bases of amino acid coding information. This analysis also revealed a termination codon as well as about 906 bases of 3' non-translated information. The entire DNA sequence of the EcoRI-EcoRI NMDAR1-1 cDNA insert is provided in FIG. 1 (SEQ ID NOS 1 and 2).

A 7.6 kb phagemid designated pBS/humNMDAR1-1 carrying the receptor-encoding DNA as a 4.7 kbp EcoRI-EcoRI insert in a 2.9 kbp Bluescript-SK-phagemid background, was deposited, under the terms of the Budapest Treaty, with the American Type Culture Collection in Rockville, Md., USA on Nov. 12, 1992 and has been assigned accession number ATCC 75349.

EXAMPLE 2
Construction of Genetically Engineered Cells Producing the Human NMDAR1-1 Receptor For transient expression in mammalian cells, cDNA coding for the human NMDAR1-1 receptor was incorporated into the mammalian expression vector pcDNA1/Amp, which is available commercially from Invitrogen Corporation (San Diego, Calif.). This is a multifunctional 4.8 kbp plasmid vector designed for cDNA expression in eukaryotic systems, and cDNA analysis in prokaryotes. Incorporated on the vector are the CMV immediate early gene promoter and enhancer sequences, SV40 transcription termination and RNA processing signals, SV40 and polyoma virus origins of replication, M13 and ColE1 origins, Sp6 and T7 RNA promoters, and a gene conferring ampicillin resistance. A polylinker is located appropriately downstream of the CMV and T7 promoters.

The strategy depicted in FIG. 2 was employed to facilitate incorporation of the NMDAR1-1 receptor-encoding cDNA into the expression vector. The cDNA insert was released from pBS/humNMDAR1-1 as a 4.7 kbp Sal I/Spe I fragment, which was then incorporated at the Xho I/Xba I sites in the pcDNA1/Amp polylinker. DNA sequence analysis across the junctions was performed to confirm proper insert orientation. The resulting plasmid, designated pcDNA1/Amp/humNMDAR1-1, was then introduced for transient expression into a selected mammalian cell host, in this case the monkey-derived, fibroblast-like cells of the COS-1 lineage (available from the American Type Culture Collection, Rockville, Md. as ATCC CRL 1650).

For transient expression of the humNMDAR1-1-encoding DNA, COS-1 cells were transfected with approximately 8 ug DNA (as pcDNA1/Amp/humNMDAR1-1) per $10^6$ COS-1 cells, by DEAE-mediated DNA transfection and treated with chloroquine according to the procedures described by Sambrook et al., Molecular Cloning-A Laboratory Manual, Cold Spring Harbour Laboratory Press, 1989. Briefly, COS-1 cells were plated at a density of $5 \times 10^6$ cells/dish and then grown for 24 hours in 10% FBS-supplemented DMEM/F12 medium. Medium was then removed and cells were washed in PBS followed by medium (lacking FBS). Ten milliliters of a transfection solution containing DEAE dextran (0.4 mg/ml), 100 uM chloroquine, 10% NuSerum, DNA (0.4 mg/ml) in DMEM/F12 medium was then applied to the cells. After incubation for 3 hours at 37° C., cells were washed as previously described and then shocked for 1 minute with 10% DMSO in DMEM/F12 medium. Cells were allowed to grow for 2–3 days in 10% FBS-supplemented medium, and at the end of incubation, dishes were placed on ice, the cells were washed with ice cold PBS and then removed by scraping. Cells were then harvested by centrifugation at 1000 rpm for 10 minutes and the cellular pellet was frozen in liquid nitrogen for subsequent use in ligand binding assays.

In a like manner, stably transfected cell lines can also be prepared using two different cell types as host: CHO K1 and CHO Pro5. To construct these cell lines, cDNA coding for human NMDAR1 is incorporated into the mammalian expression vector pRC/CMV (Invitrogen) which enables stable expression. Insertion of the cDNA places it under the expression control of the CMV promoter and upstream of the polyadenylation site and terminator of the bovine growth hormone gene, and into a vector background comprising the neomycin resistance gene (driven by the SV40 early promoter) as selectable marker.

To introduce plasmids constructed as described above, the host CHO cells are first seeded at a density of $5 \times 10^5$ cells/dish in 10% FBS-supplemented αMEM medium. After growth for 24 hours, fresh medium is added to the plates and three hours later, the cells are transfected using the calcium phosphate-DNA co-precipitation procedure (Sambrook et al. supra). Briefly, 3 ug of DNA is mixed and incubated with buffered calcium solution for 10 minutes at room temperature. An equal volume of buffered phosphate solution is added and the suspension is incubated for 15 minutes at room temperature. Next, the incubated suspension is applied to the cells for 4 hours, removed and cells were shocked with medium containing 15% glycerol. Three minutes later, cells are washed with medium and incubated for 24 hours at normal growth conditions. Cells resistant to neomycin are selected in 10% FBS-supplemented α-MEM medium containing G418 (1 mg/ml). Individual colonies of G418-resistant cells are isolated about 2–3 weeks later, clonally selected and then propagated for assay purposes.

EXAMPLE 3
Ligand Binding Assays

Frozen transfected COS cells were resuspended in ice-cold distilled water, sonicated for 5 seconds, and centrifuged for 10 minutes at 50,000×g. The supernatant was discarded and the membrane pellet stored frozen at −70° C.

COS-1 cell membrane pellets were resuspended in ice cold 50 mM Tris-HCl, pH 7.55, and centrifuged again at 50,000×g for 10 minutes in order to remove endogenous glutamate that would otherwise compete for binding. The pellets were resuspended in ice cold 50 mM Tris-HCl, pH 7.55, and used for the binding experiments described below. Protein concentrations were determined using the Pierce reagent with BSA as an internal standard.

Binding assays were performed using a 25–100 μg protein equivalent of the COS-derived membrane preparation, and a selected radiolabelled ligand. In particular, for MK-801-binding assays, incubation mixtures consisted of 20 nM (+)-[3-$^3$H]MK-801 (30 Ci/mmole), 20 μM glycine, and 1 mM L-glutamate in the cold incubation buffer at a final volume of 250 μl. Non-specific binding was determined in the presence of 1 mM (+)MK-801. For glutamate binding assays, incubation mixtures consisted of 30 nM [3,4-$^3$H]-L-glutamate (47.3 Ci/mmole) in the cold incubation buffer at a final volume of 250 μl. Non-specific binding was determined in the presence of 1 mM L-glutamate and displacement was determined in the presence of 1 mM NMDA, 1 mM kainate, or 1 mM AMPA. The reaction mixtures were incubated on ice for 60 minutes in plastic mini-vials. Bound and free ligand were separated by centrifugation for 30 minutes at 50,000×g. The pellets were washed three times in 4 ml of the cold incubation buffer, and then 4 ml of Beckman Ready-Protein Plus scintillation cocktail was added for liquid scintillation counting.

Figure 7:
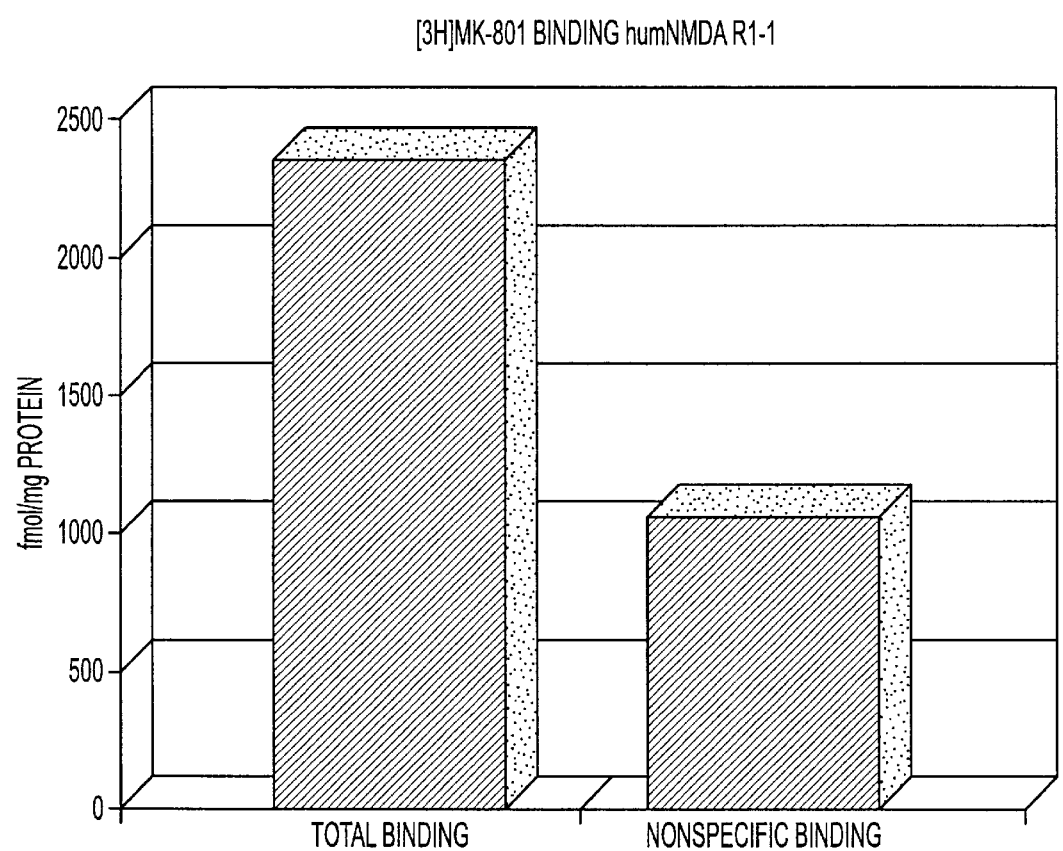
FIGS. 7 and 8 illustrate ligand-binding properties of the EAA receptor expressed from the coding region provided in FIG. 1.
Figure 8:
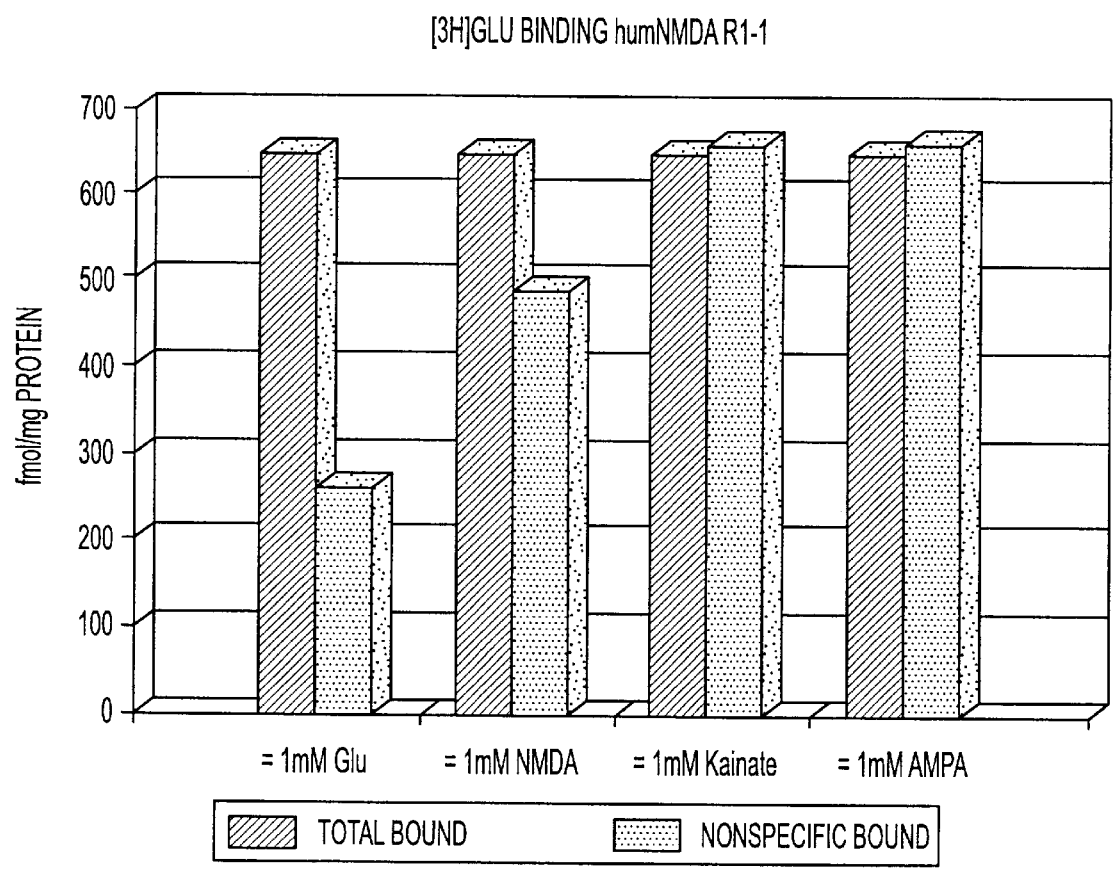

Assays performed in this manner, using membrane preparations derived from the human NMDAR1-1-producing COS-1 cells, revealed specific [$^3$H]MK-801 binding at 20 nM labelled ligand (FIG. 7), and specific [$^3$H]-L-glutamate binding at 30 nM labelled ligand (FIG. 8). The level of specific binding for MK-801 was determined to be 1286 fmol/mg protein, and the specific binding for glutamate was determined to be 387 fmol/mg protein. Mock transfected cells exhibited no specific binding of any of the ligands tested. Some displacement of [$^3$H]-glutamate binding could be observed in the presence of 1 mM NMDA. These results demonstrate clearly that the human NMDAR1-1 receptor is binding glutamate and MK-801 specifically. This property clearly assigns the human NMDAR1-1 receptor to be of the NMDA-type of EAA receptor. Furthermore, this binding profile indicates that the receptor is functioning in an authentic manner, and can therefore be used to reliably predict the ligand binding "signature" of its non-recombinant counterpart from the intact human brain. These features make the recombinant receptor especially useful for selecting and characterizing ligand compounds which bind to the receptor, and/or for selecting and characterizing compounds which may act by displacing other ligands from the receptor. The isolation of the NMDAR1-1 receptor gene in a pure form, capable of being expressed as a single, homogenous receptor species, therefore frees the ligand binding assay from the lack of precision introduced when complex, heterogeneous receptor preparations from human and non-human brains are used to attempt such characterizations.

EXAMPLE 4
Isolation and Cloning of NMDAR1-1 Variant Receptors

The procedures described in Examples 1 and 2 for isolating and cloning the NMDAR1-1 receptor apply equally to the naturally occuring variant receptors of NMDAR1-1, particularly in view of sequence similarities between the NMDAR1-1 receptor and the identified variants thereof.

Moreover, the ligand-binding assay set out in Example 3 can be used in the manner described to determine the ligand binding characteristics of receptor variants.

We claim:

1. An isolated polynucleotide comprising a nucleotide sequence that codes for a human NMDAR1, wherein said NMDAR1 has the sequence of amino acids 1–867 of SEQ ID NO:2 with none to as many as 6 amino acid substitutions.

2. A recombinant DNA construct having incorporated therein a polynucleotide as defined in claim 1.

3. A cell that has been engineered genetically to produce a human NMDAR1, said cell having incorporated expressibly therein a heterologous polynucleotide as defined in claim 1.

4. A cell as defined in claim 3, which is a mammalian cell.

5. A membrane preparation derived from a cell as defined in claim 3.

6. A method of assaying a test ligand for binding with a human CNS receptor, which comprises the steps of incubating the test ligand under appropriate conditions with a human NMDAR1-producing cell as defined in claim 3, or with a membrane preparation derived therefrom, and then determining the extent of binding between the human NMDAR1 and the test ligand.

7. A method of assaying a test ligand for electrophysiological effect upon interaction with a human CNS receptor, which comprises the steps of incubating the test ligand under appropriate conditions with a human NMDAR1-producing cell as defined in claim 3 or with membrane preparation derived therefrom, and then determining ligand-induced electrical current across said cell or membrane.

8. A process for obtaining a human EAA receptor in substantially homogeneous form, which comprises the steps of culturing cells having incorporated expressibly therein a polynucleotide as defined in claim 1, and then recovering the cultured cells.

9. A process according to claim 8, comprising the subsequent step of obtaining a membrane preparation from the cultured cells.

10. A human NMDAR1, in a form essentially free from other proteins of human origin, said NMDAR1 being encoded by a polynucleotide as defined in claim 1.

11. An isolated polynucleotide which codes for a receptor selected from the group consisting of:
   (a) NMDAR1-1 having the sequence of amino acids 1–867 of SEQ ID NO: 2;
   (b) NMDAR1-2 having the sequence of SEQ ID NO: 25;
   (c) NMDAR1-3A having the sequence of SEQ ID NO: 26;
   (d) NMDAR1-3C having the sequence of SEQ ID NO: 27;
   (e) NMDAR1-3B having the amino acid sequence of NMDAR1-3C except that residue 470 is a lysine residue;
   (f) NMDAR1-4 having the amino acid sequence of SEQ ID NO: 28;
   (g) NMDAR1-5 having the amino acid sequence of SEQ ID NO: 29;
   (h) NMDAR1-6 having the amino acid sequence of SEQ ID NO: 30;
   (i) NMDAR1-7 having the amino acid sequence of SEQ ID NO: 31;
   (j) NMDAR1-8 having the amino acid sequence of SEQ ID NO: 32.

12. An isolated polynucleotide encoding a human NMDAR1-1 having at least 99.6% amino acid identity with the 1-845 amino acid region of SEQ ID NO:2 of the NMDAR1-1.

* * * * *

SEQUENCE LISTING (1) GENERAL INFORMATION:

(iii) NUMBER OF SEQUENCES: 32

(2) INFORMATION FOR SEQ ID NO: 1:

(i) SEQUENCE CHARACTERISTICS:
      (A) LENGTH: 4659 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: misc_feature
      (B) LOCATION: 2781..2838
      (D) OTHER INFORMATION: /function= "transmembrane domain"

(ix) FEATURE:
      (A) NAME/KEY: misc_feature
      (B) LOCATION: 2895..2958
      (D) OTHER INFORMATION: /function= "transmembrane domain"

(ix) FEATURE:
      (A) NAME/KEY: misc_feature
      (B) LOCATION: 2988..3045
      (D) OTHER INFORMATION: /function= "transmembrane domain"

(ix) FEATURE:
      (A) NAME/KEY: misc_feature (B) LOCATION: 3534..3597
            (D) OTHER INFORMATION: /function= "transmembrane domain"

(ix) FEATURE:
            (A) NAME/KEY: CDS
            (B) LOCATION: 1099..3753

(ix) FEATURE:
            (A) NAME/KEY: mat_peptide
            (B) LOCATION: 1153..3753
            (D) OTHER INFORMATION: /product= "NMDAR1-1"

(ix) FEATURE:
            (A) NAME/KEY: sig_peptide
            (B) LOCATION: 1099..1152

(xi) SEQUENCE DESCRIPTION: SEQ ID NO: 1:

```
GAATTCCGGT AAGGCTCTGG AAAAGGGGGC GCTGGGAGCG CATTGCGAGG GGGCTGGAGA      60

GGGAGAGAGG AGCGGAAGCT GAGGGTGTGA AACGGCTGGC CCCGAACACA CCTCGCGGCG     120

CTCCAGTGAT TCCTGGTGTC CGACCTCAGC CCCAGTCAGT GCGGGTCCAG TTTCCAGGCT     180

CTCGCGGAAG GCCTGGCTGA GCACATGCGG CAGCCACGGT CGCCCTCCCT ATTCCTCTTA     240

GCCCGAGGAG GGGGGTCCCA AGTTACATGG CCACGCAGAT GGGGCCTCTC CCTCATTTCT     300

GAACCTTGTG GGGAGGGGAA CCTTGAAGGG AGCGCCCCCC AGAGCCATGG CTTAGGGCCT     360

CCCCCACCCC TCTGGAGCTC CAGTCTGCAA GAGTCAGGAG CCGAAATATC GCTGACTGTG     420

GGTGACGACT CTTGCGCGCA CACACACATA AAGCGGGCA CGACGCGTTC GGTCCTATTA     480

AAAGGCACGC AAGGGTGCGG CTGCACGCGG TGACACGGAC CCCTCTAACG TTTCCAAACT     540

GAGCTCCCTG CAGGTCCCCG ACAGCACAGG CCCCTGTCCC AGGACCCCTC CAGGCACGCG     600

CTCACACGCA CACGCGCGCT CCCCGGCTCA CGCGCGCTCC GACACACACG CTCACGCGAA     660

CGCAGGCGCA CGCTCTGGCG CGGGAGGCGC CCCTTCGCCT CCGTGTTGGG AAGCGGGGGC     720

GGCGGGAGGG GCAGGAGACG TTGGCCCCGC TCGCGTTTCT GCAGCTGCTG CAGTCGCCGC     780

AGCGTCCGGA CCGGAACCAG CGCCGTCCGC GGAGCCGCCG CCGCCGCCGC CGGGCCCTTT     840

CCAAGCCGGG CGCTCGGAGC TGTGCCCGGC CCCGCTTCAG CACCGCGGAC AGCTCCGGCC     900

GCGTGGGGCT GAGCCGAGCC CCCGCGCACG CTTCAGCCCC CTTCCCTCGG CCGACGTCCC     960

GGGACCGCCG CTCGGGGGA GACGTGGCGT CCGCAGCCCG CGGGGCCGGG CGAGCGCAGG    1020

ACGGCCCGGA AGCCCCGCGG GGGATGCGCC GAGGGCCCGC GTTCGCGCCG CGCAGAGCCA    1080
```

```
GGCCCGCGGC CGAGCCC ATG AGC ACC ATG CGC CTG CTG ACG CTC GCC CTG    1131
                    Met Ser Thr Met Arg Leu Leu Thr Leu Ala Leu
                    -18         -15                 -10

CTG TTC TCC TGC TCC GTC GCC CGT GCC GCG TGC GAC CCC AAG ATC GTC    1179
Leu Phe Ser Cys Ser Val Ala Arg Ala Ala Cys Asp Pro Lys Ile Val
        -5                   1                   5

AAC ATT GGC GCG GTG CTG AGC ACG CGG AAG CAC GAG CAG ATG TTC CGC    1227
Asn Ile Gly Ala Val Leu Ser Thr Arg Lys His Glu Gln Met Phe Arg
 10              15                  20                  25

GAG GCC GTG AAC CAG GCC AAC AAG CGG CAC GGC TCC TGG AAG ATT CAG    1275
Glu Ala Val Asn Gln Ala Asn Lys Arg His Gly Ser Trp Lys Ile Gln
                 30                  35                  40

CTC AAT GCC ACC TCC GTC ACG CAC AAG CCC AAC GCC ATC CAG ATG GCT    1323
Leu Asn Ala Thr Ser Val Thr His Lys Pro Asn Ala Ile Gln Met Ala
                 45                  50                  55

CTG TCG GTG TGC GAG GAC CTC ATC TCC AGC CAG GTC TAC GCC ATC CTA    1371
Leu Ser Val Cys Glu Asp Leu Ile Ser Ser Gln Val Tyr Ala Ile Leu
             60                  65                  70

GTT AGC CAT CCA CCT ACC CCC AAC GAC CAC TTC ACT CCC ACC CCT GTC    1419
```

-continued

```
Val Ser His Pro Pro Thr Pro Asn Asp His Phe Thr Pro Thr Pro Val
    75                  80                  85

TCC TAC ACA GCC GGC TTC TAC CGC ATA CCC GTG CTG GGG CTG ACC ACC    1467
Ser Tyr Thr Ala Gly Phe Tyr Arg Ile Pro Val Leu Gly Leu Thr Thr
 90                  95                 100                 105

CGC ATG TCC ATC TAC TCG GAC AAG AGC ATC CAC CTG AGC TTC CTG CGC    1515
Arg Met Ser Ile Tyr Ser Asp Lys Ser Ile His Leu Ser Phe Leu Arg
                110                 115                 120

ACC GTG CCG CCC TAC TCC CAC CAG TCC AGC GTG TGG TTT GAG ATG ATG    1563
Thr Val Pro Pro Tyr Ser His Gln Ser Ser Val Trp Phe Glu Met Met
            125                 130                 135

CGT GTC TAC AGC TGG AAC CAC ATC ATC CTG CTG GTC AGC GAC GAC CAC    1611
Arg Val Tyr Ser Trp Asn His Ile Ile Leu Leu Val Ser Asp Asp His
        140                 145                 150

GAG GGC CGG GCG GCT CAG AAA CGC CTG GAG ACG CTG CTG GAG GAG CGT    1659
Glu Gly Arg Ala Ala Gln Lys Arg Leu Glu Thr Leu Leu Glu Glu Arg
    155                 160                 165

GAG TCC AAG GCA GAG AAG GTG CTG CAG TTT GAC CCA GGG ACC AAG AAC    1707
Glu Ser Lys Ala Glu Lys Val Leu Gln Phe Asp Pro Gly Thr Lys Asn
170                 175                 180                 185

GTG ACG GCC CTG CTG ATG GAG GCG AAA GAG CTG GAG GCC CGG GTC ATC    1755
Val Thr Ala Leu Leu Met Glu Ala Lys Glu Leu Glu Ala Arg Val Ile
                190                 195                 200

ATC CTT TCT GCC AGC GAG GAC GAT GCT GCC ACT GTA TAC CGC GCA GCC    1803
Ile Leu Ser Ala Ser Glu Asp Asp Ala Ala Thr Val Tyr Arg Ala Ala
            205                 210                 215

GCG ATG CTG AAC ATG ACG GGC TCC GGG TAC GTG TGG CTG GTC GGC GAG    1851
Ala Met Leu Asn Met Thr Gly Ser Gly Tyr Val Trp Leu Val Gly Glu
        220                 225                 230

CGC GAG ATC TCG GGG AAC GCC CTG CGC TAC GCC CCA GAC GGC ATC CTC    1899
Arg Glu Ile Ser Gly Asn Ala Leu Arg Tyr Ala Pro Asp Gly Ile Leu
    235                 240                 245

GGG CTG CAG CTC ATC AAC GGC AAG AAC GAG TCG GCC CAC ATC AGC GAC    1947
Gly Leu Gln Leu Ile Asn Gly Lys Asn Glu Ser Ala His Ile Ser Asp
250                 255                 260                 265

GCC GTG GGC GTG GTG GCC CAG GCC GTG CAC GAG CTC CTC GAG AAG GAG    1995
Ala Val Gly Val Val Ala Gln Ala Val His Glu Leu Leu Glu Lys Glu
                270                 275                 280

AAC ATC ACC GAC CCG CCG CGG GGC TGC GTG GGC AAC ACC AAC ATC TGG    2043
Asn Ile Thr Asp Pro Pro Arg Gly Cys Val Gly Asn Thr Asn Ile Trp
            285                 290                 295

AAG ACC GGG CCG CTC TTC AAG AGA GTG CTG ATG TCT TCC AAG TAT GCG    2091
Lys Thr Gly Pro Leu Phe Lys Arg Val Leu Met Ser Ser Lys Tyr Ala
        300                 305                 310

GAT GGG GTG ACT GGT CGC GTG GAG TTC AAT GAG GAT GGG GAC CGG AAG    2139
Asp Gly Val Thr Gly Arg Val Glu Phe Asn Glu Asp Gly Asp Arg Lys
    315                 320                 325

TTC GCC AAC TAC AGC ATC ATG AAC CTG CAG AAC CGC AAG CTG GTG CAA    2187
Phe Ala Asn Tyr Ser Ile Met Asn Leu Gln Asn Arg Lys Leu Val Gln
330                 335                 340                 345

GTG GGC ATC TAC AAT GGC ACC CAC GTC ATC CCT AAT GAC AGG AAG ATC    2235
Val Gly Ile Tyr Asn Gly Thr His Val Ile Pro Asn Asp Arg Lys Ile
                350                 355                 360

ATC TGG CCA GGC GGA GAG ACA GAG AAG CCT CGA GGG TAC CAG ATG TCC    2283
Ile Trp Pro Gly Gly Glu Thr Glu Lys Pro Arg Gly Tyr Gln Met Ser
            365                 370                 375

ACC AGA CTG AAG ATT GTG ACG ATC CAC CAG GAG CCC TTC GTG TAC GTC    2331
Thr Arg Leu Lys Ile Val Thr Ile His Gln Glu Pro Phe Val Tyr Val
        380                 385                 390
```

```
                                        -continued

AAG CCC ACG CTG AGT GAT GGG ACA TGC AAG GAG GAG TTC ACA GTC AAC      2379
Lys Pro Thr Leu Ser Asp Gly Thr Cys Lys Glu Glu Phe Thr Val Asn
395                 400                 405

GGC GAC CCA GTC AAG AAG GTG ATC TGC ACC GGG CCC AAC GAC ACG TCG      2427
Gly Asp Pro Val Lys Lys Val Ile Cys Thr Gly Pro Asn Asp Thr Ser
410                 415                 420                 425

CCG GGC AGC CCC CGC CAC ACG GTG CCT CAG TGT TGC TAC GGC TTT TGC      2475
Pro Gly Ser Pro Arg His Thr Val Pro Gln Cys Cys Tyr Gly Phe Cys
                430                 435                 440

ATC GAC CTG CTC ATC AAG CTG GCA CGG ACC ATG AAC TTC ACC TAC GAG      2523
Ile Asp Leu Leu Ile Lys Leu Ala Arg Thr Met Asn Phe Thr Tyr Glu
                445                 450                 455

GTG CAC CTG GTG GCA GAT GGC AAG TTC GGC ACA CAG GAG CGG GTG AAC      2571
Val His Leu Val Ala Asp Gly Lys Phe Gly Thr Gln Glu Arg Val Asn
460                 465                 470

AAC AGC AAC AAG AAG GAG TGG AAT GGG ATG ATG GGC GAG CTG CTC AGC      2619
Asn Ser Asn Lys Lys Glu Trp Asn Gly Met Met Gly Glu Leu Leu Ser
475                 480                 485

GGG CAG GCA GAC ATG ATC GTG GCG CCG CTA ACC ATA AAC AAC GAG CGC      2667
Gly Gln Ala Asp Met Ile Val Ala Pro Leu Thr Ile Asn Asn Glu Arg
490                 495                 500                 505

GCG CAG TAC ATC GAG TTT TCC AAG CCC TTC AAG TAC CAG GGC CTG ACT      2715
Ala Gln Tyr Ile Glu Phe Ser Lys Pro Phe Lys Tyr Gln Gly Leu Thr
                510                 515                 520

ATT CTG GTC AAG AAG GAG ATT CCC CGG AGC ACG CTG GAC TCG TTC ATG      2763
Ile Leu Val Lys Lys Glu Ile Pro Arg Ser Thr Leu Asp Ser Phe Met
                525                 530                 535

CAG CCG TTC CAG AGC ACA CTG TGG CTG CTG GTG GGG CTG TCG GTG CAC      2811
Gln Pro Phe Gln Ser Thr Leu Trp Leu Leu Val Gly Leu Ser Val His
                540                 545                 550

GTG GTG GCC GTG ATG CTG TAC CTG CTG GAC CGC TTC AGC CCC TTC GGC      2859
Val Val Ala Val Met Leu Tyr Leu Leu Asp Arg Phe Ser Pro Phe Gly
555                 560                 565

CGG TTC AAG GTG AAC AGC GAG GAG GAG GAG GAG GAC GCA CTG ACC CTG      2907
Arg Phe Lys Val Asn Ser Glu Glu Glu Glu Glu Asp Ala Leu Thr Leu
570                 575                 580                 585

TCC TCG GCC ATG TGG TTC TCC TGG GGC GTC CTG CTC AAC TCC GGC ATC      2955
Ser Ser Ala Met Trp Phe Ser Trp Gly Val Leu Leu Asn Ser Gly Ile
                590                 595                 600

GGG GAA GGC GCC CCC AGA AGC TTC TCA GCG CGC ATC CTG GGC ATG GTG      3003
Gly Glu Gly Ala Pro Arg Ser Phe Ser Ala Arg Ile Leu Gly Met Val
                605                 610                 615

TGG GCC GGC TTT GCC ATG ATC ATC GTG GCC TCC TAC ACC GCC AAC CTG      3051
Trp Ala Gly Phe Ala Met Ile Ile Val Ala Ser Tyr Thr Ala Asn Leu
                620                 625                 630

GCG GCC TTC CTG GTG CTG GAC CGG CCG GAG GAG CGC ATC ACG GGC ATC      3099
Ala Ala Phe Leu Val Leu Asp Arg Pro Glu Glu Arg Ile Thr Gly Ile
635                 640                 645

AAC GAC CCT CGG CTG AGG AAC CCC TCG GAC AAG TTT ATC TAC GCC ACG      3147
Asn Asp Pro Arg Leu Arg Asn Pro Ser Asp Lys Phe Ile Tyr Ala Thr
650                 655                 660                 665

GTG AAG CAG AGC TCC GTG GAT ATC TAC TTC CGG CGC CAG GTG GAG CTG      3195
Val Lys Gln Ser Ser Val Asp Ile Tyr Phe Arg Arg Gln Val Glu Leu
                670                 675                 680

AGC ACC ATG TAC CGG CAT ATG GAG AAG CAC AAC TAC GAG AGT GCG GCG      3243
Ser Thr Met Tyr Arg His Met Glu Lys His Asn Tyr Glu Ser Ala Ala
                685                 690                 695

GAG GCC ATC CAG GCC GTG AGA GAC AAC AAG CTG CAT GCC TTC ATC TGG      3291
Glu Ala Ile Gln Ala Val Arg Asp Asn Lys Leu His Ala Phe Ile Trp
700                 705                 710
```

```
GAC TCG GCG GTG CTG GAG TTC GAG GCC TCG CAG AAG TGC GAC CTG GTG         3339
Asp Ser Ala Val Leu Glu Phe Glu Ala Ser Gln Lys Cys Asp Leu Val
        715                 720                 725

ACG ACT GGA GAG CTG TTT TTC CGC TCG GGC TTC GGC ATA GGC ATG CGC         3387
Thr Thr Gly Glu Leu Phe Phe Arg Ser Gly Phe Gly Ile Gly Met Arg
730                 735                 740                 745

AAA GAC AGC CCC TGG AAG CAG AAC GTC TCC CTG TCC ATC CTC AAG TCC         3435
Lys Asp Ser Pro Trp Lys Gln Asn Val Ser Leu Ser Ile Leu Lys Ser
                750                 755                 760

CAC GAG AAT GGC TTC ATG GAA GAC CTG GAC AAG ACG TGG GTT CGG TAT         3483
His Glu Asn Gly Phe Met Glu Asp Leu Asp Lys Thr Trp Val Arg Tyr
            765                 770                 775

CAG GAA TGT GAC TCG CGC AGC AAC GCC CCT GCG ACC CTT ACT TTT GAG         3531
Gln Glu Cys Asp Ser Arg Ser Asn Ala Pro Ala Thr Leu Thr Phe Glu
        780                 785                 790

AAC ATG GCC GGG GTC TTC ATG CTG GTA GCT GGG GGC ATC GTG GCC GGG         3579
Asn Met Ala Gly Val Phe Met Leu Val Ala Gly Gly Ile Val Ala Gly
    795                 800                 805

ATC TTC CTG ATT TTC ATC GAG ATT GCC TAC AAG CGG CAC AAG GAT GCT         3627
Ile Phe Leu Ile Phe Ile Glu Ile Ala Tyr Lys Arg His Lys Asp Ala
810                 815                 820                 825

CGC CGG AAG CAG ATG CAG CTG GCC TTT GCC GCC GTT AAC GTG TGG CGG         3675
Arg Arg Lys Gln Met Gln Leu Ala Phe Ala Ala Val Asn Val Trp Arg
                830                 835                 840

AAG AAC CTG CAG CAG TAC CAT CCC ACT GAT ATC ACG GGC CCG CTC AAC         3723
Lys Asn Leu Gln Gln Tyr His Pro Thr Asp Ile Thr Gly Pro Leu Asn
            845                 850                 855

CTC TCA GAT CCC TCG GTC AGC ACC GTG GTG TGAGGCCCCC GGAGGCGCCC           3773
Leu Ser Asp Pro Ser Val Ser Thr Val Val
        860                 865

ACCTGCCCAG TTAGCCCGGC CAAGGACACT GATGGGTCCT GCTGCTCGGG AAGGCCTGAG       3833
GGAAGCCCAC CCGCCCAGA GACTGCCCAC CCTGGGCCTC CCGTCCGTCC GCCCGCCCAC        3893
CCCGCTGCCT GGCGGGCAGC CCCTGCTGGA CCAAGGTGCG GACCGGAGCG GCTGAGGACG       3953
GGGCAGAGCT GAGTCGGCTG GCAGGGCGC  AGGGCGCTCC GGCAGAGGCA GGGCCCTGGG       4013
GTCTCTGAGC AGTGGGGAGC GGGGGCTAAC TGGCCCCAGG CGAAGGGGCT TGGAGCAGAG       4073
ACGGCAGCCC CATCCTTCCC GCAGCACCAG CCTGAGCCAC AGTGGGGCCC ATGGCCCCAG       4133
CTGGCTGGGT CGCCCCTCCT CGGGCGCCTG CGCTCCTCTG CAGCCTGAGC TCCACCCTCC       4193
CCTCTTCTTG CGGCACCGCC CACCCACACC CCGTCTGCCC CTTGACCCCA CACGCCGGGG       4253
CTGGCCCTGC CCTCCCCCAC GGCCGTCCCT GACTTCCCAG CTGGCAGCGC CTCCCGCCGC       4313
CTCGGGCCGC CTCCTCCAGA CTCGAGAGGG CTGAGCCCCT CCTCTCCTCG TCCGGCCTGC       4373
AGCCCAGAAC GGGCCTCCCC GGGGGTCCCC GGACGCTGGC TCGGGACTGT CTTCAACCCT       4433
GCCCTGCACC TTGGGCACGG GAGAGCGCCA CCCGCCCGCC CCCGCCCTCG CTCCGGGTCT       4493
GTGACCGGCC CGCCACCTTG TACAGAACCA GCACTCCCAG GGCCCGAGCG CGTGCCTTCC       4553
CCGTGCGGCC CGTGCGCAGC CGCGCTCTGC CCCTCCGTCC CCAGGGTGCA GGCGCGCACC       4613
GCCCAACCCC CACCTCCCGG TGTATGCAGT GGTGATGCCG GAATTC                     4659
```

(2) INFORMATION FOR SEQ ID NO: 2:

(i) SEQUENCE CHARACTERISTICS:
        (A) LENGTH: 885 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ser Thr Met Arg Leu Leu Thr Leu Ala Leu Leu Phe Ser Cys Ser
-18          -15                 -10                  -5

Val Ala Arg Ala Ala Cys Asp Pro Lys Ile Val Asn Ile Gly Ala Val
         1           5                  10

Leu Ser Thr Arg Lys His Glu Gln Met Phe Arg Glu Ala Val Asn Gln
 15              20              25                      30

Ala Asn Lys Arg His Gly Ser Trp Lys Ile Gln Leu Asn Ala Thr Ser
             35              40                      45

Val Thr His Lys Pro Asn Ala Ile Gln Met Ala Leu Ser Val Cys Glu
             50              55                      60

Asp Leu Ile Ser Ser Gln Val Tyr Ala Ile Leu Val Ser His Pro Pro
         65              70              75

Thr Pro Asn Asp His Phe Thr Pro Thr Pro Val Ser Tyr Thr Ala Gly
         80              85              90

Phe Tyr Arg Ile Pro Val Leu Gly Leu Thr Thr Arg Met Ser Ile Tyr
 95             100             105                     110

Ser Asp Lys Ser Ile His Leu Ser Phe Leu Arg Thr Val Pro Pro Tyr
             115             120                     125

Ser His Gln Ser Ser Val Trp Phe Glu Met Met Arg Val Tyr Ser Trp
             130             135                     140

Asn His Ile Ile Leu Leu Val Ser Asp Asp His Glu Gly Arg Ala Ala
             145             150             155

Gln Lys Arg Leu Glu Thr Leu Leu Glu Glu Arg Glu Ser Lys Ala Glu
 160             165             170

Lys Val Leu Gln Phe Asp Pro Gly Thr Lys Asn Val Thr Ala Leu Leu
 175             180             185                     190

Met Glu Ala Lys Glu Leu Glu Ala Arg Val Ile Ile Leu Ser Ala Ser
                 195             200             205

Glu Asp Asp Ala Ala Thr Val Tyr Arg Ala Ala Met Leu Asn Met
             210             215             220

Thr Gly Ser Gly Tyr Val Trp Leu Val Gly Glu Arg Glu Ile Ser Gly
             225             230             235

Asn Ala Leu Arg Tyr Ala Pro Asp Gly Ile Leu Gly Leu Gln Leu Ile
 240             245             250

Asn Gly Lys Asn Glu Ser Ala His Ile Ser Asp Ala Val Gly Val Val
 255             260             265             270

Ala Gln Ala Val His Glu Leu Leu Glu Lys Glu Asn Ile Thr Asp Pro
             275             280             285

Pro Arg Gly Cys Val Gly Asn Thr Asn Ile Trp Lys Thr Gly Pro Leu
             290             295             300

Phe Lys Arg Val Leu Met Ser Ser Lys Tyr Ala Asp Gly Val Thr Gly
             305             310             315

Arg Val Glu Phe Asn Glu Asp Gly Asp Arg Lys Phe Ala Asn Tyr Ser
             320             325             330

Ile Met Asn Leu Gln Asn Arg Lys Leu Val Gln Val Gly Ile Tyr Asn
 335             340             345             350

Gly Thr His Val Ile Pro Asn Asp Arg Lys Ile Ile Trp Pro Gly Gly
             355             360             365

Glu Thr Glu Lys Pro Arg Gly Tyr Gln Met Ser Thr Arg Leu Lys Ile
             370             375             380
```

-continued

```
Val Thr Ile His Gln Glu Pro Phe Val Tyr Val Lys Pro Thr Leu Ser
        385                 390                 395

Asp Gly Thr Cys Lys Glu Glu Phe Thr Val Asn Gly Asp Pro Val Lys
400                 405                 410

Lys Val Ile Cys Thr Gly Pro Asn Asp Thr Ser Pro Gly Ser Pro Arg
415                 420                 425                 430

His Thr Val Pro Gln Cys Cys Tyr Gly Phe Cys Ile Asp Leu Leu Ile
                435                 440                 445

Lys Leu Ala Arg Thr Met Asn Phe Thr Tyr Glu Val His Leu Val Ala
                450                 455                 460

Asp Gly Lys Phe Gly Thr Gln Glu Arg Val Asn Asn Ser Asn Lys Lys
                465                 470                 475

Glu Trp Asn Gly Met Met Gly Glu Leu Leu Ser Gly Gln Ala Asp Met
        480                 485                 490

Ile Val Ala Pro Leu Thr Ile Asn Asn Glu Arg Ala Gln Tyr Ile Glu
495                 500                 505                 510

Phe Ser Lys Pro Phe Lys Tyr Gln Gly Leu Thr Ile Leu Val Lys Lys
                515                 520                 525

Glu Ile Pro Arg Ser Thr Leu Asp Ser Phe Met Gln Pro Phe Gln Ser
                530                 535                 540

Thr Leu Trp Leu Leu Val Gly Leu Ser Val His Val Val Ala Val Met
        545                 550                 555

Leu Tyr Leu Leu Asp Arg Phe Ser Pro Phe Gly Arg Phe Lys Val Asn
        560                 565                 570

Ser Glu Glu Glu Glu Asp Ala Leu Thr Leu Ser Ser Ala Met Trp
575                 580                 585                 590

Phe Ser Trp Gly Val Leu Leu Asn Ser Gly Ile Gly Glu Gly Ala Pro
                595                 600                 605

Arg Ser Phe Ser Ala Arg Ile Leu Gly Met Val Trp Ala Gly Phe Ala
                610                 615                 620

Met Ile Ile Val Ala Ser Tyr Thr Ala Asn Leu Ala Ala Phe Leu Val
        625                 630                 635

Leu Asp Arg Pro Glu Glu Arg Ile Thr Gly Ile Asn Asp Pro Arg Leu
640                 645                 650

Arg Asn Pro Ser Asp Lys Phe Ile Tyr Ala Thr Val Lys Gln Ser Ser
655                 660                 665                 670

Val Asp Ile Tyr Phe Arg Arg Gln Val Glu Leu Ser Thr Met Tyr Arg
                675                 680                 685

His Met Glu Lys His Asn Tyr Glu Ser Ala Ala Glu Ala Ile Gln Ala
                690                 695                 700

Val Arg Asp Asn Lys Leu His Ala Phe Ile Trp Asp Ser Ala Val Leu
        705                 710                 715

Glu Phe Glu Ala Ser Gln Lys Cys Asp Leu Val Thr Thr Gly Glu Leu
        720                 725                 730

Phe Phe Arg Ser Gly Phe Gly Ile Gly Met Arg Lys Asp Ser Pro Trp
735                 740                 745                 750

Lys Gln Asn Val Ser Leu Ser Ile Leu Lys Ser His Glu Asn Gly Phe
                755                 760                 765

Met Glu Asp Leu Asp Lys Thr Trp Val Arg Tyr Gln Glu Cys Asp Ser
                770                 775                 780

Arg Ser Asn Ala Pro Ala Thr Leu Thr Phe Glu Asn Met Ala Gly Val
        785                 790                 795

Phe Met Leu Val Ala Gly Gly Ile Val Ala Gly Ile Phe Leu Ile Phe
```

```
                800              805              810
Ile Glu Ile Ala Tyr Lys Arg His Lys Asp Ala Arg Arg Lys Gln Met
815              820              825              830

Gln Leu Ala Phe Ala Ala Val Asn Val Trp Arg Lys Asn Leu Gln Gln
            835              840              845

Tyr His Pro Thr Asp Ile Thr Gly Pro Leu Asn Leu Ser Asp Pro Ser
            850              855              860

Val Ser Thr Val Val
        865

(2) INFORMATION FOR SEQ ID NO: 3:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 3:

GAAGAACCTG CAGCAGTACC ATCCCACT                                        28

(2) INFORMATION FOR SEQ ID NO: 4:

(i) SEQUENCE CHARACTERISTICS:
        (A) LENGTH: 391 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 4:

GAAGAACCTG CAGAGCACCG GGGGTGGACG CGGCGCTTTG CAAAACCAAA AAGACACAGT      60

GCTGCCGCGA CGCGCTATTG AGAGGGAGGA GGGCCAGCTG CAGCTGTGTT CCCGTCATAG     120

GGAGAGCTGA GACTCCCCGC CGCCCTCCT CTGCCCCCTC CCCCGCAGAC AGACAGACAG      180

ACGGATGGGA CAGCGGCCCG GCCCACGCAG AGCCCCGGAG CACCACGGGG TCGGGGAGG      240

AGCACCCCCA GCCTCCCCCA GGCTGCGCCT GCCCGCCCGC CGGTTGGCCG GCTGGCCGGT    300

CCACCCCGTC CCGGCCCCGC GCGTGCCCCC AGCGTGGGGC TAACGGGCGC CTTGTCTGTG    360

TATTTCTATT TTGCAGCAGT ACCATCCCAC T                                   391

(2) INFORMATION FOR SEQ ID NO: 5:

(i) SEQUENCE CHARACTERISTICS:
        (A) LENGTH: 502 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 5:

GAAGAACCTG CAGGATAGAA AGAGTGGTAG AGCAGAGCCT GACCCTAAAA AGAAAGCCAC      60

ATTTAGGGCT ATCACCTCCA CCCTGGCTTC CAGCTTCAAG AGGCGTAGGT CCTCCAAAGA    120

CACGAGCACC GGGGGTGGAC GCGGCGCTTT GCAAAACCAA AAAGACACAG TGCTGCCGCG    180

ACGCGCTATT GAGAGGGAGG AGGGCCAGCT GCAGCTGTGT TCCCGTCATA GGGAGAGCTG    240

AGACTCCCCG CCCGCCCTCC TCTGCCCCCT CCCCCGCAGA CAGACAGACA GACGGATGGG    300
```

| | | |
|---|---|---|
| ACAGCGGCCC GGCCCACGCA GAGCCCCGGA GCACCACGGG GTCGGGGAG GAGCACCCCC | 360 |
| AGCCTCCCCC AGGCTGCGCC TGCCCGCCCG CCGGTTGGCC GGCTGGCCGG TCCACCCCGT | 420 |
| CCCGGCCCCG CGCGTGCCCC CAGCGTGGGG CTAACGGGCG CCTTGTCTGT GTATTTCTAT | 480 |
| TTTGCAGCAG TACCATCCCA CT | 502 |

(2) INFORMATION FOR SEQ ID NO: 6:

(i) SEQUENCE CHARACTERISTICS:
        (A) LENGTH: 502 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 6:

| | | |
|---|---|---|
| GAAGAACCTG CAGGATAGAA AGAGTGGTAG AGCAGAGCCT GACCCTAAAA AGAAAGCCAC | 60 |
| ATTTAGGGCT ATCACCTCCA CCCTGGCTTC CAGCTTCAAG AGGCGTAGGT CCTCCAAAGA | 120 |
| CACGAGCACC GGGGGTGGAC GCGGCGCTTT GCAAAACCAA AAAGACACAG TGCTGCCGCG | 180 |
| ACGCGCTATT GAGAGGGAGG AGGGCCAGCT GCAGCTGTGT TCCCGTCATA CGGAGAGCTG | 240 |
| AGACTCCCCG CCCGCCCTCC TCTGCCCCCT CCCCCGCAGA CAGACAGACA GACGGATGGG | 300 |
| ACAGCGGCCC GGCCCACGCA GAGCCCCGGA GCACCACGGG GTCGGGGAG GAGCACCCCC | 360 |
| AGCCTCCCCC AGGCTGCGCC TGCCCGCCCG CCGGTTGGCC GGCTGGCCGG TCCACCCCGT | 420 |
| CCCGGCCCCG CGCGTGCCCC CAGCGTGGGG CTAACGGGCG CCTTGTCTGT GTATTTCTAT | 480 |
| TTTGCAGCAG TACCATCCCA CT | 502 |

(2) INFORMATION FOR SEQ ID NO: 7:

(i) SEQUENCE CHARACTERISTICS:
        (A) LENGTH: 65 amino acids
        (B) TYPE: amino acid
        (D) TOPOLOGY: linear (ii) MOLECULE TYPE: peptide (xi) SEQUENCE DESCRIPTION: SEQ ID NO: 7:

Ala Gly Gly Ile Val Ala Gly Ile Phe Leu Ile Phe Ile Glu Ile Ala
1               5                  10                  15

Tyr Lys Arg His Lys Asp Ala Arg Arg Lys Gln Met Gln Leu Ala Phe
            20                  25                  30

Ala Ala Val Asn Val Trp Arg Lys Asn Leu Gln Gln Tyr His Pro Thr
        35                  40                  45

Asp Ile Thr Gly Pro Leu Asn Leu Ser Asp Pro Ser Val Ser Thr Val
    50                  55                  60

Val
65

(2) INFORMATION FOR SEQ ID NO: 8:

(i) SEQUENCE CHARACTERISTICS:
        (A) LENGTH: 81 amino acids
        (B) TYPE: amino acid
        (D) TOPOLOGY: linear (ii) MOLECULE TYPE: peptide (xi) SEQUENCE DESCRIPTION: SEQ ID NO: 8:

Ala Gly Gly Ile Val Ala Gly Ile Phe Leu Ile Phe Ile Glu Ile Ala

```
1               5                    10                   15
Tyr Lys Arg His Lys Asp Ala Arg Arg Lys Gln Met Gln Leu Ala Phe
            20                  25                  30

Ala Ala Val Asn Val Trp Arg Lys Asn Leu Gln Ser Thr Gly Gly Gly
            35                  40                  45

Arg Gly Ala Leu Gln Asn Gln Lys Asp Thr Val Leu Pro Arg Arg Ala
            50                  55                  60

Ile Glu Arg Glu Glu Gly Gln Leu Gln Leu Cys Ser Arg His Arg Glu
65                  70                  75                  80

Ser
```

(2) INFORMATION FOR SEQ ID NO: 9:

(i) SEQUENCE CHARACTERISTICS:
        (A) LENGTH: 118 amino acids
        (B) TYPE: amino acid
        (D) TOPOLOGY: linear (ii) MOLECULE TYPE: peptide (xi) SEQUENCE DESCRIPTION: SEQ ID NO: 9:

```
Ala Gly Gly Ile Val Ala Gly Ile Phe Leu Ile Phe Ile Glu Ile Ala
1               5                   10                  15

Tyr Lys Arg His Lys Asp Ala Arg Arg Lys Gln Met Gln Leu Ala Phe
            20                  25                  30

Ala Ala Val Asn Val Trp Arg Lys Asn Leu Gln Asp Arg Lys Ser Gly
            35                  40                  45

Arg Ala Glu Pro Asp Pro Lys Lys Lys Ala Thr Phe Arg Ala Ile Thr
            50                  55                  60

Ser Thr Leu Ala Ser Ser Phe Lys Arg Arg Ser Ser Lys Asp Thr
65                  70                  75                  80

Ser Thr Gly Gly Gly Arg Gly Ala Leu Gln Asn Gln Lys Asp Thr Val
            85                  90                  95

Leu Pro Arg Arg Ala Ile Glu Arg Glu Glu Gly Gln Leu Gln Leu Cys
            100                 105                 110

Ser Arg His Arg Glu Ser
            115
```

(2) INFORMATION FOR SEQ ID NO: 10:

(i) SEQUENCE CHARACTERISTICS:
        (A) LENGTH: 118 amino acids
        (B) TYPE: amino acid
        (D) TOPOLOGY: linear (ii) MOLECULE TYPE: peptide (xi) SEQUENCE DESCRIPTION: SEQ ID NO: 10:

```
Ala Gly Gly Ile Val Ala Gly Ile Phe Leu Ile Phe Ile Glu Ile Ala
1               5                   10                  15

Tyr Lys Arg His Lys Asp Ala Arg Arg Lys Gln Met Gln Leu Ala Phe
            20                  25                  30

Ala Ala Val Asn Val Trp Arg Lys Asn Leu Gln Asp Arg Lys Ser Gly
            35                  40                  45

Arg Ala Glu Pro Asp Pro Lys Lys Lys Ala Thr Phe Arg Ala Ile Thr
            50                  55                  60

Ser Thr Leu Ala Ser Ser Phe Lys Arg Arg Ser Ser Lys Asp Thr
65                  70                  75                  80
```

Ser Thr Gly Gly Gly Arg Gly Ala Leu Gln Asn Gln Lys Asp Thr Val
            85                  90                  95

Leu Pro Arg Arg Ala Ile Glu Arg Glu Glu Gly Gln Leu Gln Leu Cys
            100                 105                 110

Ser Arg His Thr Glu Ser
        115

(2) INFORMATION FOR SEQ ID NO: 11:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO: 11:

Ala Asp Gly Lys Phe Gly Thr Gln Glu Arg Val Asn Asn Ser Asn Lys
1               5                   10                  15

Lys Glu Trp (2) INFORMATION FOR SEQ ID NO: 12:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO: 12:

Ala Asp Gly Lys Phe Gly Thr Gln Lys Arg Val Asn Asn Ser Asn Lys
1               5                   10                  15

Lys Glu Trp (2) INFORMATION FOR SEQ ID NO: 13:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 13:

TGGCAGATGG CAAGTTCGGC ACACAGGAGC GGGTGAACAA CAGCAACAAG AAGGAGTGGA      60

(2) INFORMATION FOR SEQ ID NO: 14:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 14:

TGGCAGATGG CAAGTTCGGC ACACAGAAGC GGGTGAACAA CAGCAACAAG AAGGAGTGGA      60

(2) INFORMATION FOR SEQ ID NO: 15:

(i) SEQUENCE CHARACTERISTICS:
        (A) LENGTH: 34 base pairs
        (B) TYPE: nucleic acid (C) STRANDEDNESS: double
        (D) TOPOLOGY: linear (ii) MOLECULE TYPE: cDNA (xi) SEQUENCE DESCRIPTION: SEQ ID NO: 15:

GGGGTTTGGA TCCAARGART GGAAYGGNAT GATG                             34

(2) INFORMATION FOR SEQ ID NO: 16:

(i) SEQUENCE CHARACTERISTICS:
        (A) LENGTH: 34 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 16:

GGGGTTTAAG CTTYTCRTAR TTRTGYTTYT CCAT                             34

(2) INFORMATION FOR SEQ ID NO: 17:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (xi) SEQUENCE DESCRIPTION: SEQ ID NO: 17:

GAAGAACCTG CAGCAGTACC ATCCCACT                                    28

(2) INFORMATION FOR SEQ ID NO: 18:

(i) SEQUENCE CHARACTERISTICS:
        (A) LENGTH: 139 base pairs
        (B) TYPE: nucleic acid
        (C) STRANDEDNESS: double
        (D) TOPOLOGY: linear (xi) SEQUENCE DESCRIPTION: SEQ ID NO: 18:

GAAGAACCTG CAGGATAGAA AGAGTGGTAG AGCAGAGCCT GACCCTAAAA AGAAAGCCAC   60

ATTTAGGGCT ATCACCTCCA CCCTGGCTTC CAGCTTCAAG AGGCGTAGGT CCTCCAAAGA  120

CACGCAGTAC CATCCCACT                                              139

(2) INFORMATION FOR SEQ ID NO: 19:

(i) SEQUENCE CHARACTERISTICS:
        (A) LENGTH: 65 amino acids
        (B) TYPE: amino acid
        (D) TOPOLOGY: linear (ii) MOLECULE TYPE: peptide (xi) SEQUENCE DESCRIPTION: SEQ ID NO: 19:

Ala Gly Gly Ile Val Ala Gly Ile Phe Leu Ile Phe Ile Glu Ile Ala
1               5                   10                  15

Tyr Lys Arg His Lys Asp Ala Arg Arg Lys Gln Met Gln Leu Ala Phe
                20                  25                  30

Ala Ala Val Asn Val Trp Arg Lys Asn Leu Gln Gln Tyr His Pro Thr
            35                  40                  45

Asp Ile Thr Gly Pro Leu Asn Leu Ser Asp Pro Ser Val Ser Thr Val
        50                  55                  60

Val (2) INFORMATION FOR SEQ ID NO: 20:

(i) SEQUENCE CHARACTERISTICS:
        (A) LENGTH: 102 amino acids
        (B) TYPE: amino acid
        (D) TOPOLOGY: linear (ii) MOLECULE TYPE: peptide (xi) SEQUENCE DESCRIPTION: SEQ ID NO: 20:

Ala Gly Gly Ile Val Ala Gly Ile Phe Leu Ile Phe Ile Glu Ile Ala
1               5                   10                  15

Tyr Lys Arg His Lys Asp Ala Arg Arg Lys Gln Met Gln Leu Ala Phe
            20                  25                  30

Ala Ala Val Asn Val Trp Arg Lys Asn Leu Gln Asp Arg Lys Ser Gly
            35                  40                  45

Arg Ala Glu Pro Asp Pro Lys Lys Lys Ala Thr Phe Arg Ala Ile Thr
        50                  55                  60

Ser Thr Leu Ala Ser Ser Phe Lys Arg Arg Ser Ser Lys Asp Thr
65                  70                  75                  80

Gln Tyr His Pro Thr Asp Ile Thr Gly Pro Leu Asn Leu Ser Asp Pro
                85                  90                  95

Ser Val Ser Thr Val Val
            100

(2) INFORMATION FOR SEQ ID NO: 21:

(i) SEQUENCE CHARACTERISTICS:
        (A) LENGTH: 100 base pairs
        (B) TYPE: nucleic acid
        (C) STRANDEDNESS: double
        (D) TOPOLOGY: linear (xi) SEQUENCE DESCRIPTION: SEQ ID NO: 21:

TGGAGGAGCG TGAGTCCAAG AGTAAAAAAA GGAACTATGA AAACCTCGAC CAACTGTCCT        60

ATGACAACAA GCGCGGACCC AAGGCAGAGA AGGTGCTGCA                             100

(2) INFORMATION FOR SEQ ID NO: 22:

(i) SEQUENCE CHARACTERISTICS:
        (A) LENGTH: 37 base pairs
        (B) TYPE: nucleic acid
        (C) STRANDEDNESS: double
        (D) TOPOLOGY: linear (xi) SEQUENCE DESCRIPTION: SEQ ID NO: 22:

TGGAGGAGCG TGAGTCCAAG GCAGAGAAGG TGCTGCA                                37

(2) INFORMATION FOR SEQ ID NO: 23:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO: 23:

Lys Arg Leu Glu Thr Leu Leu Glu Glu Arg Glu Ser Lys Ser Lys
1               5                   10                  15

Arg Asn Tyr Glu Asn Leu Asp Gln Leu Ser Tyr Asp Asn Lys Arg Gly

```
                        20                  25                  30
Pro Lys Ala Glu Lys Val Leu Gln Phe Asp Pro Gly Thr Lys Asn
            35                  40                  45

(2) INFORMATION FOR SEQ ID NO: 24:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO: 24:

Lys Arg Leu Glu Thr Leu Leu Glu Glu Arg Glu Ser Lys Ala Glu Lys
1               5                   10                  15

Val Leu Gln Phe Asp Pro Gly Thr Lys Asn
                20                  25

(2) INFORMATION FOR SEQ ID NO: 25:

(i) SEQUENCE CHARACTERISTICS:
        (A) LENGTH: 927 amino acids
        (B) TYPE: amino acid
        (D) TOPOLOGY: linear (ii) MOLECULE TYPE: protein (xi) SEQUENCE DESCRIPTION: SEQ ID NO: 25:

Met Ser Thr Met Arg Leu Leu Thr Leu Ala Leu Leu Phe Ser Cys Ser
1               5                   10                  15

Val Ala Arg Ala Ala Cys Asp Pro Lys Ile Val Asn Ile Gly Ala Val
                20                  25                  30

Leu Ser Thr Arg Lys His Glu Gln Met Phe Arg Glu Ala Val Asn Gln
            35                  40                  45

Ala Asn Lys Arg His Gly Ser Trp Lys Ile Gln Leu Asn Ala Thr Ser
        50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
        195                 200                 205

Met Glu Ala Lys Glu Leu Glu Ala Arg Val Ile Ile Leu Ser Ala Ser
    210                 215                 220

Glu Asp Asp Ala Ala Thr Val Tyr Arg Ala Ala Ala Met Leu Asn Met
225                 230                 235                 240
```

-continued

```
Thr Gly Ser Gly Tyr Val Trp Leu Val Gly Glu Arg Glu Ile Ser Gly
                245                 250                 255
Asn Ala Leu Arg Tyr Ala Pro Asp Gly Ile Leu Gly Leu Gln Leu Ile
            260                 265                 270
Asn Gly Lys Asn Glu Ser Ala His Ile Ser Asp Ala Val Gly Val Val
        275                 280                 285
Ala Gln Ala Val His Glu Leu Leu Glu Lys Glu Asn Ile Thr Asp Pro
    290                 295                 300
Pro Arg Gly Cys Val Gly Asn Thr Asn Ile Trp Lys Thr Gly Pro Leu
305                 310                 315                 320
Phe Lys Arg Val Leu Met Ser Ser Lys Tyr Ala Asp Gly Val Thr Gly
                325                 330                 335
Arg Val Glu Phe Asn Glu Asp Gly Asp Arg Lys Phe Ala Asn Tyr Ser
            340                 345                 350
Ile Met Asn Leu Gln Asn Arg Lys Leu Val Gln Val Gly Ile Tyr Asn
        355                 360                 365
Gly Thr His Val Ile Pro Asn Asp Arg Lys Ile Ile Trp Pro Gly Gly
    370                 375                 380
Glu Thr Glu Lys Pro Arg Gly Tyr Gln Met Ser Thr Arg Leu Lys Ile
385                 390                 395                 400
Val Thr Ile His Gln Glu Pro Phe Val Tyr Val Lys Pro Thr Leu Ser
                405                 410                 415
Asp Gly Thr Cys Lys Glu Glu Phe Thr Val Asn Gly Asp Pro Val Lys
            420                 425                 430
Lys Val Ile Cys Thr Gly Pro Asn Asp Thr Ser Pro Gly Ser Pro Arg
        435                 440                 445
His Thr Val Pro Gln Cys Cys Tyr Gly Phe Cys Ile Asp Leu Leu Ile
    450                 455                 460
Lys Leu Ala Arg Thr Met Asn Phe Thr Tyr Glu Val His Leu Val Ala
465                 470                 475                 480
Asp Gly Lys Phe Gly Thr Gln Glu Arg Val Asn Asn Ser Asn Lys Lys
                485                 490                 495
Glu Trp Asn Gly Met Met Gly Glu Leu Leu Ser Gly Gln Ala Asp Met
            500                 505                 510
Ile Val Ala Pro Leu Thr Ile Asn Asn Glu Arg Ala Gln Tyr Ile Glu
        515                 520                 525
Phe Ser Lys Pro Phe Lys Tyr Gln Gly Leu Thr Ile Leu Val Lys Lys
    530                 535                 540
Glu Ile Pro Arg Ser Thr Leu Asp Ser Phe Met Gln Pro Phe Gln Ser
545                 550                 555                 560
Thr Leu Trp Leu Leu Val Gly Leu Ser Val His Val Val Ala Val Met
                565                 570                 575
Leu Tyr Leu Leu Asp Arg Phe Ser Pro Phe Gly Arg Phe Lys Val Asn
            580                 585                 590
Ser Glu Glu Glu Glu Asp Ala Leu Thr Leu Ser Ser Ala Met Trp
        595                 600                 605
Phe Ser Trp Gly Val Leu Leu Asn Ser Gly Ile Gly Glu Gly Ala Pro
    610                 615                 620
Arg Ser Phe Ser Ala Arg Ile Leu Gly Met Val Trp Ala Gly Phe Ala
625                 630                 635                 640
Met Ile Ile Val Ala Ser Tyr Thr Ala Asn Leu Ala Ala Phe Leu Val
                645                 650                 655
```

```
Leu Asp Arg Pro Glu Glu Arg Ile Thr Gly Ile Asn Asp Pro Arg Leu
            660                 665                 670

Arg Asn Pro Ser Asp Lys Phe Ile Tyr Ala Thr Val Lys Gln Ser Ser
            675                 680                 685

Val Asp Ile Tyr Phe Arg Arg Gln Val Glu Leu Ser Thr Met Tyr Arg
            690                 695                 700

His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
                725                 730                 735

Glu Phe Glu Ala Ser Gln Lys Cys Asp Leu Val Thr Thr Gly Glu Leu
            740                 745                 750

Phe Phe Arg Ser Gly Phe Gly Ile Gly Met Arg Lys Asp Ser Pro Trp
            755                 760                 765

Lys Gln Asn Val Ser Leu Ser Ile Leu Lys Ser His Glu Asn Gly Phe
            770                 775                 780

Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
            820                 825                 830

Ile Glu Ile Ala Tyr Lys Arg His Lys Asp Ala Arg Arg Lys Gln Met
            835                 840                 845

Gln Leu Ala Phe Ala Ala Val Asn Val Trp Arg Lys Asn Leu Gln Gln
            850                 855                 860

Tyr His Pro Thr Asp Ile Thr Gly Pro Leu Asn Leu Ser Asp Pro Ser
865                 870                 875                 880

Val Ser Thr Val Val Lys Asn Leu Gln Ser Thr Gly Gly Gly Arg Gly
                885                 890                 895

Ala Leu Gln Asn Gln Lys Asp Thr Val Leu Pro Arg Arg Ala Ile Glu
            900                 905                 910

Arg Glu Glu Gly Gln Leu Gln Leu Cys Ser Arg His Arg Glu Ser
            915                 920                 925

(2) INFORMATION FOR SEQ ID NO: 26:

(i) SEQUENCE CHARACTERISTICS:
        (A) LENGTH: 964 amino acids
        (B) TYPE: amino acid
        (D) TOPOLOGY: linear (ii) MOLECULE TYPE: protein (xi) SEQUENCE DESCRIPTION: SEQ ID NO: 26:

Met Ser Thr Met Arg Leu Leu Thr Leu Ala Leu Leu Phe Ser Cys Ser
1               5                   10                  15

Val Ala Arg Ala Ala Cys Asp Pro Lys Ile Val Asn Ile Gly Ala Val
            20                  25                  30

Leu Ser Thr Arg Lys His Glu Gln Met Phe Arg Glu Ala Val Asn Gln
            35                  40                  45

Ala Asn Lys Arg His Gly Ser Trp Lys Ile Gln Leu Asn Ala Thr Ser
        50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
```

-continued

```
                    85                  90                  95
Thr Pro Asn Asp His Phe Thr Pro Thr Pro Val Ser Tyr Thr Ala Gly
                100                 105                 110
Phe Tyr Arg Ile Pro Val Leu Gly Leu Thr Thr Arg Met Ser Ile Tyr
            115                 120                 125
Ser Asp Lys Ser Ile His Leu Ser Phe Leu Arg Thr Val Pro Pro Tyr
        130                 135                 140
Ser His Gln Ser Ser Val Trp Phe Glu Met Met Arg Val Tyr Ser Trp
145                 150                 155                 160
Asn His Ile Ile Leu Leu Val Ser Asp His Glu Gly Arg Ala Ala
                165                 170                 175
Gln Lys Arg Leu Glu Thr Leu Leu Glu Glu Arg Glu Ser Lys Ala Glu
            180                 185                 190
Lys Val Leu Gln Phe Asp Pro Gly Thr Lys Asn Val Thr Ala Leu Leu
        195                 200                 205
Met Glu Ala Lys Glu Leu Glu Ala Arg Val Ile Ile Leu Ser Ala Ser
    210                 215                 220
Glu Asp Asp Ala Ala Thr Val Tyr Arg Ala Ala Met Leu Asn Met
225                 230                 235                 240
Thr Gly Ser Gly Tyr Val Trp Leu Val Gly Glu Arg Glu Ile Ser Gly
                245                 250                 255
Asn Ala Leu Arg Tyr Ala Pro Asp Gly Ile Leu Gly Leu Gln Leu Ile
            260                 265                 270
Asn Gly Lys Asn Glu Ser Ala His Ile Ser Asp Ala Val Gly Val Val
        275                 280                 285
Ala Gln Ala Val His Glu Leu Leu Glu Lys Glu Asn Ile Thr Asp Pro
    290                 295                 300
Pro Arg Gly Cys Val Gly Asn Thr Asn Ile Trp Lys Thr Gly Pro Leu
305                 310                 315                 320
Phe Lys Arg Val Leu Met Ser Ser Lys Tyr Ala Asp Gly Val Thr Gly
                325                 330                 335
Arg Val Glu Phe Asn Glu Asp Gly Asp Arg Lys Phe Ala Asn Tyr Ser
            340                 345                 350
Ile Met Asn Leu Gln Asn Arg Lys Leu Val Gln Val Gly Ile Tyr Asn
        355                 360                 365
Gly Thr His Val Ile Pro Asn Asp Arg Lys Ile Ile Trp Pro Gly Gly
    370                 375                 380
Glu Thr Glu Lys Pro Arg Gly Tyr Gln Met Ser Thr Arg Leu Lys Ile
385                 390                 395                 400
Val Thr Ile His Gln Glu Pro Phe Val Tyr Val Lys Pro Thr Leu Ser
                405                 410                 415
Asp Gly Thr Cys Lys Glu Glu Phe Thr Val Asn Gly Asp Pro Val Lys
            420                 425                 430
Lys Val Ile Cys Thr Gly Pro Asn Asp Thr Ser Pro Gly Ser Pro Arg
        435                 440                 445
His Thr Val Pro Gln Cys Cys Tyr Gly Phe Cys Ile Asp Leu Leu Ile
    450                 455                 460
Lys Leu Ala Arg Thr Met Asn Phe Thr Tyr Glu Val His Leu Val Ala
465                 470                 475                 480
Asp Gly Lys Phe Gly Thr Gln Glu Arg Val Asn Asn Ser Asn Lys Lys
                485                 490                 495
Glu Trp Asn Gly Met Met Gly Glu Leu Leu Ser Gly Gln Ala Asp Met
            500                 505                 510
```

```
Ile Val Ala Pro Leu Thr Ile Asn Asn Glu Arg Ala Gln Tyr Ile Glu
            515                 520                 525

Phe Ser Lys Pro Phe Lys Tyr Gln Gly Leu Thr Ile Leu Val Lys Lys
        530                 535                 540

Glu Ile Pro Arg Ser Thr Leu Asp Ser Phe Met Gln Pro Phe Gln Ser
545                 550                 555                 560

Thr Leu Trp Leu Leu Val Gly Leu Ser Val His Val Ala Val Met
                565                 570                 575

Leu Tyr Leu Leu Asp Arg Phe Ser Pro Phe Gly Arg Phe Lys Val Asn
            580                 585                 590

Ser Glu Glu Glu Glu Asp Ala Leu Thr Leu Ser Ser Ala Met Trp
        595                 600                 605

Phe Ser Trp Gly Val Leu Leu Asn Ser Gly Ile Gly Glu Gly Ala Pro
        610                 615                 620

Arg Ser Phe Ser Ala Arg Ile Leu Gly Met Val Trp Ala Gly Phe Ala
625                 630                 635                 640

Met Ile Ile Val Ala Ser Tyr Thr Ala Asn Leu Ala Ala Phe Leu Val
                645                 650                 655

Leu Asp Arg Pro Glu Glu Arg Ile Thr Gly Ile Asn Asp Pro Arg Leu
            660                 665                 670

Arg Asn Pro Ser Asp Lys Phe Ile Tyr Ala Thr Val Lys Gln Ser Ser
        675                 680                 685

Val Asp Ile Tyr Phe Arg Arg Gln Val Glu Leu Ser Thr Met Tyr Arg
        690                 695                 700

His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
                725                 730                 735

Glu Phe Glu Ala Ser Gln Lys Cys Asp Leu Val Thr Thr Gly Glu Leu
            740                 745                 750

Phe Phe Arg Ser Gly Phe Gly Ile Gly Met Arg Lys Asp Ser Pro Trp
        755                 760                 765

Lys Gln Asn Val Ser Leu Ser Ile Leu Lys Ser His Glu Asn Gly Phe
        770                 775                 780

Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
            820                 825                 830

Ile Glu Ile Ala Tyr Lys Arg His Lys Asp Ala Arg Arg Lys Gln Met
            835                 840                 845

Gln Leu Ala Phe Ala Ala Val Asn Val Trp Arg Lys Asn Leu Gln Gln
        850                 855                 860

Tyr His Pro Thr Asp Ile Thr Gly Pro Leu Asn Leu Ser Asp Pro Ser
865                 870                 875                 880

Val Ser Thr Val Val Lys Asn Leu Gln Asp Arg Lys Ser Gly Arg Ala
                885                 890                 895

Glu Pro Asp Pro Lys Lys Lys Ala Thr Phe Arg Ala Ile Thr Ser Thr
            900                 905                 910

Leu Ala Ser Ser Phe Lys Arg Arg Ser Ser Lys Asp Thr Ser Thr
        915                 920                 925
```

```
Gly Gly Gly Arg Gly Ala Leu Gln Asn Gln Lys Asp Thr Val Leu Pro
    930                 935                 940

Arg Arg Ala Ile Glu Arg Glu Glu Gly Gln Leu Gln Leu Cys Ser Arg
945                 950                 955                 960

His Arg Glu Ser (2) INFORMATION FOR SEQ ID NO: 27:

(i) SEQUENCE CHARACTERISTICS:
        (A) LENGTH: 964 amino acids
        (B) TYPE: amino acid
        (D) TOPOLOGY: linear (ii) MOLECULE TYPE: protein (xi) SEQUENCE DESCRIPTION: SEQ ID NO: 27:

Met Ser Thr Met Arg Leu Leu Thr Leu Ala Leu Leu Phe Ser Cys Ser
1               5                   10                  15

Val Ala Arg Ala Ala Cys Asp Pro Lys Ile Val Asn Ile Gly Ala Val
                20                  25                  30

Leu Ser Thr Arg Lys His Glu Gln Met Phe Arg Glu Ala Val Asn Gln
            35                  40                  45

Ala Asn Lys Arg His Gly Ser Trp Lys Ile Gln Leu Asn Ala Thr Ser
50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
        195                 200                 205

Met Glu Ala Lys Glu Leu Glu Ala Arg Val Ile Ile Leu Ser Ala Ser
210                 215                 220

Glu Asp Asp Ala Ala Thr Val Tyr Arg Ala Ala Met Leu Asn Met
225                 230                 235                 240

Thr Gly Ser Gly Tyr Val Trp Leu Val Gly Glu Arg Glu Ile Ser Gly
            245                 250                 255

Asn Ala Leu Arg Tyr Ala Pro Asp Gly Ile Leu Gly Leu Gln Leu Ile
        260                 265                 270

Asn Gly Lys Asn Glu Ser Ala His Ile Ser Asp Ala Val Gly Val Val
    275                 280                 285

Ala Gln Ala Val His Glu Leu Leu Glu Lys Glu Asn Ile Thr Asp Pro
    290                 295                 300

Pro Arg Gly Cys Val Gly Asn Thr Asn Ile Trp Lys Thr Gly Pro Leu
305                 310                 315                 320
```

```
Phe Lys Arg Val Leu Met Ser Ser Lys Tyr Ala Asp Gly Val Thr Gly
                325                 330                 335

Arg Val Glu Phe Asn Glu Asp Gly Asp Arg Lys Phe Ala Asn Tyr Ser
            340                 345                 350

Ile Met Asn Leu Gln Asn Arg Lys Leu Val Gln Val Gly Ile Tyr Asn
        355                 360                 365

Gly Thr His Val Ile Pro Asn Asp Arg Lys Ile Ile Trp Pro Gly Gly
    370                 375                 380

Glu Thr Glu Lys Pro Arg Gly Tyr Gln Met Ser Thr Arg Leu Lys Ile
385                 390                 395                 400

Val Thr Ile His Gln Glu Pro Phe Val Tyr Val Lys Pro Thr Leu Ser
            405                 410                 415

Asp Gly Thr Cys Lys Glu Glu Phe Thr Val Asn Gly Asp Pro Val Lys
        420                 425                 430

Lys Val Ile Cys Thr Gly Pro Asn Asp Thr Ser Pro Gly Ser Pro Arg
    435                 440                 445

His Thr Val Pro Gln Cys Cys Tyr Gly Phe Cys Ile Asp Leu Leu Ile
    450                 455                 460

Lys Leu Ala Arg Thr Met Asn Phe Thr Tyr Glu Val His Leu Val Ala
465                 470                 475                 480

Asp Gly Lys Phe Gly Thr Gln Glu Arg Val Asn Asn Ser Asn Lys Lys
            485                 490                 495

Glu Trp Asn Gly Met Met Gly Glu Leu Leu Ser Gly Gln Ala Asp Met
        500                 505                 510

Ile Val Ala Pro Leu Thr Ile Asn Asn Glu Arg Ala Gln Tyr Ile Glu
    515                 520                 525

Phe Ser Lys Pro Phe Lys Tyr Gln Gly Leu Thr Ile Leu Val Lys Lys
    530                 535                 540

Glu Ile Pro Arg Ser Thr Leu Asp Ser Phe Met Gln Pro Phe Gln Ser
545                 550                 555                 560

Thr Leu Trp Leu Leu Val Gly Leu Ser Val His Val Val Ala Val Met
            565                 570                 575

Leu Tyr Leu Leu Asp Arg Phe Ser Pro Phe Gly Arg Phe Lys Val Asn
        580                 585                 590

Ser Glu Glu Glu Glu Glu Asp Ala Leu Thr Leu Ser Ser Ala Met Trp
    595                 600                 605

Phe Ser Trp Gly Val Leu Leu Asn Ser Gly Ile Gly Glu Gly Ala Pro
    610                 615                 620

Arg Ser Phe Ser Ala Arg Ile Leu Gly Met Val Trp Ala Gly Phe Ala
625                 630                 635                 640

Met Ile Ile Val Ala Ser Tyr Thr Ala Asn Leu Ala Ala Phe Leu Val
            645                 650                 655

Leu Asp Arg Pro Glu Glu Arg Ile Thr Gly Ile Asn Asp Pro Arg Leu
        660                 665                 670

Arg Asn Pro Ser Asp Lys Phe Ile Tyr Ala Thr Val Lys Gln Ser Ser
    675                 680                 685

Val Asp Ile Tyr Phe Arg Arg Gln Val Glu Leu Ser Thr Met Tyr Arg
    690                 695                 700

His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
            725                 730                 735
```

-continued

```
Glu Phe Glu Ala Ser Gln Lys Cys Asp Leu Val Thr Thr Gly Glu Leu
            740                 745                 750

Phe Phe Arg Ser Gly Phe Gly Ile Gly Met Arg Lys Asp Ser Pro Trp
            755                 760                 765

Lys Gln Asn Val Ser Leu Ser Ile Leu Lys Ser His Glu Asn Gly Phe
            770                 775                 780

Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
                820                 825                 830

Ile Glu Ile Ala Tyr Lys Arg His Lys Asp Ala Arg Lys Gln Met
            835                 840                 845

Gln Leu Ala Phe Ala Ala Val Asn Val Trp Arg Lys Asn Leu Gln Gln
850                 855                 860

Tyr His Pro Thr Asp Ile Thr Gly Pro Leu Asn Leu Ser Asp Pro Ser
865                 870                 875                 880

Val Ser Thr Val Val Lys Asn Leu Gln Asp Arg Lys Ser Gly Arg Ala
                885                 890                 895

Glu Pro Asp Pro Lys Lys Ala Thr Phe Arg Ala Ile Thr Ser Thr
                900                 905                 910

Leu Ala Ser Ser Phe Lys Arg Arg Arg Ser Ser Lys Asp Thr Ser Thr
            915                 920                 925

Gly Gly Gly Arg Gly Ala Leu Gln Asn Gln Lys Asp Thr Val Leu Pro
            930                 935                 940

Arg Arg Ala Ile Glu Arg Glu Glu Gly Gln Leu Gln Leu Cys Ser Arg
945                 950                 955                 960

His Arg Glu Ser
```

(2) INFORMATION FOR SEQ ID NO: 28:

(i) SEQUENCE CHARACTERISTICS:
        (A) LENGTH: 922 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 28:

```
Met Ser Thr Met Arg Leu Leu Thr Leu Ala Leu Leu Phe Ser Cys Ser
1               5                   10                  15

Val Ala Arg Ala Ala Cys Asp Pro Lys Ile Val Asn Ile Gly Ala Val
                20                  25                  30

Leu Ser Thr Arg Lys His Glu Gln Met Phe Arg Glu Ala Val Asn Gln
            35                  40                  45

Ala Asn Lys Arg His Gly Ser Trp Lys Ile Gln Leu Asn Ala Thr Ser
        50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
```

-continued

```
                115                 120                 125
Ser Asp Lys Ser Ile His Leu Ser Phe Leu Arg Thr Val Pro Tyr
        130                 135                 140
Ser His Gln Ser Ser Val Trp Phe Glu Met Met Arg Val Tyr Ser Trp
145                 150                 155                 160
Asn His Ile Ile Leu Leu Val Ser Asp His Glu Gly Arg Ala Ala
                165                 170                 175
Gln Lys Arg Leu Glu Thr Leu Leu Glu Glu Arg Glu Ser Lys Ala Glu
                180                 185                 190
Lys Val Leu Gln Phe Asp Pro Gly Thr Lys Asn Val Thr Ala Leu Leu
                195                 200                 205
Met Glu Ala Lys Glu Leu Glu Ala Arg Val Ile Ile Leu Ser Ala Ser
        210                 215                 220
Glu Asp Asp Ala Ala Thr Val Tyr Arg Ala Ala Met Leu Asn Met
225                 230                 235                 240
Thr Gly Ser Gly Tyr Val Trp Leu Val Gly Glu Arg Glu Ile Ser Gly
                    245                 250                 255
Asn Ala Leu Arg Tyr Ala Pro Asp Gly Ile Leu Gly Leu Gln Leu Ile
                260                 265                 270
Asn Gly Lys Asn Glu Ser Ala His Ile Ser Asp Ala Val Gly Val Val
                275                 280                 285
Ala Gln Ala Val His Glu Leu Leu Glu Lys Glu Asn Ile Thr Asp Pro
        290                 295                 300
Pro Arg Gly Cys Val Gly Asn Thr Asn Ile Trp Lys Thr Gly Pro Leu
305                 310                 315                 320
Phe Lys Arg Val Leu Met Ser Ser Lys Tyr Ala Asp Gly Val Thr Gly
                325                 330                 335
Arg Val Glu Phe Asn Glu Asp Gly Asp Arg Lys Phe Ala Asn Tyr Ser
                340                 345                 350
Ile Met Asn Leu Gln Asn Arg Lys Leu Val Gln Val Gly Ile Tyr Asn
                355                 360                 365
Gly Thr His Val Ile Pro Asn Asp Arg Lys Ile Ile Trp Pro Gly Gly
        370                 375                 380
Glu Thr Glu Lys Pro Arg Gly Tyr Gln Met Ser Thr Arg Leu Lys Ile
385                 390                 395                 400
Val Thr Ile His Gln Glu Pro Phe Val Tyr Val Lys Pro Thr Leu Ser
                405                 410                 415
Asp Gly Thr Cys Lys Glu Glu Phe Thr Val Asn Gly Asp Pro Val Lys
                420                 425                 430
Lys Val Ile Cys Thr Gly Pro Asn Asp Thr Ser Pro Gly Ser Pro Arg
                435                 440                 445
His Thr Val Pro Gln Cys Cys Tyr Gly Phe Cys Ile Asp Leu Leu Ile
        450                 455                 460
Lys Leu Ala Arg Thr Met Asn Phe Thr Tyr Glu Val His Leu Val Ala
465                 470                 475                 480
Asp Gly Lys Phe Gly Thr Gln Glu Arg Val Asn Asn Ser Asn Lys Lys
                485                 490                 495
Glu Trp Asn Gly Met Met Gly Glu Leu Leu Ser Gly Gln Ala Asp Met
                500                 505                 510
Ile Val Ala Pro Leu Thr Ile Asn Asn Glu Arg Ala Gln Tyr Ile Glu
                515                 520                 525
Phe Ser Lys Pro Phe Lys Tyr Gln Gly Leu Thr Ile Leu Val Lys Lys
                530                 535                 540
```

```
Glu Ile Pro Arg Ser Thr Leu Asp Ser Phe Met Gln Pro Phe Gln Ser
545                 550                 555                 560

Thr Leu Trp Leu Leu Val Gly Leu Ser Val His Val Val Ala Val Met
                565                 570                 575

Leu Tyr Leu Leu Asp Arg Phe Ser Pro Phe Gly Arg Phe Lys Val Asn
            580                 585                 590

Ser Glu Glu Glu Glu Asp Ala Leu Thr Leu Ser Ser Ala Met Trp
        595                 600                 605

Phe Ser Trp Gly Val Leu Leu Asn Ser Gly Ile Gly Glu Gly Ala Pro
    610                 615                 620

Arg Ser Phe Ser Ala Arg Ile Leu Gly Met Val Trp Ala Gly Phe Ala
625                 630                 635                 640

Met Ile Ile Val Ala Ser Tyr Thr Ala Asn Leu Ala Ala Phe Leu Val
                645                 650                 655

Leu Asp Arg Pro Glu Glu Arg Ile Thr Gly Ile Asn Asp Pro Arg Leu
            660                 665                 670

Arg Asn Pro Ser Asp Lys Phe Ile Tyr Ala Thr Val Lys Gln Ser Ser
        675                 680                 685

Val Asp Ile Tyr Phe Arg Arg Gln Val Glu Leu Ser Thr Met Tyr Arg
690                 695                 700

His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
                725                 730                 735

Glu Phe Glu Ala Ser Gln Lys Cys Asp Leu Val Thr Thr Gly Glu Leu
            740                 745                 750

Phe Phe Arg Ser Gly Phe Gly Ile Gly Met Arg Lys Asp Ser Pro Trp
        755                 760                 765

Lys Gln Asn Val Ser Leu Ser Ile Leu Lys Ser His Glu Asn Gly Phe
770                 775                 780

Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
            820                 825                 830

Ile Glu Ile Ala Tyr Lys Arg His Lys Asp Ala Arg Arg Lys Gln Met
        835                 840                 845

Gln Leu Ala Phe Ala Ala Val Asn Val Trp Arg Lys Asn Leu Gln Asp
850                 855                 860

Arg Lys Ser Gly Arg Ala Glu Pro Asp Pro Lys Lys Lys Ala Thr Phe
865                 870                 875                 880

Arg Ala Ile Thr Ser Thr Leu Ala Ser Ser Phe Lys Arg Arg Arg Ser
                885                 890                 895

Ser Lys Asp Thr Gln Tyr His Pro Thr Asp Ile Thr Gly Pro Leu Asn
            900                 905                 910

Leu Ser Asp Pro Ser Val Ser Thr Val Val
        915                 920
```

(2) INFORMATION FOR SEQ ID NO: 29:

(i) SEQUENCE CHARACTERISTICS:
        (A) LENGTH: 906 amino acids
        (B) TYPE: amino acid (C) STRANDEDNESS: <Unknown>
        (D) TOPOLOGY: linear (ii) MOLECULE TYPE: protein (xi) SEQUENCE DESCRIPTION: SEQ ID NO: 29:

```
Met Ser Thr Met Arg Leu Leu Thr Leu Ala Leu Leu Phe Ser Cys Ser
1               5                   10                  15

Val Ala Arg Ala Ala Cys Asp Pro Lys Ile Val Asn Ile Gly Ala Val
            20                  25                  30

Leu Ser Thr Arg Lys His Glu Gln Met Phe Arg Glu Ala Val Asn Gln
            35                  40                  45

Ala Asn Lys Arg His Gly Ser Trp Lys Ile Gln Leu Asn Ala Thr Ser
50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
                100                 105                 110

Phe Tyr Arg Ile Pro Val Leu Gly Leu Thr Thr Arg Met Ser Ile Tyr
            115                 120                 125

Ser Asp Lys Ser Ile His Leu Ser Phe Leu Arg Thr Val Pro Pro Tyr
130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ser Lys
            180                 185                 190

Lys Arg Asn Tyr Glu Asn Leu Asp Gln Leu Ser Tyr Asp Asn Lys Arg
            195                 200                 205

Gly Pro Lys Ala Glu Lys Val Leu Gln Phe Asp Pro Gly Thr Lys Asn
210                 215                 220

Val Thr Ala Leu Leu Met Glu Ala Lys Glu Leu Glu Ala Arg Val Ile
225                 230                 235                 240

Ile Leu Ser Ala Ser Glu Asp Asp Ala Ala Thr Val Tyr Arg Ala Ala
                245                 250                 255

Ala Met Leu Asn Met Thr Gly Ser Gly Tyr Val Trp Leu Val Gly Glu
            260                 265                 270

Arg Glu Ile Ser Gly Asn Ala Leu Arg Tyr Ala Pro Asp Gly Ile Leu
            275                 280                 285

Gly Leu Gln Leu Ile Asn Gly Lys Asn Glu Ser Ala His Ile Ser Asp
290                 295                 300

Ala Val Gly Val Val Ala Gln Ala Val His Glu Leu Leu Glu Lys Glu
305                 310                 315                 320

Asn Ile Thr Asp Pro Pro Arg Gly Cys Val Gly Asn Thr Asn Ile Trp
                325                 330                 335

Lys Thr Gly Pro Leu Phe Lys Arg Val Leu Met Ser Ser Lys Tyr Ala
            340                 345                 350

Asp Gly Val Thr Gly Arg Val Glu Phe Asn Glu Asp Gly Asp Arg Lys
            355                 360                 365

Phe Ala Asn Tyr Ser Ile Met Asn Leu Gln Asn Arg Lys Leu Val Gln
370                 375                 380
```

-continued

```
Val Gly Ile Tyr Asn Gly Thr His Val Ile Pro Asn Asp Arg Lys Ile
385                 390                 395                 400

Ile Trp Pro Gly Gly Glu Thr Glu Lys Pro Arg Gly Tyr Gln Met Ser
                405                 410                 415

Thr Arg Leu Lys Ile Val Thr Ile His Gln Glu Pro Phe Val Tyr Val
            420                 425                 430

Lys Pro Thr Leu Ser Asp Gly Thr Cys Lys Glu Phe Thr Val Asn
            435                 440                 445

Gly Asp Pro Val Lys Lys Val Ile Cys Thr Gly Pro Asn Asp Thr Ser
        450                 455                 460

Pro Gly Ser Pro Arg His Thr Val Pro Gln Cys Cys Tyr Gly Phe Cys
465                 470                 475                 480

Ile Asp Leu Leu Ile Lys Leu Ala Arg Thr Met Asn Phe Thr Tyr Glu
                485                 490                 495

Val His Leu Val Ala Asp Gly Lys Phe Gly Thr Gln Glu Arg Val Asn
            500                 505                 510

Asn Ser Asn Lys Lys Glu Trp Asn Gly Met Met Gly Glu Leu Leu Ser
            515                 520                 525

Gly Gln Ala Asp Met Ile Val Ala Pro Leu Thr Ile Asn Asn Glu Arg
    530                 535                 540

Ala Gln Tyr Ile Glu Phe Ser Lys Pro Phe Lys Tyr Gln Gly Leu Thr
545                 550                 555                 560

Ile Leu Val Lys Lys Glu Ile Pro Arg Ser Thr Leu Asp Ser Phe Met
                565                 570                 575

Gln Pro Phe Gln Ser Thr Leu Trp Leu Leu Val Gly Leu Ser Val His
                580                 585                 590

Val Val Ala Val Met Leu Tyr Leu Leu Asp Arg Phe Ser Pro Phe Gly
            595                 600                 605

Arg Phe Lys Val Asn Ser Glu Glu Glu Glu Asp Ala Leu Thr Leu
            610                 615                 620

Ser Ser Ala Met Trp Phe Ser Trp Gly Val Leu Leu Asn Ser Gly Ile
625                 630                 635                 640

Gly Glu Gly Ala Pro Arg Ser Phe Ser Ala Arg Ile Leu Gly Met Val
                645                 650                 655

Trp Ala Gly Phe Ala Met Ile Ile Val Ala Ser Tyr Thr Ala Asn Leu
                660                 665                 670

Ala Ala Phe Leu Val Leu Asp Arg Pro Glu Glu Arg Ile Thr Gly Ile
            675                 680                 685

Asn Asp Pro Arg Leu Arg Asn Pro Ser Asp Lys Phe Ile Tyr Ala Thr
        690                 695                 700

Val Lys Gln Ser Ser Val Asp Ile Tyr Phe Arg Arg Gln Val Glu Leu
705                 710                 715                 720

Ser Thr Met Tyr Arg His Met Glu Lys His Asn Tyr Glu Ser Ala Ala
                725                 730                 735

Glu Ala Ile Gln Ala Val Arg Asp Asn Lys Leu His Ala Phe Ile Trp
            740                 745                 750

Asp Ser Ala Val Leu Glu Phe Glu Ala Ser Gln Lys Cys Asp Leu Val
        755                 760                 765

Thr Thr Gly Glu Leu Phe Phe Arg Ser Gly Phe Gly Ile Gly Met Arg
    770                 775                 780

Lys Asp Ser Pro Trp Lys Gln Asn Val Ser Leu Ser Ile Leu Lys Ser
785                 790                 795                 800

His Glu Asn Gly Phe Met Glu Asp Leu Asp Lys Thr Trp Val Arg Tyr
```

```
                    805                 810                 815
Gln Glu Cys Asp Ser Arg Ser Asn Ala Pro Ala Thr Leu Thr Phe Glu
            820                 825                 830

Asn Met Ala Gly Val Phe Met Leu Val Ala Gly Gly Ile Val Ala Gly
        835                 840                 845

Ile Phe Leu Ile Phe Ile Glu Ile Ala Tyr Lys Arg His Lys Asp Ala
    850                 855                 860

Arg Arg Lys Gln Met Gln Leu Ala Phe Ala Ala Val Asn Val Trp Arg
865                 870                 875                 880

Lys Asn Leu Gln Gln Tyr His Pro Thr Asp Ile Thr Gly Pro Leu Asn
                885                 890                 895

Leu Ser Asp Pro Ser Val Ser Thr Val Val
            900                 905

(2) INFORMATION FOR SEQ ID NO: 30:

(i) SEQUENCE CHARACTERISTICS:
         (A) LENGTH: 948 amino acids
         (B) TYPE: amino acid
         (C) STRANDEDNESS: <Unknown>
         (D) TOPOLOGY: linear (ii) MOLECULE TYPE: protein (xi) SEQUENCE DESCRIPTION: SEQ ID NO: 30:

Met Ser Thr Met Arg Leu Leu Thr Leu Ala Leu Leu Phe Ser Cys Ser
1               5                   10                  15

Val Ala Arg Ala Ala Cys Asp Pro Lys Ile Val Asn Ile Gly Ala Val
            20                  25                  30

Leu Ser Thr Arg Lys His Glu Gln Met Phe Arg Glu Ala Val Asn Gln
        35                  40                  45

Ala Asn Lys Arg His Gly Ser Trp Lys Ile Gln Leu Asn Ala Thr Ser
    50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ser Lys
            180                 185                 190

Lys Arg Asn Tyr Glu Asn Leu Asp Gln Leu Ser Tyr Asp Asn Lys Arg
        195                 200                 205

Gly Pro Lys Ala Glu Lys Val Leu Gln Phe Asp Pro Gly Thr Lys Asn
    210                 215                 220

Val Thr Ala Leu Leu Met Glu Ala Lys Glu Leu Glu Ala Arg Val Ile
225                 230                 235                 240

Ile Leu Ser Ala Ser Glu Asp Asp Ala Ala Thr Val Tyr Arg Ala Ala
```

-continued

```
                245                 250                 255
Ala Met Leu Asn Met Thr Gly Ser Gly Tyr Val Trp Leu Val Gly Glu
                260                 265                 270
Arg Glu Ile Ser Gly Asn Ala Leu Arg Tyr Ala Pro Asp Gly Ile Leu
                275                 280                 285
Gly Leu Gln Leu Ile Asn Gly Lys Asn Glu Ser Ala His Ile Ser Asp
                290                 295                 300
Ala Val Gly Val Val Ala Gln Ala Val His Glu Leu Leu Glu Lys Glu
305                 310                 315                 320
Asn Ile Thr Asp Pro Pro Arg Gly Cys Val Gly Asn Thr Asn Ile Trp
                325                 330                 335
Lys Thr Gly Pro Leu Phe Lys Arg Val Leu Met Ser Ser Lys Tyr Ala
                340                 345                 350
Asp Gly Val Thr Gly Arg Val Glu Phe Asn Glu Asp Gly Asp Arg Lys
                355                 360                 365
Phe Ala Asn Tyr Ser Ile Met Asn Leu Gln Asn Arg Lys Leu Val Gln
                370                 375                 380
Val Gly Ile Tyr Asn Gly Thr His Val Ile Pro Asn Asp Arg Lys Ile
385                 390                 395                 400
Ile Trp Pro Gly Gly Glu Thr Glu Lys Pro Arg Gly Tyr Gln Met Ser
                405                 410                 415
Thr Arg Leu Lys Ile Val Thr Ile His Gln Glu Pro Phe Val Tyr Val
                420                 425                 430
Lys Pro Thr Leu Ser Asp Gly Thr Cys Lys Glu Glu Phe Thr Val Asn
                435                 440                 445
Gly Asp Pro Val Lys Lys Val Ile Cys Thr Gly Pro Asn Asp Thr Ser
450                 455                 460
Pro Gly Ser Pro Arg His Thr Val Pro Gln Cys Cys Tyr Gly Phe Cys
465                 470                 475                 480
Ile Asp Leu Leu Ile Lys Leu Ala Arg Thr Met Asn Phe Thr Tyr Glu
                485                 490                 495
Val His Leu Val Ala Asp Gly Lys Phe Gly Thr Gln Glu Arg Val Asn
                500                 505                 510
Asn Ser Asn Lys Lys Glu Trp Asn Gly Met Met Gly Glu Leu Leu Ser
                515                 520                 525
Gly Gln Ala Asp Met Ile Val Ala Pro Leu Thr Ile Asn Asn Glu Arg
530                 535                 540
Ala Gln Tyr Ile Glu Phe Ser Lys Pro Phe Lys Tyr Gln Gly Leu Thr
545                 550                 555                 560
Ile Leu Val Lys Lys Glu Ile Pro Arg Ser Thr Leu Asp Ser Phe Met
                565                 570                 575
Gln Pro Phe Gln Ser Thr Leu Trp Leu Leu Val Gly Leu Ser Val His
                580                 585                 590
Val Val Ala Val Met Leu Tyr Leu Leu Asp Arg Phe Ser Pro Phe Gly
                595                 600                 605
Arg Phe Lys Val Asn Ser Glu Glu Glu Glu Asp Ala Leu Thr Leu
                610                 615                 620
Ser Ser Ala Met Trp Phe Ser Trp Gly Val Leu Leu Asn Ser Gly Ile
625                 630                 635                 640
Gly Glu Gly Ala Pro Arg Ser Phe Ser Ala Arg Ile Leu Gly Met Val
                645                 650                 655
Trp Ala Gly Phe Ala Met Ile Ile Val Ala Ser Tyr Thr Ala Asn Leu
                660                 665                 670
```

```
Ala Ala Phe Leu Val Leu Asp Arg Pro Glu Glu Arg Ile Thr Gly Ile
            675                 680                 685

Asn Asp Pro Arg Leu Arg Asn Pro Ser Asp Lys Phe Ile Tyr Ala Thr
    690                 695                 700

Val Lys Gln Ser Ser Val Asp Ile Tyr Phe Arg Arg Gln Val Glu Leu
705                 710                 715                 720

Ser Thr Met Tyr Arg His Met Glu Lys His Asn Tyr Glu Ser Ala Ala
                725                 730                 735

Glu Ala Ile Gln Ala Val Arg Asp Asn Lys Leu His Ala Phe Ile Trp
            740                 745                 750

Asp Ser Ala Val Leu Glu Phe Glu Ala Ser Gln Lys Cys Asp Leu Val
        755                 760                 765

Thr Thr Gly Glu Leu Phe Phe Arg Ser Gly Phe Gly Ile Gly Met Arg
770                 775                 780

Lys Asp Ser Pro Trp Lys Gln Asn Val Ser Leu Ser Ile Leu Lys Ser
785                 790                 795                 800

His Glu Asn Gly Phe Met Glu Asp Leu Asp Lys Thr Trp Val Arg Tyr
                805                 810                 815

Gln Glu Cys Asp Ser Arg Ser Asn Ala Pro Ala Thr Leu Thr Phe Glu
            820                 825                 830

Asn Met Ala Gly Val Phe Met Leu Val Ala Gly Gly Ile Val Ala Gly
        835                 840                 845

Ile Phe Leu Ile Phe Ile Glu Ile Ala Tyr Lys Arg His Lys Asp Ala
    850                 855                 860

Arg Arg Lys Gln Met Gln Leu Ala Phe Ala Ala Val Asn Val Trp Arg
865                 870                 875                 880

Lys Asn Leu Gln Gln Tyr His Pro Thr Asp Ile Thr Gly Pro Leu Asn
                885                 890                 895

Leu Ser Asp Pro Ser Val Ser Thr Val Val Lys Asn Leu Gln Ser Thr
            900                 905                 910

Gly Gly Gly Arg Gly Ala Leu Gln Asn Gln Lys Asp Thr Val Leu Pro
        915                 920                 925

Arg Arg Ala Ile Glu Arg Glu Glu Gly Gln Leu Gln Leu Cys Ser Arg
930                 935                 940

His Arg Glu Ser
945

(2) INFORMATION FOR SEQ ID NO: 31:

(i) SEQUENCE CHARACTERISTICS:
        (A) LENGTH: 985 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 31:

Met Ser Thr Met Arg Leu Leu Thr Leu Ala Leu Leu Phe Ser Cys Ser
1               5                   10                  15

Val Ala Arg Ala Ala Cys Asp Pro Lys Ile Val Asn Ile Gly Ala Val
            20                  25                  30

Leu Ser Thr Arg Lys His Glu Gln Met Phe Arg Glu Ala Val Asn Gln
        35                  40                  45

Ala Asn Lys Arg His Gly Ser Trp Lys Ile Gln Leu Asn Ala Thr Ser
    50                  55                  60
```

```
Val Thr His Lys Pro Asn Ala Ile Gln Met Ala Leu Ser Val Cys Glu
 65                  70                  75                  80

Asp Leu Ile Ser Ser Gln Val Tyr Ala Ile Leu Val Ser His Pro Pro
                 85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ser Lys
            180                 185                 190

Lys Arg Asn Tyr Glu Asn Leu Asp Gln Leu Ser Tyr Asp Asn Lys Arg
        195                 200                 205

Gly Pro Lys Ala Glu Lys Val Leu Gln Phe Asp Pro Gly Thr Lys Asn
210                 215                 220

Val Thr Ala Leu Leu Met Glu Ala Lys Glu Leu Glu Ala Arg Val Ile
225                 230                 235                 240

Ile Leu Ser Ala Ser Glu Asp Asp Ala Ala Thr Val Tyr Arg Ala Ala
                245                 250                 255

Ala Met Leu Asn Met Thr Gly Ser Gly Tyr Val Trp Leu Val Gly Glu
            260                 265                 270

Arg Glu Ile Ser Gly Asn Ala Leu Arg Tyr Ala Pro Asp Gly Ile Leu
        275                 280                 285

Gly Leu Gln Leu Ile Asn Gly Lys Asn Glu Ser Ala His Ile Ser Asp
290                 295                 300

Ala Val Gly Val Val Ala Gln Ala Val His Glu Leu Leu Glu Lys Glu
305                 310                 315                 320

Asn Ile Thr Asp Pro Pro Arg Gly Cys Val Gly Asn Thr Asn Ile Trp
                325                 330                 335

Lys Thr Gly Pro Leu Phe Lys Arg Val Leu Met Ser Ser Lys Tyr Ala
            340                 345                 350

Asp Gly Val Thr Gly Arg Val Glu Phe Asn Glu Asp Gly Asp Arg Lys
        355                 360                 365

Phe Ala Asn Tyr Ser Ile Met Asn Leu Gln Asn Arg Lys Leu Val Gln
370                 375                 380

Val Gly Ile Tyr Asn Gly Thr His Val Ile Pro Asn Asp Arg Lys Ile
385                 390                 395                 400

Ile Trp Pro Gly Gly Glu Thr Glu Lys Pro Arg Gly Tyr Gln Met Ser
                405                 410                 415

Thr Arg Leu Lys Ile Val Thr Ile His Gln Glu Pro Phe Val Tyr Val
            420                 425                 430

Lys Pro Thr Leu Ser Asp Gly Thr Cys Lys Glu Glu Phe Thr Val Asn
        435                 440                 445

Gly Asp Pro Val Lys Lys Val Ile Cys Thr Gly Pro Asn Asp Thr Ser
450                 455                 460

Pro Gly Ser Pro Arg His Thr Val Pro Gln Cys Cys Tyr Gly Phe Cys
465                 470                 475                 480
```

-continued

```
Ile Asp Leu Leu Ile Lys Leu Ala Arg Thr Met Asn Phe Thr Tyr Glu
                485                 490                 495

Val His Leu Val Ala Asp Gly Lys Phe Gly Thr Gln Glu Arg Val Asn
            500                 505                 510

Asn Ser Asn Lys Lys Glu Trp Asn Gly Met Met Gly Glu Leu Leu Ser
            515                 520                 525

Gly Gln Ala Asp Met Ile Val Ala Pro Leu Thr Ile Asn Asn Glu Arg
        530                 535                 540

Ala Gln Tyr Ile Glu Phe Ser Lys Pro Phe Lys Tyr Gln Gly Leu Thr
545                 550                 555                 560

Ile Leu Val Lys Lys Glu Ile Pro Arg Ser Thr Leu Asp Ser Phe Met
                565                 570                 575

Gln Pro Phe Gln Ser Thr Leu Trp Leu Leu Val Gly Leu Ser Val His
            580                 585                 590

Val Val Ala Val Met Leu Tyr Leu Leu Asp Arg Phe Ser Pro Phe Gly
        595                 600                 605

Arg Phe Lys Val Asn Ser Glu Glu Glu Glu Asp Ala Leu Thr Leu
        610                 615                 620

Ser Ser Ala Met Trp Phe Ser Trp Gly Val Leu Leu Asn Ser Gly Ile
625                 630                 635                 640

Gly Glu Gly Ala Pro Arg Ser Phe Ser Ala Arg Ile Leu Gly Met Val
                645                 650                 655

Trp Ala Gly Phe Ala Met Ile Ile Val Ala Ser Tyr Thr Ala Asn Leu
            660                 665                 670

Ala Ala Phe Leu Val Leu Asp Arg Pro Glu Glu Arg Ile Thr Gly Ile
        675                 680                 685

Asn Asp Pro Arg Leu Arg Asn Pro Ser Asp Lys Phe Ile Tyr Ala Thr
        690                 695                 700

Val Lys Gln Ser Ser Val Asp Ile Tyr Phe Arg Arg Gln Val Glu Leu
705                 710                 715                 720

Ser Thr Met Tyr Arg His Met Glu Lys His Asn Tyr Glu Ser Ala Ala
                725                 730                 735

Glu Ala Ile Gln Ala Val Arg Asp Asn Lys Leu His Ala Phe Ile Trp
            740                 745                 750

Asp Ser Ala Val Leu Glu Phe Glu Ala Ser Gln Lys Cys Asp Leu Val
            755                 760                 765

Thr Thr Gly Glu Leu Phe Phe Arg Ser Gly Phe Gly Ile Gly Met Arg
770                 775                 780

Lys Asp Ser Pro Trp Lys Gln Asn Val Ser Leu Ser Ile Leu Lys Ser
785                 790                 795                 800

His Glu Asn Gly Phe Met Glu Asp Leu Asp Lys Thr Trp Val Arg Tyr
                805                 810                 815

Gln Glu Cys Asp Ser Arg Ser Asn Ala Pro Ala Thr Leu Thr Phe Glu
            820                 825                 830

Asn Met Ala Gly Val Phe Met Leu Val Ala Gly Gly Ile Val Ala Gly
        835                 840                 845

Ile Phe Leu Ile Phe Ile Glu Ile Ala Tyr Lys Arg His Lys Asp Ala
        850                 855                 860

Arg Arg Lys Gln Met Gln Leu Ala Phe Ala Ala Val Asn Val Trp Arg
865                 870                 875                 880

Lys Asn Leu Gln Gln Tyr His Pro Thr Asp Ile Thr Gly Pro Leu Asn
                885                 890                 895

Leu Ser Asp Pro Ser Val Ser Thr Val Val Lys Asn Leu Gln Asp Arg
```

```
                     900                 905                 910
Lys Ser Gly Arg Ala Glu Pro Asp Pro Lys Lys Ala Thr Phe Arg
            915                 920                 925

Ala Ile Thr Ser Thr Leu Ala Ser Ser Phe Lys Arg Arg Ser Ser
    930                 935                 940

Lys Asp Thr Ser Thr Gly Gly Gly Arg Gly Ala Leu Gln Asn Gln Lys
945                 950                 955                 960

Asp Thr Val Leu Pro Arg Arg Ala Ile Glu Arg Glu Gly Gln Leu
                965                 970                 975

Gln Leu Cys Ser Arg His Arg Glu Ser
            980                 985

(2) INFORMATION FOR SEQ ID NO: 32:

(i) SEQUENCE CHARACTERISTICS:
        (A) LENGTH: 985 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 32:

Met Ser Thr Met Arg Leu Leu Thr Leu Ala Leu Leu Phe Ser Cys Ser
1               5                  10                  15

Val Ala Arg Ala Ala Cys Asp Pro Lys Ile Val Asn Ile Gly Ala Val
            20                  25                  30

Leu Ser Thr Arg Lys His Glu Gln Met Phe Arg Glu Ala Val Asn Gln
            35                  40                  45

Ala Asn Lys Arg His Gly Ser Trp Lys Ile Gln Leu Asn Ala Thr Ser
    50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
            115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ser Lys
            180                 185                 190

Lys Arg Asn Tyr Glu Asn Leu Asp Gln Leu Ser Tyr Asp Asn Lys Arg
            195                 200                 205

Gly Pro Lys Ala Glu Lys Val Leu Gln Phe Asp Pro Gly Thr Lys Asn
    210                 215                 220

Val Thr Ala Leu Leu Met Glu Ala Lys Glu Leu Glu Ala Arg Val Ile
225                 230                 235                 240

Ile Leu Ser Ala Ser Glu Asp Asp Ala Ala Thr Val Tyr Arg Ala Ala
                245                 250                 255

Ala Met Leu Asn Met Thr Gly Ser Gly Tyr Val Trp Leu Val Gly Glu
```

-continued

```
            260                 265                 270
Arg Glu Ile Ser Gly Asn Ala Leu Arg Tyr Ala Pro Asp Gly Ile Leu
            275                 280                 285
Gly Leu Gln Leu Ile Asn Gly Lys Asn Glu Ser Ala His Ile Ser Asp
            290                 295                 300
Ala Val Gly Val Ala Gln Ala Val His Glu Leu Leu Glu Lys Glu
305                 310                 315                 320
Asn Ile Thr Asp Pro Pro Arg Gly Cys Val Gly Asn Thr Asn Ile Trp
                325                 330                 335
Lys Thr Gly Pro Leu Phe Lys Arg Val Leu Met Ser Ser Lys Tyr Ala
                340                 345                 350
Asp Gly Val Thr Gly Arg Val Glu Phe Asn Glu Asp Gly Asp Arg Lys
                355                 360                 365
Phe Ala Asn Tyr Ser Ile Met Asn Leu Gln Asn Arg Lys Leu Val Gln
                370                 375                 380
Val Gly Ile Tyr Asn Gly Thr His Val Ile Pro Asn Asp Arg Lys Ile
385                 390                 395                 400
Ile Trp Pro Gly Gly Glu Thr Glu Lys Pro Arg Gly Tyr Gln Met Ser
                405                 410                 415
Thr Arg Leu Lys Ile Val Thr Ile His Gln Glu Pro Phe Val Tyr Val
                420                 425                 430
Lys Pro Thr Leu Ser Asp Gly Thr Cys Lys Glu Glu Phe Thr Val Asn
                435                 440                 445
Gly Asp Pro Val Lys Lys Val Ile Cys Thr Gly Pro Asn Asp Thr Ser
            450                 455                 460
Pro Gly Ser Pro Arg His Thr Val Pro Gln Cys Cys Tyr Gly Phe Cys
465                 470                 475                 480
Ile Asp Leu Leu Ile Lys Leu Ala Arg Thr Met Asn Phe Thr Tyr Glu
                485                 490                 495
Val His Leu Val Ala Asp Gly Lys Phe Gly Thr Gln Glu Arg Val Asn
                500                 505                 510
Asn Ser Asn Lys Lys Glu Trp Asn Gly Met Met Gly Glu Leu Leu Ser
            515                 520                 525
Gly Gln Ala Asp Met Ile Val Ala Pro Leu Thr Ile Asn Asn Glu Arg
            530                 535                 540
Ala Gln Tyr Ile Glu Phe Ser Lys Pro Phe Lys Tyr Gln Gly Leu Thr
545                 550                 555                 560
Ile Leu Val Lys Lys Glu Ile Pro Arg Ser Thr Leu Asp Ser Phe Met
                565                 570                 575
Gln Pro Phe Gln Ser Thr Leu Trp Leu Leu Val Gly Leu Ser Val His
            580                 585                 590
Val Val Ala Val Met Leu Tyr Leu Leu Asp Arg Phe Ser Pro Phe Gly
            595                 600                 605
Arg Phe Lys Val Asn Ser Glu Glu Glu Glu Asp Ala Leu Thr Leu
            610                 615                 620
Ser Ser Ala Met Trp Phe Ser Trp Gly Val Leu Leu Asn Ser Gly Ile
625                 630                 635                 640
Gly Glu Gly Ala Pro Arg Ser Phe Ser Ala Arg Ile Leu Gly Met Val
                645                 650                 655
Trp Ala Gly Phe Ala Met Ile Ile Val Ala Ser Tyr Thr Ala Asn Leu
                660                 665                 670
Ala Ala Phe Leu Val Leu Asp Arg Pro Glu Glu Arg Ile Thr Gly Ile
                675                 680                 685
```

```
Asn Asp Pro Arg Leu Arg Asn Pro Ser Asp Lys Phe Ile Tyr Ala Thr
    690                 695                 700

Val Lys Gln Ser Ser Val Asp Ile Tyr Phe Arg Arg Gln Val Glu Leu
705                 710                 715                 720

Ser Thr Met Tyr Arg His Met Glu Lys His Asn Tyr Glu Ser Ala Ala
                725                 730                 735

Glu Ala Ile Gln Ala Val Arg Asp Asn Lys Leu His Ala Phe Ile Trp
            740                 745                 750

Asp Ser Ala Val Leu Glu Phe Glu Ala Ser Gln Lys Cys Asp Leu Val
        755                 760                 765

Thr Thr Gly Glu Leu Phe Phe Arg Ser Gly Phe Gly Ile Gly Met Arg
    770                 775                 780

Lys Asp Ser Pro Trp Lys Gln Asn Val Ser Leu Ser Ile Leu Lys Ser
785                 790                 795                 800

His Glu Asn Gly Phe Met Glu Asp Leu Asp Lys Thr Trp Val Arg Tyr
                805                 810                 815

Gln Glu Cys Asp Ser Arg Ser Asn Ala Pro Ala Thr Leu Thr Phe Glu
            820                 825                 830

Asn Met Ala Gly Val Phe Met Leu Val Ala Gly Gly Ile Val Ala Gly
            835                 840                 845

Ile Phe Leu Ile Phe Ile Glu Ile Ala Tyr Lys Arg His Lys Asp Ala
    850                 855                 860

Arg Arg Lys Gln Met Gln Leu Ala Phe Ala Ala Val Asn Val Trp Arg
865                 870                 875                 880

Lys Asn Leu Gln Gln Tyr His Pro Thr Asp Ile Thr Gly Pro Leu Asn
            885                 890                 895

Leu Ser Asp Pro Ser Val Ser Thr Val Val Lys Asn Leu Gln Asp Arg
            900                 905                 910

Lys Ser Gly Arg Ala Glu Pro Asp Pro Lys Lys Lys Ala Thr Phe Arg
        915                 920                 925

Ala Ile Thr Ser Thr Leu Ala Ser Ser Phe Lys Arg Arg Arg Ser Ser
        930                 935                 940

Lys Asp Thr Ser Thr Gly Gly Gly Arg Gly Ala Leu Gln Asn Gln Lys
945                 950                 955                 960

Asp Thr Val Leu Pro Arg Arg Ala Ile Glu Arg Glu Glu Gly Gln Leu
                965                 970                 975

Gln Leu Cys Ser Arg His Arg Glu Ser
            980                 985
```